US010813376B2

(12) United States Patent
Kimrey, Jr. et al.

(10) Patent No.: US 10,813,376 B2
(45) Date of Patent: Oct. 27, 2020

(54) CONVEY LINE CARRIER FOR MICROWAVE HEATING

(71) Applicant: 915 Labs, LLC, Centennial, CO (US)

(72) Inventors: Harold Dail Kimrey, Jr., Knoxville, TN (US); David Behringer, Denver, CO (US); Li Zhang, Alpharetta, GA (US)

(73) Assignee: 915 Labs, Inc., Denver, CO (US)

( * ) Notice: Subject to any disclaimer, the term of this patent is extended or adjusted under 35 U.S.C. 154(b) by 354 days.

(21) Appl. No.: 15/723,971

(22) Filed: Oct. 3, 2017

(65) Prior Publication Data
US 2018/0092384 A1 Apr. 5, 2018

Related U.S. Application Data

(60) Provisional application No. 62/403,533, filed on Oct. 3, 2016.

(51) Int. Cl.
B65G 17/32 (2006.01)
H05B 6/78 (2006.01)
(Continued)

(52) U.S. Cl.
CPC .............. A23L 3/04 (2013.01); H05B 6/6408 (2013.01); H05B 6/78 (2013.01); H05B 6/782 (2013.01);
(Continued)

(58) Field of Classification Search
None
See application file for complete search history.

(56) References Cited

U.S. PATENT DOCUMENTS 3,145,870 A  8/1964  Lockwood
4,256,944 A  3/1981  Brandon
(Continued)

FOREIGN PATENT DOCUMENTS

CA  2961408  3/2016
CN  106465491  2/2017
(Continued)

OTHER PUBLICATIONS

International Search Report and Written Opinion for related PCT Application No. PCT/US20161055189, dated Feb. 16, 2017; 17 pages.
(Continued)

Primary Examiner — Kavel Singh
(74) Attorney, Agent, or Firm — Polsinelli PC

(57) ABSTRACT

Carriers suitable for transporting a plurality of articles through a microwave heating zone are provided. Carriers as described herein may include an outer frame and upper and lower support structures vertically spaced from one another to provide a cargo volume into which the articles are loaded. At least a portion of the upper and/or lower support structures may be formed of an electrically conductive material. Additionally, the carrier may include removable article spacing members, such as vertical spacing members and dividers, that can be selectively inserted to adjust the size and/or shape of the cargo volume. Carriers as described herein may be configured to receive a variety of different articles, including trays and pouches, and the articles may be loaded into the carrier in a nested or overlapping manner.

20 Claims, 28 Drawing Sheets

(51) Int. Cl.
*A23L 3/04* (2006.01)
*H05B 6/64* (2006.01)
*A61L 2/12* (2006.01)
*A61L 2/00* (2006.01)

(52) U.S. Cl.
CPC ......... *A23V 2002/00* (2013.01); *A61L 2/0023* (2013.01); *A61L 2/12* (2013.01); *A61L 2202/21* (2013.01); *A61L 2202/24* (2013.01); *H05B 2206/045* (2013.01)

(56) References Cited

U.S. PATENT DOCUMENTS

| | | | |
|---|---|---|---|
| 4,822,967 A | 4/1989 | Kumagami et al. | |
| 5,185,506 A | 2/1993 | Walters | |
| 5,298,707 A | 3/1994 | Sprecher et al. | |
| 5,488,784 A | 2/1996 | Woodmansee et al. | |
| 5,910,268 A | 6/1999 | Keefer | |
| 5,968,570 A | 10/1999 | Paulucci | |
| 6,844,534 B2 | 1/2005 | Haamer | |
| 7,119,313 B2 | 10/2006 | Tang et al. | |
| 7,183,527 B2 * | 2/2007 | Germain | B65G 15/58 219/701 |
| 7,996,306 B2 | 8/2011 | Gonen et al. | |
| 8,640,853 B2 * | 2/2014 | Arimatsu | B65B 35/24 198/401 |
| 8,845,983 B2 | 9/2014 | Feilders et al. | |
| 8,981,270 B2 | 3/2015 | Tang et al. | |
| 9,049,751 B1 | 6/2015 | Erle | |
| 9,642,385 B2 | 5/2017 | Tang et al. | |
| 9,955,711 B2 | 5/2018 | Newman | |
| 10,397,988 B2 * | 8/2019 | Kimrey, Jr. | H05B 6/6408 |
| 2004/0104514 A1 | 6/2004 | Ishikawa et al. | |
| 2005/0145623 A1 | 7/2005 | Pool, III et al. | |
| 2005/0199618 A1 | 9/2005 | Cook et al. | |
| 2006/0231550 A1 | 10/2006 | Wendel et al. | |
| 2007/0215611 A1 | 9/2007 | O'Hagan et al. | |
| 2009/0208614 A1 | 8/2009 | Sharma et al. | |
| 2009/0321428 A1 | 12/2009 | Hyde et al. | |
| 2012/0005992 A1 | 1/2012 | Waldrop et al. | |
| 2012/0018283 A1 | 1/2012 | Dallner et al. | |
| 2013/0240510 A1 | 9/2013 | Kimrey, Jr. | |
| 2013/0240516 A1 | 9/2013 | Kimrey, Jr. | |
| 2013/0243560 A1 | 9/2013 | Kimrey, Jr. et al. | |
| 2014/0083820 A1 | 3/2014 | Mackay | |
| 2016/0029685 A1 | 2/2016 | Tang et al. | |
| 2016/0183333 A1 | 6/2016 | Mohammed et al. | |
| 2017/0027196 A1 | 2/2017 | Resurreccion, Jr. et al. | |
| 2017/0043936 A1 | 2/2017 | Resurreccion, Jr. | |
| 2017/0142785 A1 | 5/2017 | Chang et al. | |
| 2017/0245528 A1 | 8/2017 | Hirschey et al. | |
| 2018/0014559 A1 | 1/2018 | Tang et al. | |
| 2018/0057244 A1 | 3/2018 | Boek et al. | |
| 2018/0111359 A1 | 4/2018 | Komro et al. | |

FOREIGN PATENT DOCUMENTS

| | | |
|---|---|---|
| CN | 106472947 A | 3/2017 |
| CN | 206077729 U | 4/2017 |
| CN | 206077730 U | 4/2017 |
| CN | 106658803 | 5/2017 |
| CN | 106793812 | 5/2017 |
| CN | 206403121 U | 8/2017 |
| CN | 107252030 | 10/2017 |
| CN | 206576184 U | 10/2017 |
| CN | 107535796 A | 1/2018 |
| CN | 206994307 | 2/2018 |
| CN | 207305995 U | 5/2018 |
| EP | 3169141 A1 | 5/2017 |
| EP | 3277496 A1 | 2/2018 |
| EP | 2366268 B1 | 5/2018 |
| GB | 2541373 A | 2/2017 |
| JP | 3211163 U | 6/2017 |
| JP | 2017521111 | 8/2017 |
| JP | 2017532029 | 11/2017 |
| KR | 1020170054433 A | 5/2017 |
| KR | 1020180016081 | 2/2018 |
| KR | 101849847 B | 4/2018 |
| WO | 2006012506 A1 | 2/2006 |
| WO | 2017055501 A1 | 4/2017 |
| WO | 2018017548 A1 | 1/2018 |
| WO | 2018026168 A1 | 2/2018 |
| WO | 2018039112 A1 | 3/2018 |
| WO | 2018063468 A1 | 4/2018 |
| WO | 2018063469 A1 | 4/2018 |
| WO | 2018097355 A1 | 5/2018 |

OTHER PUBLICATIONS

International Search Report and Written Opinion for related PCT Application No. PCT/US2016/055192, dated Jan. 6, 2017; 18 pages.

International Search Report and Written Opinion for related PCT Application No. PCT/US20171054947, dated Dec. 15, 2017; 12 pages.

* cited by examiner

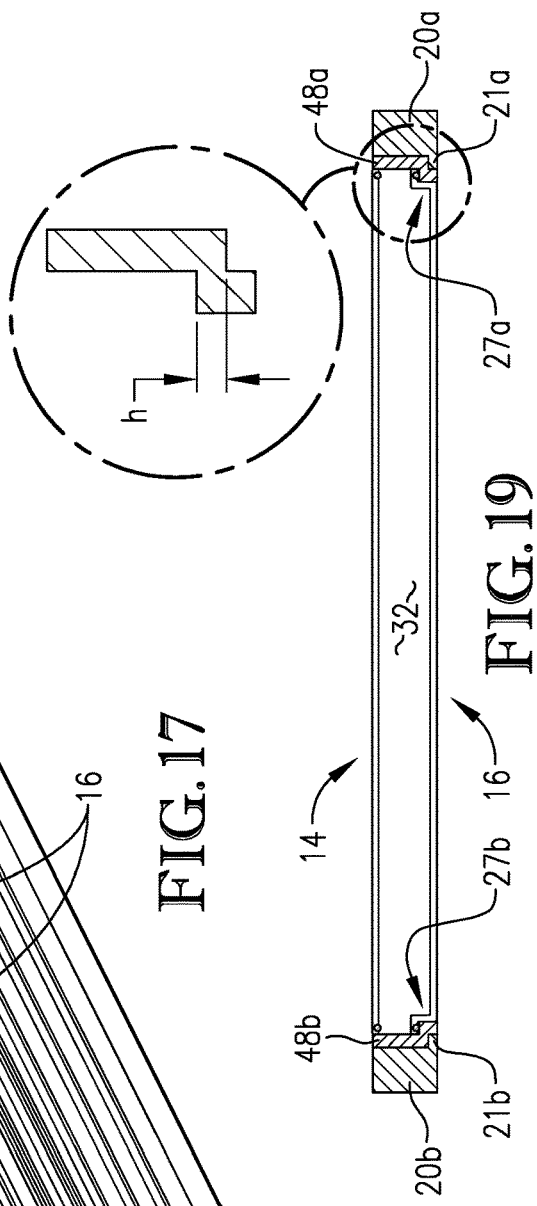
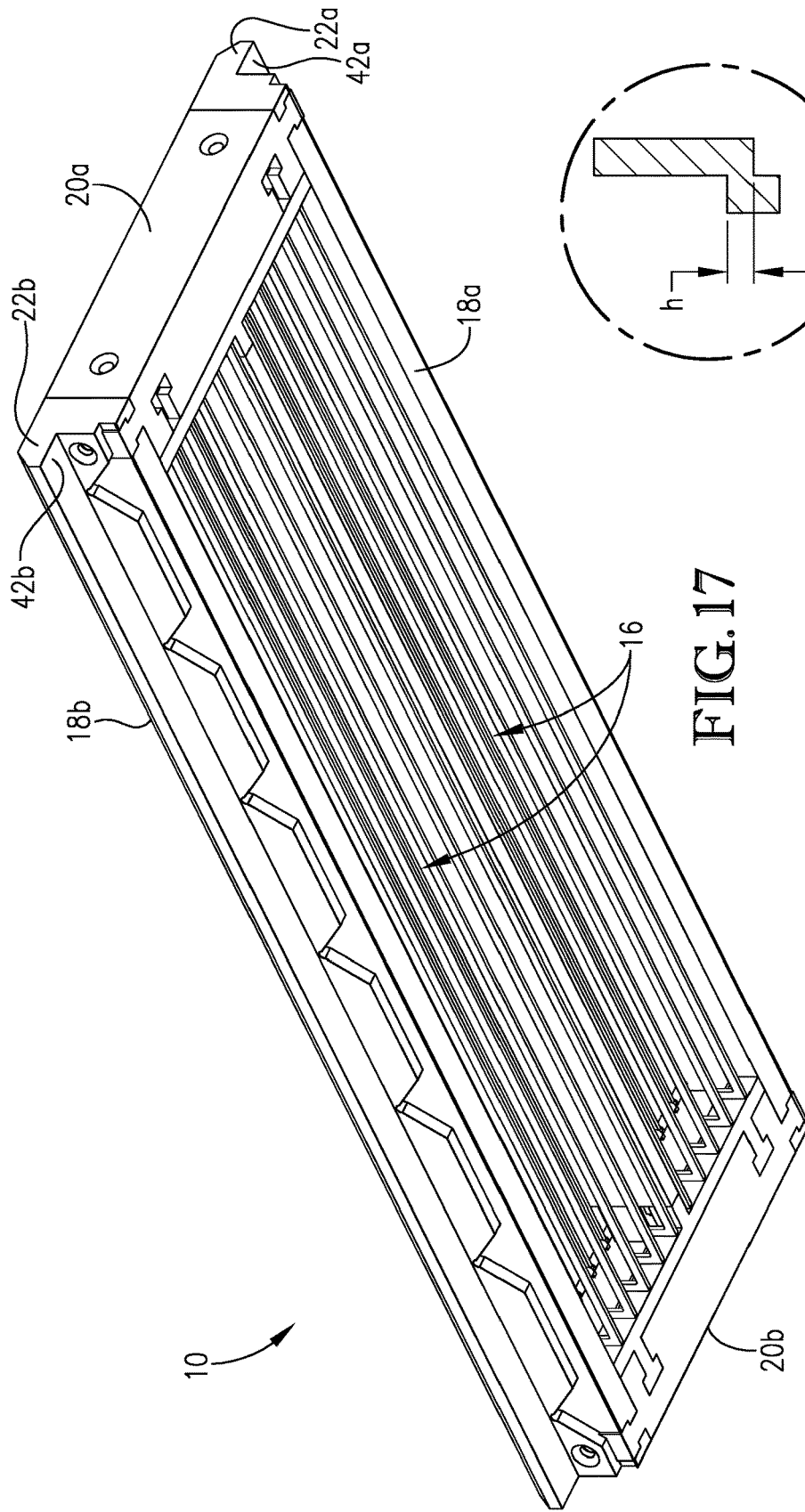
FIG. 17
FIG. 19

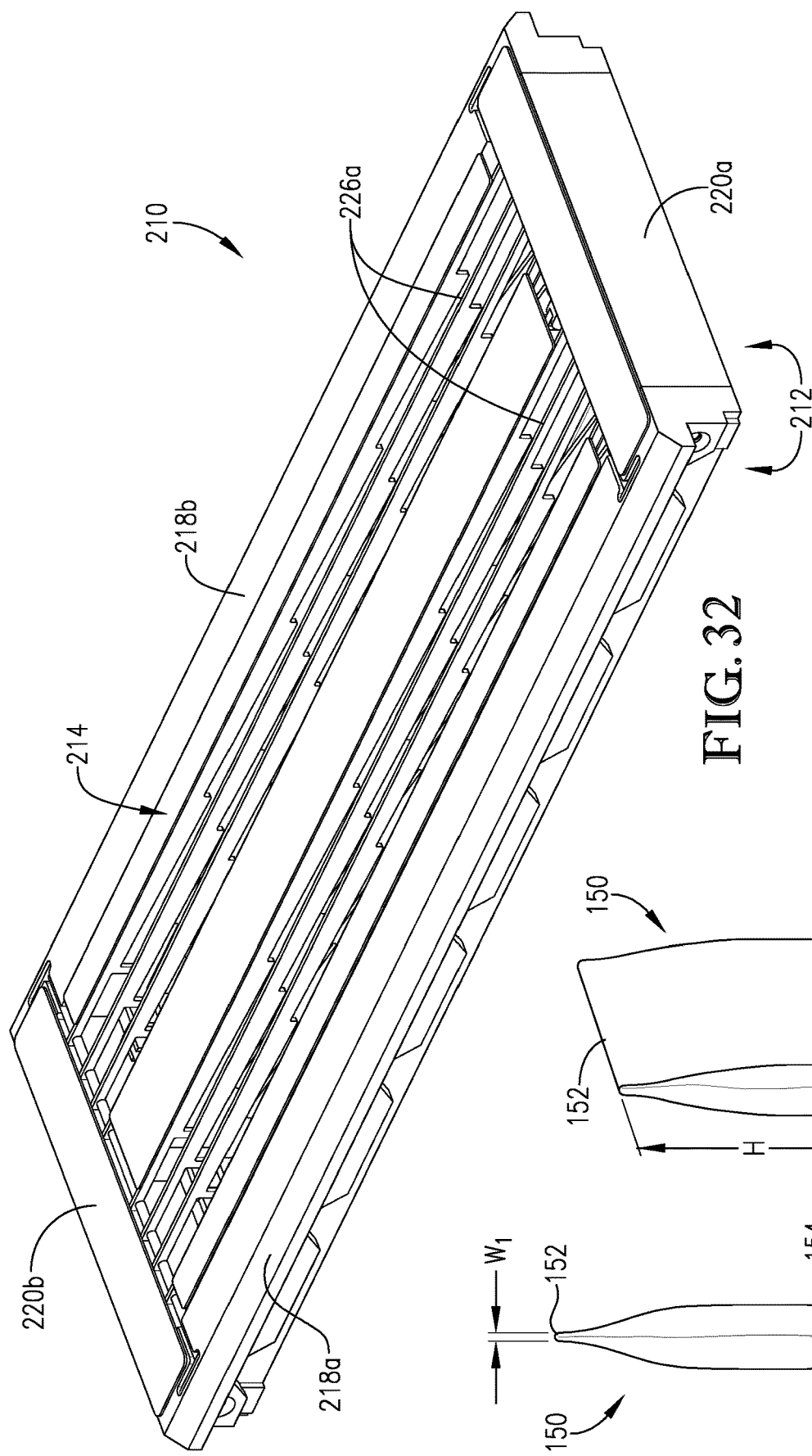
FIG. 32
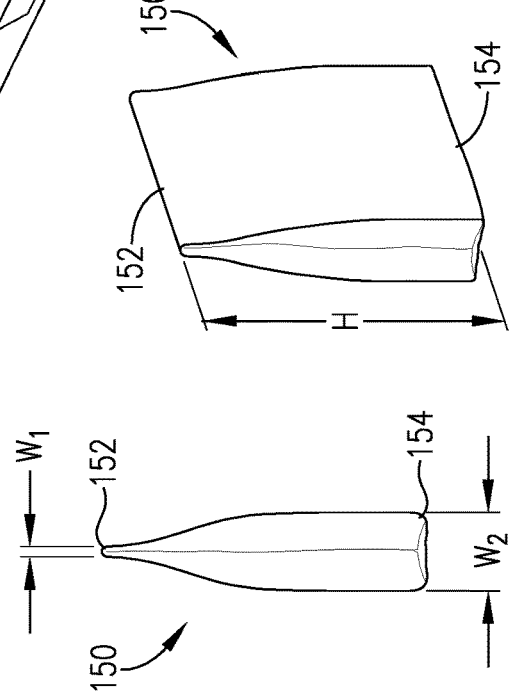
FIG. 31b
FIG. 31a

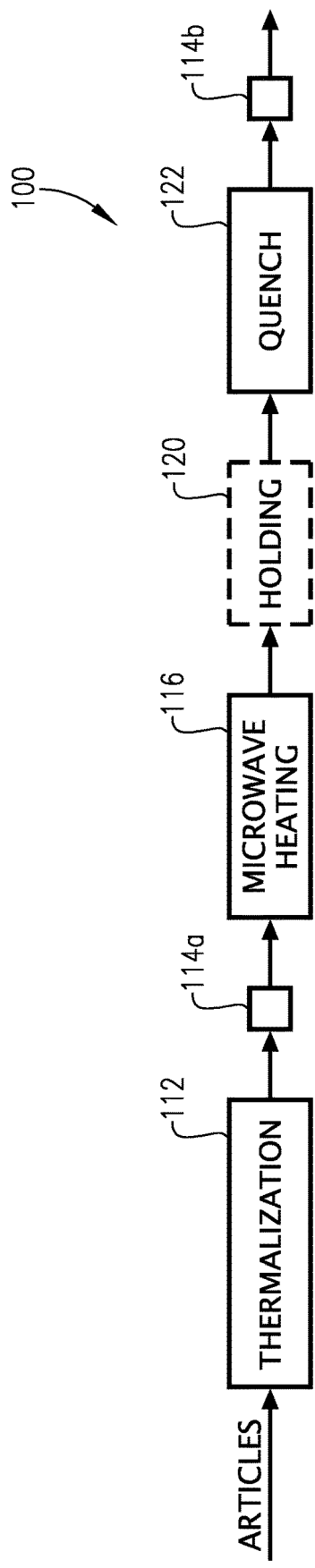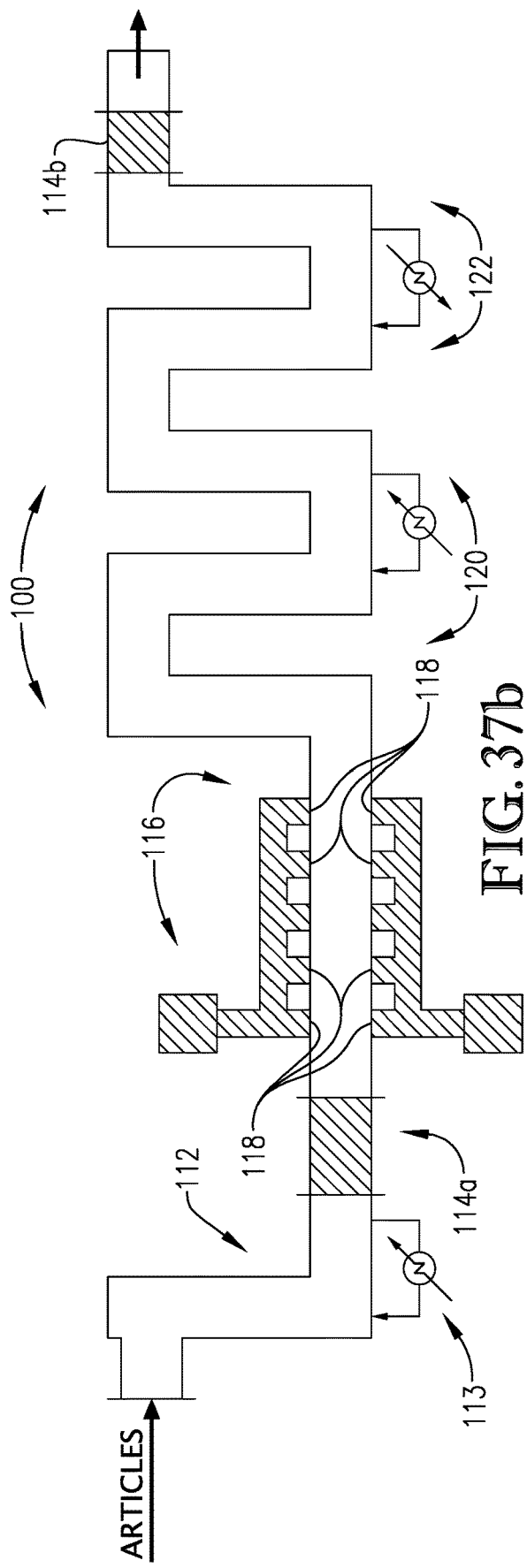

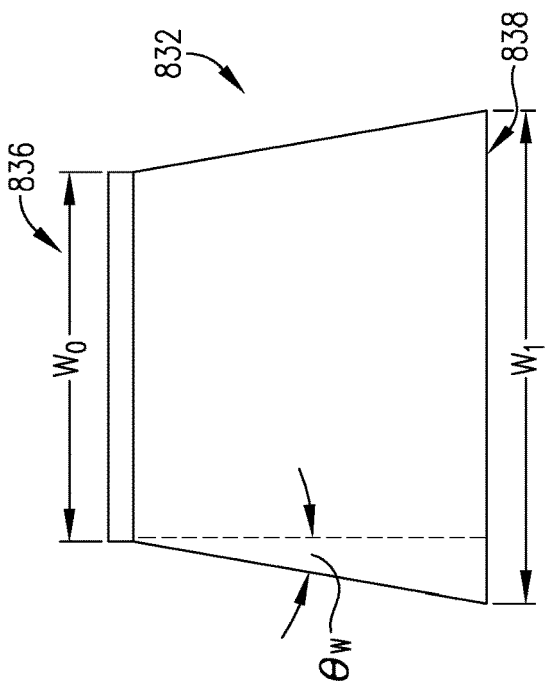
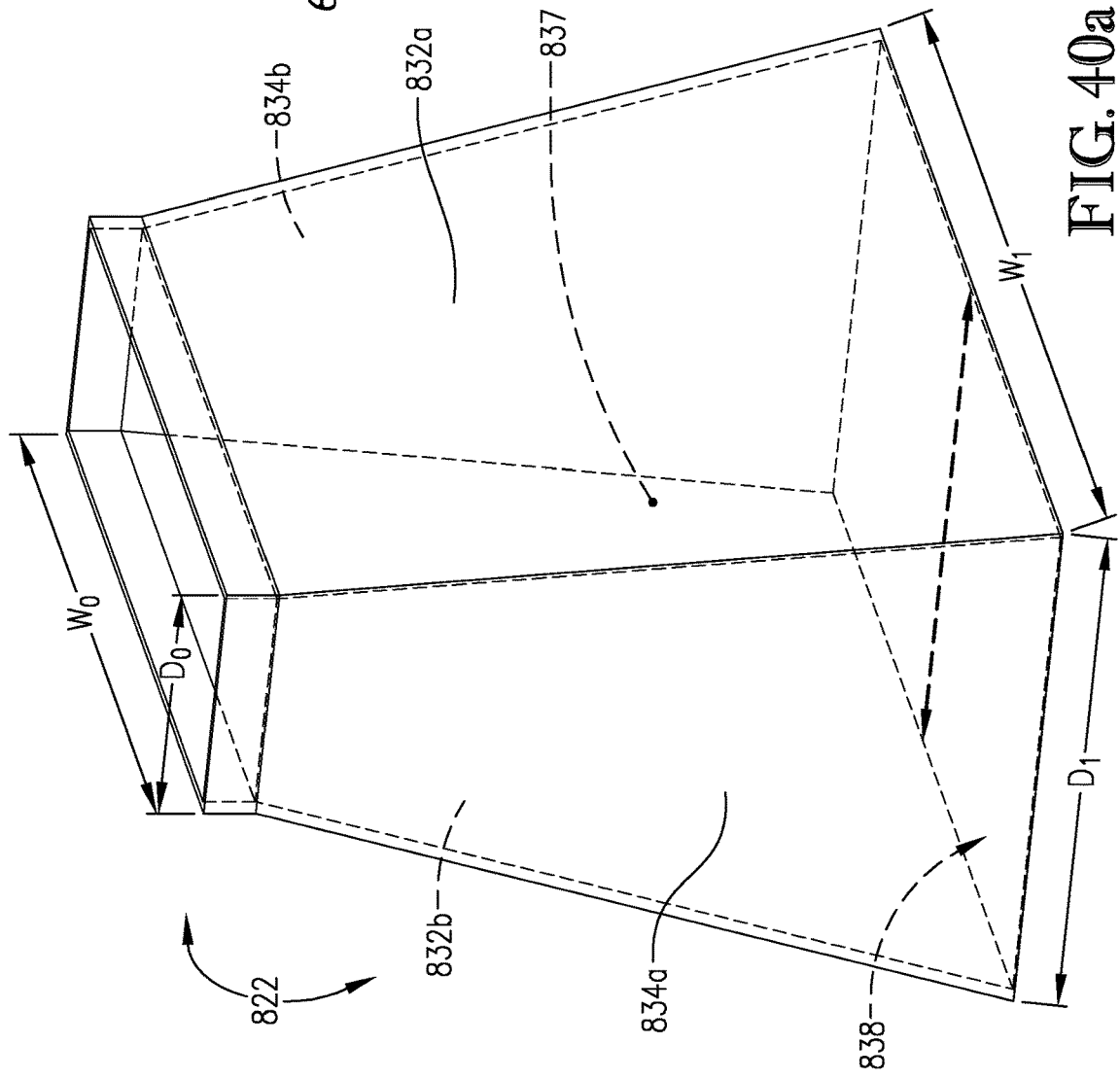

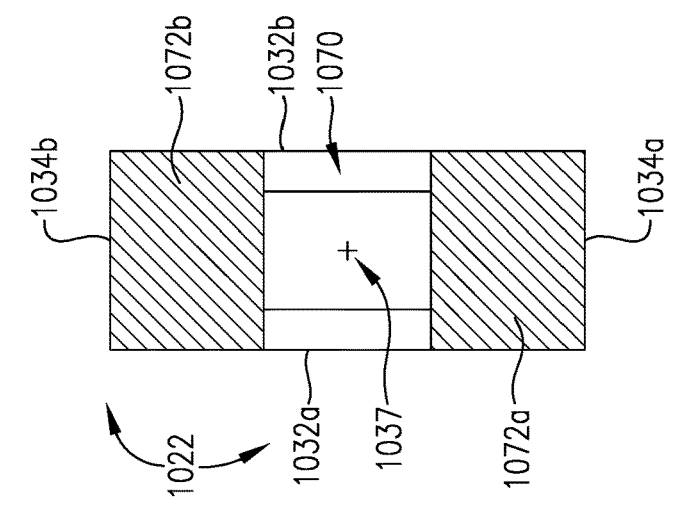
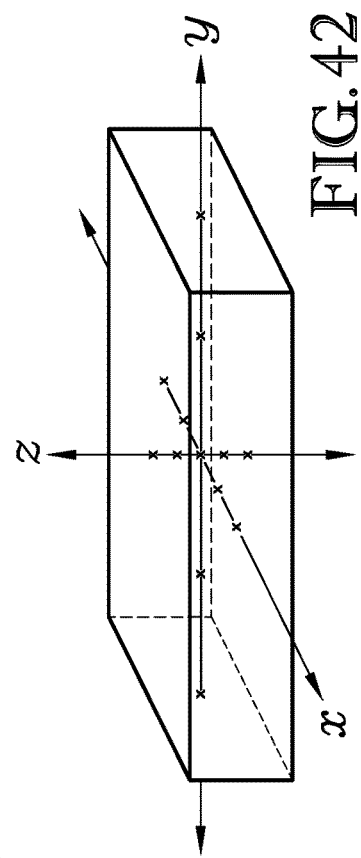
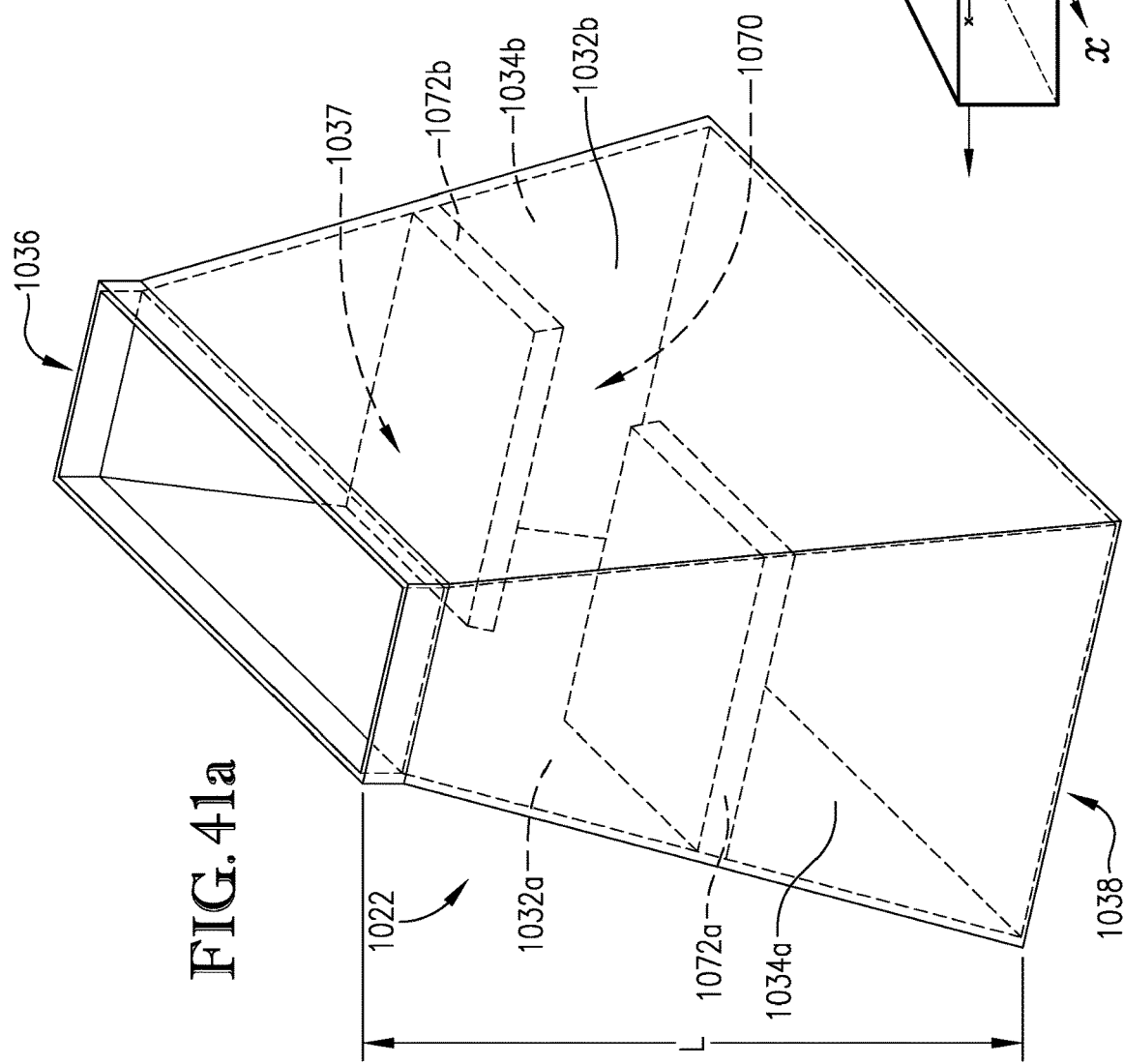

CONVEY LINE CARRIER FOR MICROWAVE HEATING

CROSS-REFERENCE TO RELATED APPLICATIONS

This application claims priority to U.S. Provisional Patent Application No. 62/403,533, filed on Oct. 3, 2016, the disclosure of which is incorporated herein by reference.

FIELD OF THE INVENTION

This invention relates to microwave systems for heating one or more objects, articles, and/or loads. In particular, this invention relates to methods and systems for transporting a plurality of articles through a microwave heating zone.

BACKGROUND

Microwave radiation is a known mechanism for delivering energy to an object. The ability of microwave energy to penetrate and heat an object in a rapid and effective manner has proven advantageous in many chemical and industrial processes. Because of its ability to quickly and thoroughly heat an article, microwave energy has been employed in heating processes wherein the rapid achievement of a prescribed minimum temperature is desired, such as, for example, pasteurization and/or sterilization processes. Further, because microwave energy is generally non-invasive, microwave heating may be particularly useful for heating dielectrically sensitive materials, such as food and pharmaceuticals. However, to date, the complexities and nuances of safely and effectively applying microwave energy, especially on a commercial scale, have severely limited its application in several types of industrial processes.

When microwave energy is applied to the articles as the articles are passed through a liquid-filled, pressurized microwave chamber, the articles may be secured into a carrier to hold the articles in place during heating. In order to achieve desirable commercial throughput, a single microwave system may need a plurality of individual carriers, in order to process the articles in a continuous manner while having sufficient time to load and unload the carriers. Further, if the carriers are designed to process articles of a given size and shape, microwave systems may need several different types of carriers in order to process a wide variety of articles. However, this can greatly increase the operating expenses associated with the system, and may reduce production efficiency by requiring massive change outs of carriers in order to process different types of articles.

Thus, a need exists for an efficient, cost effective industrial-scale microwave heating system capable of achieving consistent results with a wide variety of articles having different sizes and/or shapes. Advantageously, such a system would be easy to operate, while minimizing capital expenses and maximizing throughput.

SUMMARY

One embodiment of the present invention concerns a carrier for transporting a plurality of articles on a convey line of a microwave heating system, wherein each of the articles comprises a pouch having a base and a top, where the base portion is at least twice as thick as the top portion. The carrier comprises a frame comprising first and second spaced apart end members; and an upper support structure and a lower support structure extending between the first and the second end members and configured to secure the articles in the carrier. A pouch receiving space is defined between an upward facing surface of the lower support structure and a downward facing surface of the upper support structure. The downward facing surface and/or the upward facing surface comprises a series of recesses and each of the recesses is configured to receive the base portion of one of the pouches so as to secure the pouch in the pouch receiving space.

Another embodiment of the present invention concerns a carrier and article system for transporting a plurality of articles on a convey line of a microwave heating system. The carrier and article system comprises a frame comprising first and second spaced apart side members configured to engage the convey line and first and second spaced apart end members coupled to and extending between opposite ends of the first and second side members and an upper support structure and a lower support structure for securing the articles in the carrier, wherein the upper and lower groups of support members are configured to extend between the first and second end members. A pouch receiving space is defined between an upward facing surface of the lower support structure and a downward facing surface of the upper support structure. The carrier and article system further comprises a plurality of pouches loaded into the pouch receiving space, wherein each of the articles comprises a pouch having a base and a top, where the base portion is at least twice as thick as the top portion, wherein the pouches are arranged in the pouch receiving space in an overlapping configuration, with the top of one pouch at least partially overlapping the base of an adjacent pouch.

Yet another embodiment of the present invention concerns a method for sterilizing or pasteurizing pouches containing at least one consumable item. The method comprises the steps of providing a carrier having a pouch receiving space and loading a plurality of pouches into the pouch receiving space in an overlapping configuration, with a narrow top portion of each of the pouches overlapping with a broader base portion of an adjacent pouch. The method also comprises passing the carrier and pouches through a heating zone, and during the passing, using microwave energy to heat the pouches to a temperature sufficient to sterilize or pasteurize the consumable item.

Still another embodiment of the present invention concerns a carrier and article system for transporting a plurality of articles on a convey line of a microwave heating system. The carrier and article system comprises a frame comprising first and second spaced apart side members configured to engage the convey line and first and second spaced apart end members coupled to and extending between opposite ends of the first and second side members. The carrier and article system also comprises an upper support structure and a lower support structure for securing the articles in the carrier. The upper and lower support structures extend between the first and second spaced apart end members to thereby define a cargo volume. The carrier and article system further comprises a plurality of articles received in the cargo volume. At least two of the articles in the cargo volume are arranged in an overlapped configuration such that at least a portion of one article is positioned directly above at least a portion of an adjacent article.

BRIEF DESCRIPTION OF THE DRAWINGS

Various embodiments of the present invention are described in detail below with reference to the attached drawing Figures, wherein:

FIG. 17 is a bottom front isometric view of the carrier shown in FIG. 16;

FIG. 19 is a longitudinal cross sectional view of the carrier shown in FIGS. 16-18;

FIG. 31a is a side view of a pouch suitable for use in carriers according to embodiments of the present invention, particularly illustrating one example of a pouch having a base portion that is at least twice as wide as its top portion;

FIG. 31b is an isometric view of the pouch shown in FIG. 31a;

FIG. 32 is a top front isometric view of a carrier configured to hold a plurality of pouches according to one or more embodiments of the present invention;

FIG. 37a is process flow diagram depicting one embodiment of a microwave heating system for heating one or more articles, particularly illustrating a system comprising a thermalization zone, a microwave heating zone, an optional holding zone, a quench zone, and a pair of pressure adjustment zones;

FIG. 37b is a schematic diagram of a microwave heating system 110 configured according to one embodiment of the present invention, particularly each of the zones of microwave heating system 110 outlined in the diagram provided in FIG. 37a;

FIG. 40a is an isometric view of a microwave launcher configured according to one embodiment of the present invention;

FIG. 40b is a longitudinal side view of the microwave launcher depicted in FIG. 39a;

FIG. 41a is an isometric view of a microwave launcher configured according to yet another embodiment of the present invention, particularly showing an integrated inductive iris disposed between the inlet and outlet of the launcher;

FIG. 41b is a horizontal cross sectional view of the microwave launcher depicted in FIG. 41a; and FIG. 42 is an isometric depiction of the location of thermocouples inserted into a test package to determine the minimum temperature of the package for determining the heating profile of for an article according to one embodiment of the present invention.

DETAILED DESCRIPTION

Figure 1:
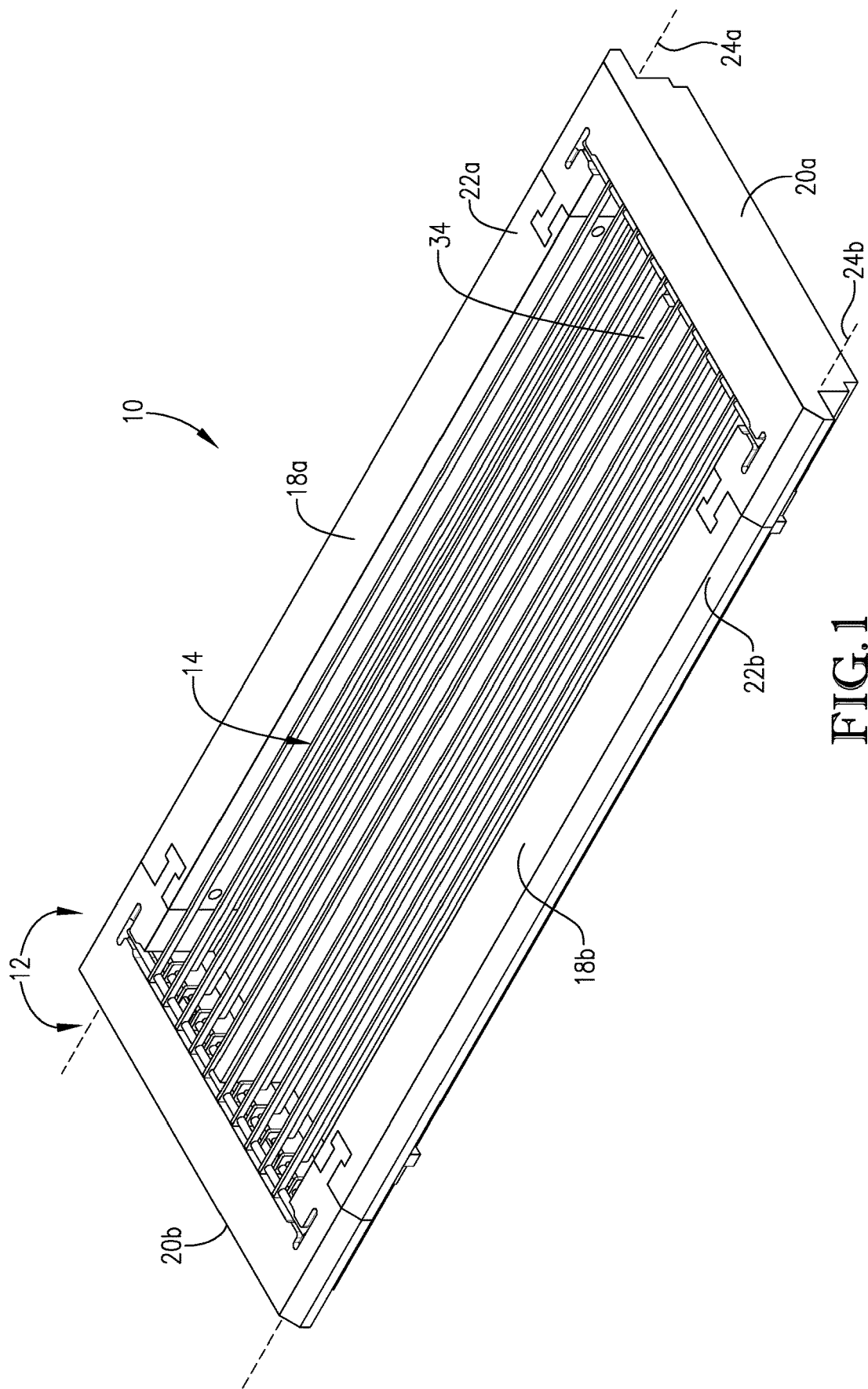
FIG. 1 is a top front isometric view of a carrier configured according to one or more embodiments of the present invention.

The present invention relates to processes and systems for heating a plurality of articles in a microwave heating system. More particularly, embodiments of the present invention relate to carriers for transporting a plurality of articles through a microwave heating zone and to methods of loading such carriers in order to provide uniform heating to each of the articles. Suitable types of articles can include, but are not limited to, packaged foodstuffs, medical liquids, pharmaceuticals, and medical or dental instruments. Additionally, the processes and systems of the present invention may be utilized to process articles having different sizes, shapes, and packaging designs in a manner that provides consistent and efficient microwave-assisted pasteurization and/or sterilization of the articles.

Microwave heating systems as described herein may be any heating system that uses microwave energy to heat the articles passing therethrough. In some embodiments, the microwave heating system may include a liquid-filled, pressurized microwave heating chamber and the articles may be at least partially, or completely, submerged during heating. Carriers according to embodiments of the present invention are configured to secure a plurality of articles in place as the articles are passed through the microwave heating zone. As a result, the articles are exposed to a more controlled, more uniform microwave field, which ensures sufficient and adequate heating of each article to a temperature of between about 80° C. and about 100° C. for pasteurization or between about 100° C. to about 140° C. for sterilization. Specific embodiments of microwave heating systems suitable for use with the present invention are described in detail below.

It has been discovered that a carrier employing multiple, spaced apart, electrically conductive slats on one or both sides of the articles being heated can provide unexpected benefits. Traditionally, use of electrically conductive material in microwave zones has been specifically avoided in order to avoid arcing and other such problems, but it has been found that the use of properly configured electrically conductive slats can actually increase the uniformity of the microwave field to which the articles positioned in the carrier are exposed. Additionally, the ability to use electrically conductive materials in a carrier may help permit a wider selection of strong, relatively rigid, and affordable food-grade materials to be used in constructing the carrier. With this wide range of materials to choose from, carriers can be made larger and more durable for increased efficiency on a commercial-scale. Furthermore, it has been discovered that carriers that include one or more removable article spacing members may also provide enhanced process flexibility by permitting adjustment of the size and/or shape of the article-containing cargo volume within the carrier. As a result, a single carrier can be selectively configured to process several different types of articles having varying sizes and/or shapes.

Figure 2:
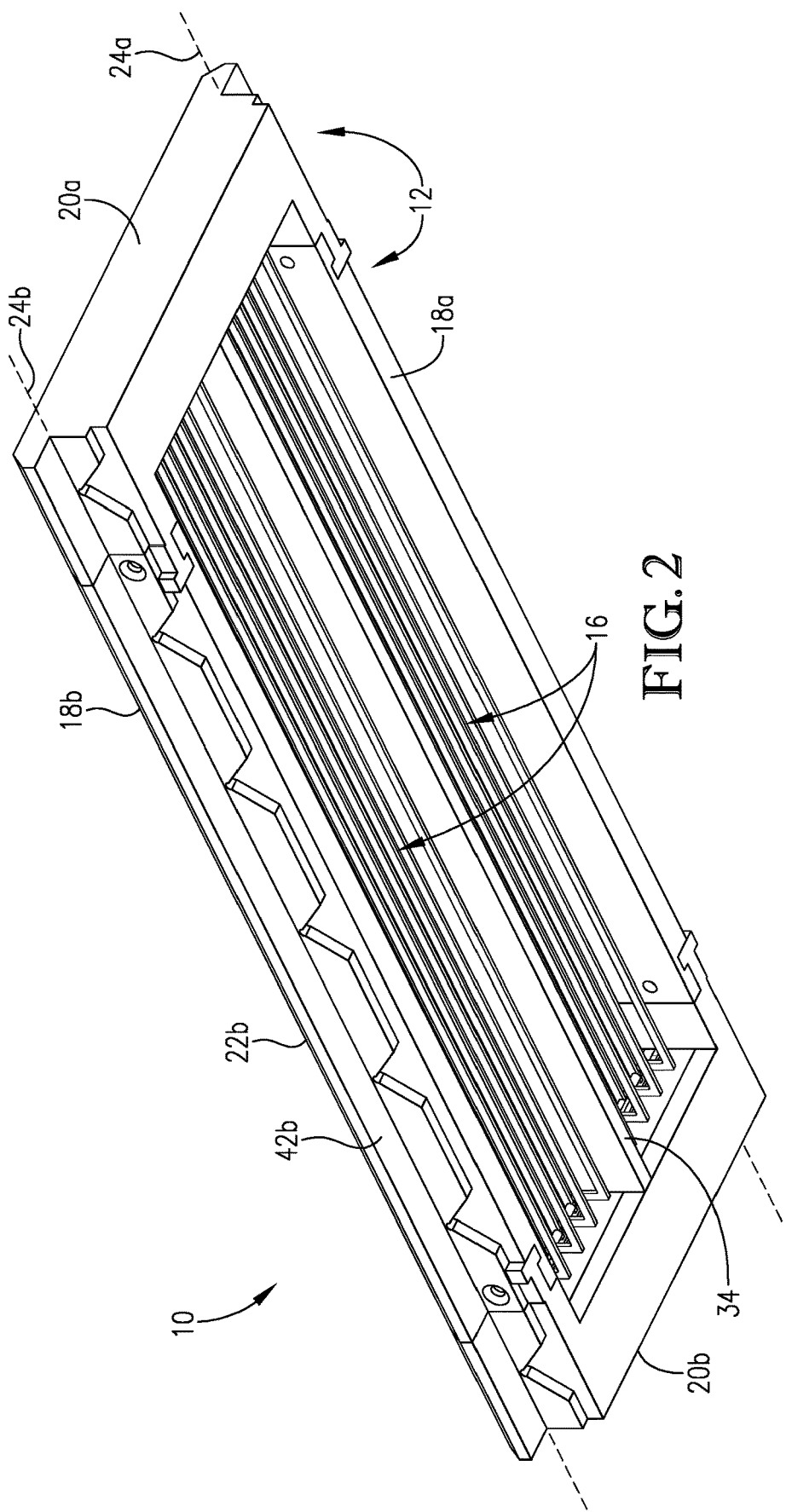
FIG. 2 is a bottom front isometric view of the carrier shown in FIG. 1.
Figure 3:
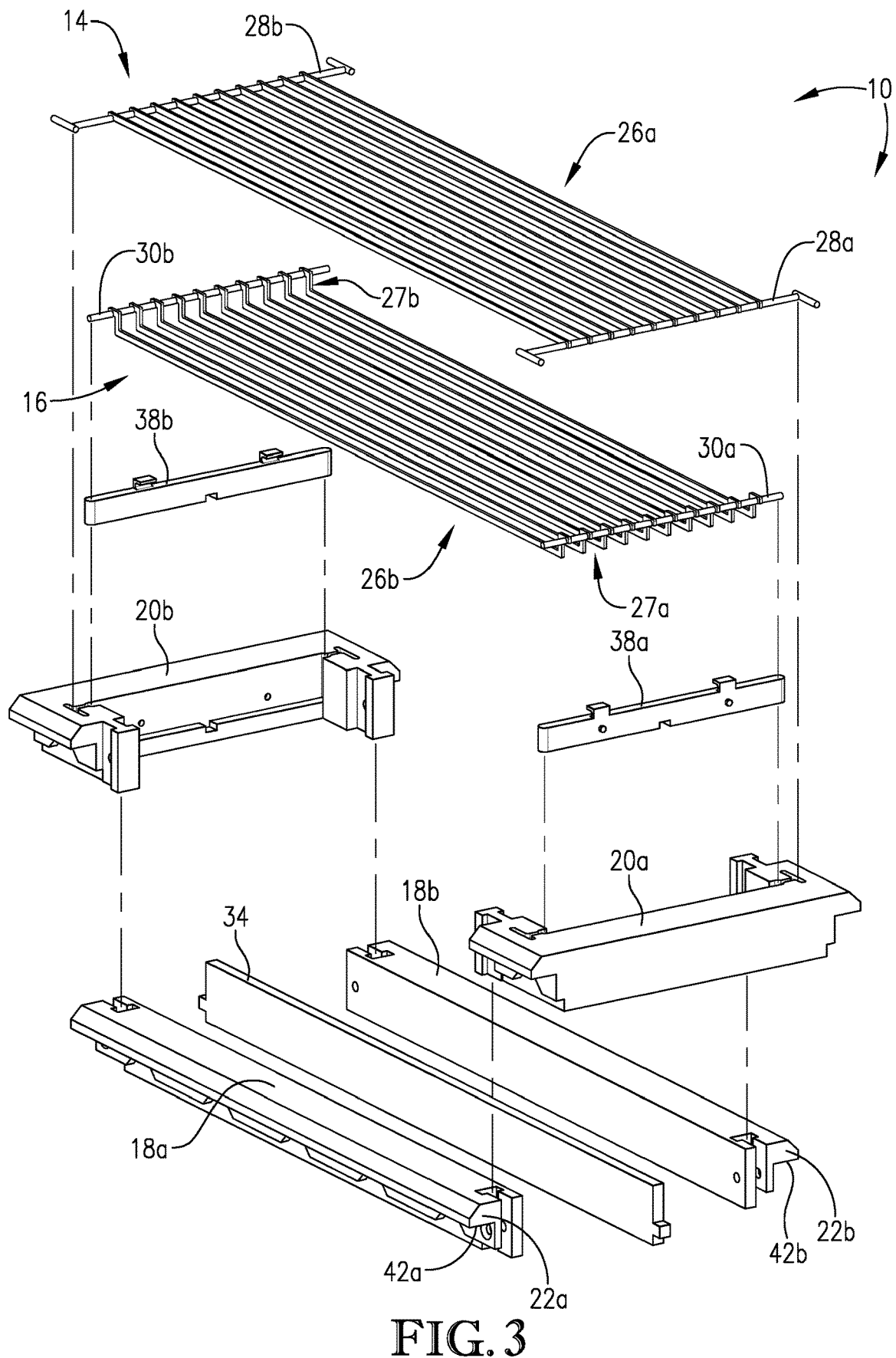
FIG. 3 is an exploded view of the carrier shown in FIGS. 1 and 2.
Figure 4:
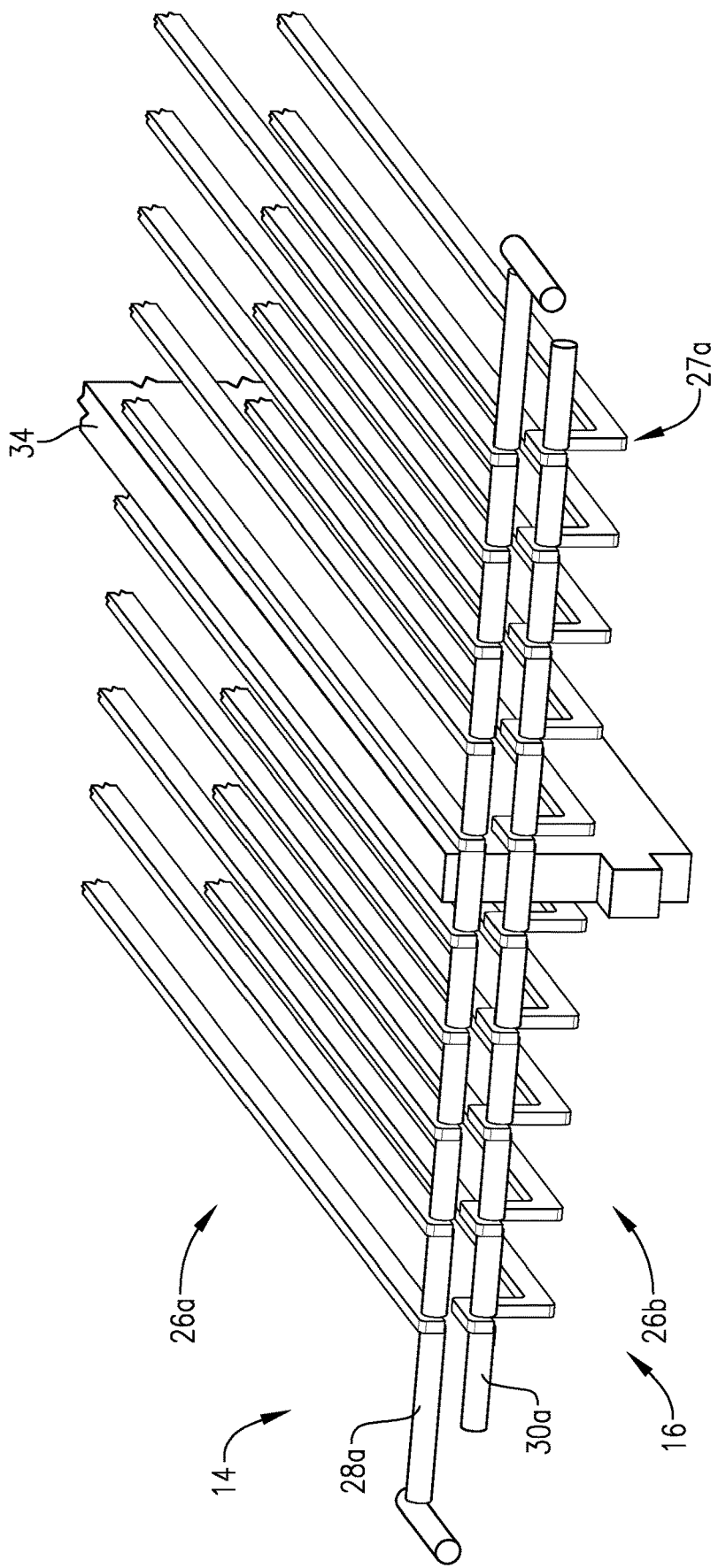
FIG. 4 is a partial front isometric view of upper and lower support structures suitable for use in the carrier shown in FIGS. 1-3.

Turning initially to FIGS. 1-4, a carrier 10 configured according to one or more embodiments of the present invention is shown. As illustrated in FIGS. 1-3, carrier 10 includes an outer frame 12, an upper support structure 14, and a lower support structure 16. As shown in FIGS. 1-3, outer frame 12 comprises two spaced-apart side members 18a,b and two spaced-apart end members 20a,b. First and second end members 20a,b may be coupled to and extend between opposite ends of first and second side members 18a,b to form outer frame 12, which can have a generally rectangular shape. First and second side members 18a,b include respective support projections 22a,b that are configured to engage respective first and second convey line support members of a convey line, represented by dashed lines 24a and 24b in FIGS. 1 and 2, respectively. First and second support projections 22a,b of carrier 10 present respective first and second lower support surfaces 42a,b for supporting carrier 10 on first and second convey line support members 24a,b. Convey line support members 24a,b may be moving convey line members and can, for example, include two chains located on each side of carrier 10.

Figure 16:
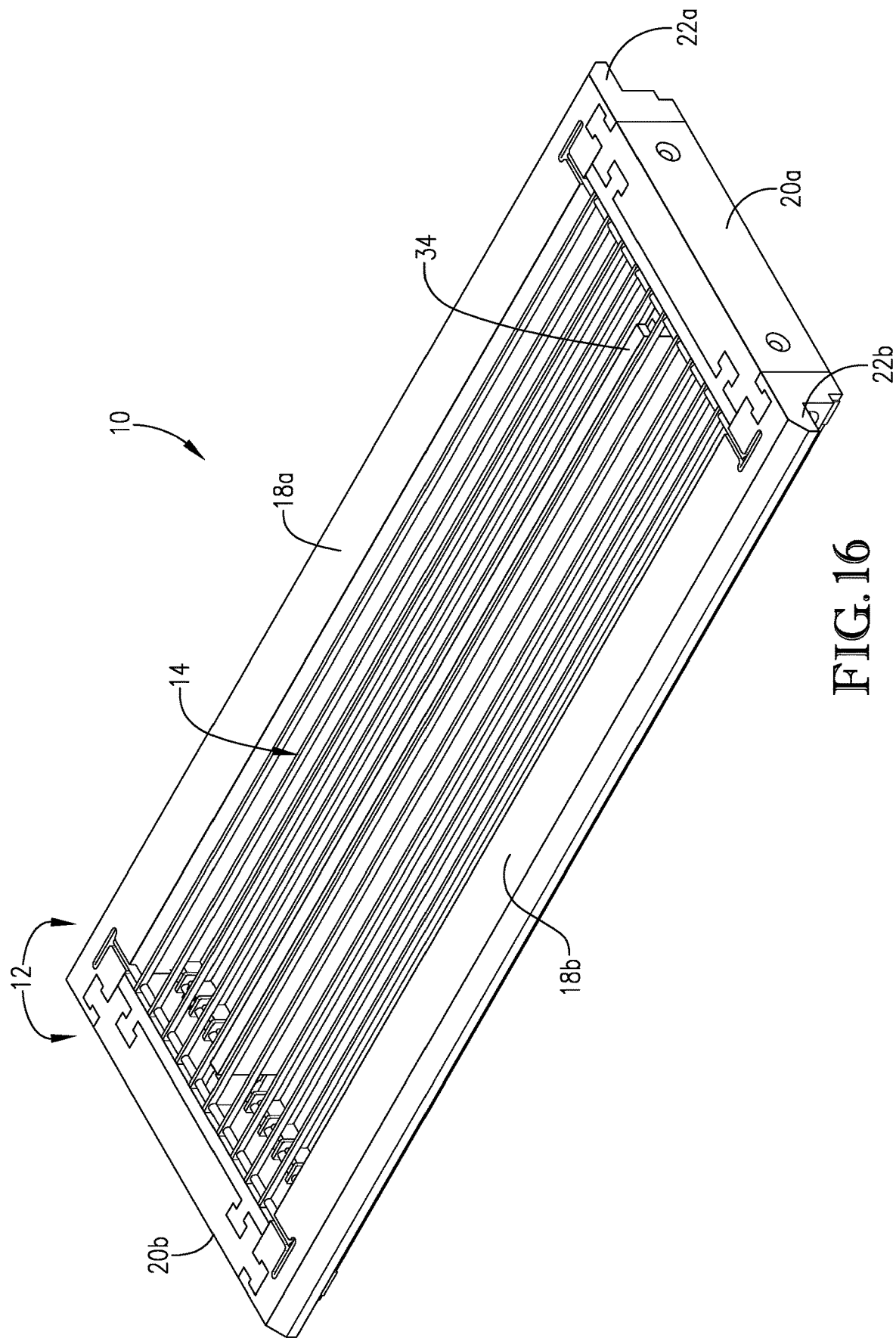
FIG. 16 is a top front isometric view of another carrier configured according to one or more embodiments of the present invention.
Figure 18:
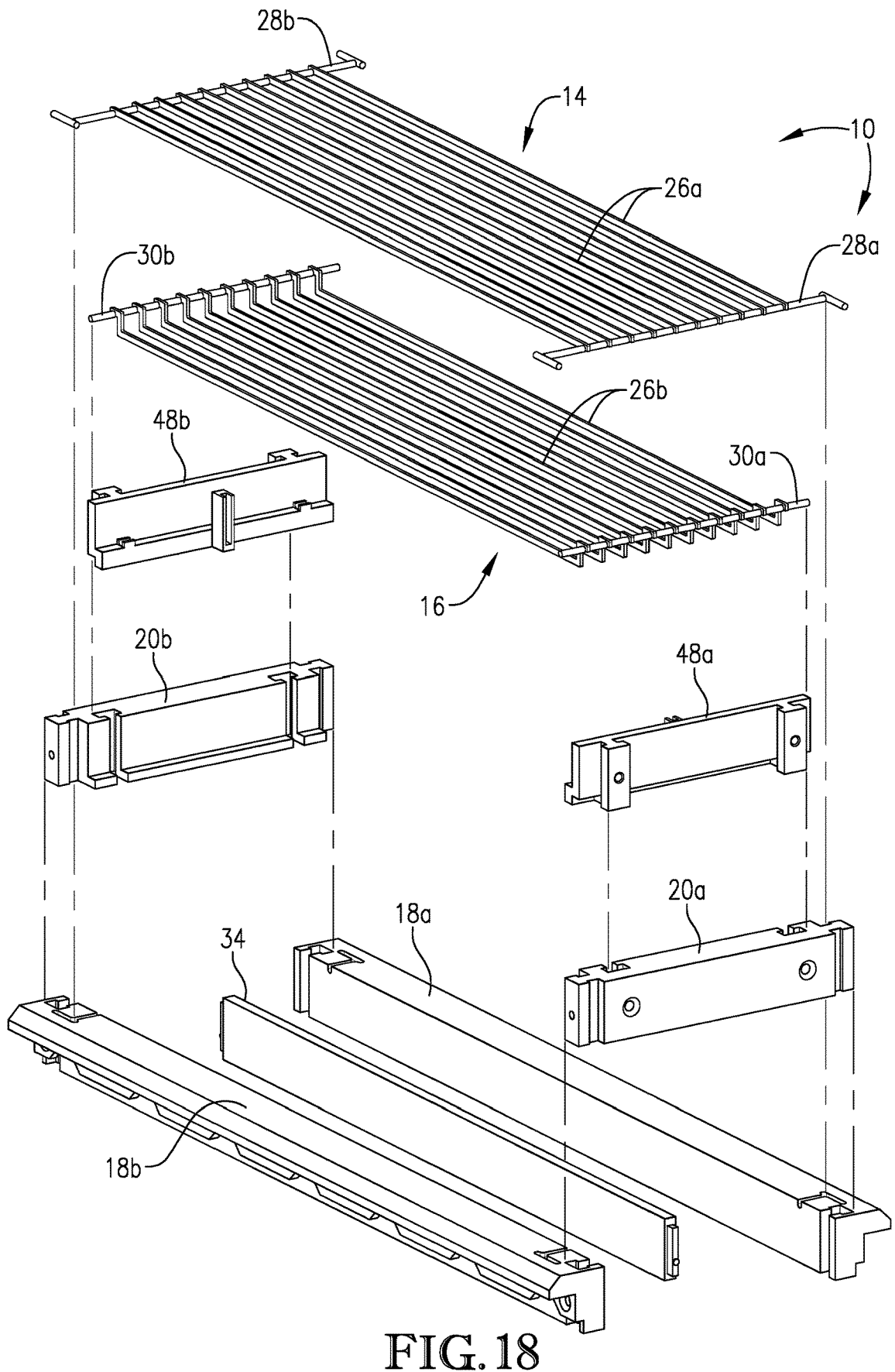
FIG. 18 is an exploded view of the carrier shown in FIGS. 16 and 17.

Turning now to FIGS. 16-19, another embodiment of carrier 10 is provided. Carrier 10 shown in FIGS. 16-19 includes outer frame 12, an upper support structure 14, and a lower support structure 16 configured in a similar manner as described previously with respect to FIGS. 1-4. As shown in FIGS. 16-19, outer frame 12 comprises two spaced-apart side members 18a,b and two spaced-apart end members 20a,b, and first and second end members 20a,b may be coupled to and extend between opposite ends of first and second side members 18a,b to form outer frame 12. As shown in FIGS. 16-18, first and second side members 18a,b may extend the entire length of carrier 10, while in the embodiments depicted in FIGS. 1-3, first and second side members 18a,b may only extend along a portion of the total length of carrier 10. For example, in some embodiments, side members 18a,b may extend at least about 65, at least about 70, at least about 75, at least about 80, at least about 85, at least about 90, or at least about 95 percent of the total length of carrier 10, depending on the size and configuration of end members 20a,b.

First and second side members 18a,b and first and second end members 20a,b of frame 12 may be formed of any suitable material and, in some embodiments, are formed of a low loss tangent material. In some embodiments, the low loss tangent material used to form one or more of first and second side members 18a,b and/or first and second end members 20a,b can have a loss tangent of not more than about $10^{-4}$, not more than about $10^{-3}$, not more than about $10^{-2}$, measured at 20° C. Examples of suitable low loss tangent materials may include various polymers and ceramics. In some embodiments, the low loss tangent material may be a food-grade material.

When a polymer is used as the low loss tangent material, the polymer may have a glass transition temperature ($T_g$) of at least about 80° C., at least about 100° C., at least about 120° C., or at least about 140° C., in order to withstand the elevated temperatures to which the carrier may be exposed during heating of the articles. Suitable polymers can include, for example, polytetrafluoroethylene (PTFE), polysulfone, polynorbornene, polycarbonate (PC), acrylonitrile butadiene styrene (ABS), poly(methyl methacrylate) (PMMA), polyetherimide (PEI), polystyrene, polyvinyl alcohol (PVA), polyvinyl chloride (PVC), and combinations thereof. The polymer can be monolithic or it may be reinforced with glass fibers. In certain embodiments, glass-filled PTFE ("Teflon") may be used as the low loss tangent material for forming outer frame 12. When a ceramic is used as the low loss tangent material, the ceramic can comprise an aluminosilicate. In some embodiments, an oxide ceramic, such as aluminum oxide, can be used as the low loss tangent material. In some embodiments, each of first and second side members 18a,b and each of first and second end members 20a,b may be formed of the same material, while, in other embodiments, at least one of first side member 18a, second side member 18b, first end member 20a, and second end member 20b may be formed of a different material.

Referring again to the embodiments of carrier 10 shown in FIGS. 1-4 and 16-19, upper and lower support structures 14, 16 of carrier 10 each include a plurality of support members extending between first and second end members 20a,b in a direction generally parallel to one another. Although shown as including individual support members, it should be understood that upper and/or lower support structures 14, 16 could include an upper and lower grid member, or it could include sheets of microwave-transparent or microwave semi-transparent material extending between first and second end members 20a,b. Combinations of one or more of the above are also possible. Upper and lower support structures 14, 16 may include any type of support structure suitable for retaining the articles within carrier 10 while permitting microwave energy to reach the articles.

When upper and/or lower support structures 14, 16 include individual support members, as shown in FIGS. 1-4 and 16-19, the each support member may extend in a direction substantially perpendicular to first and second end members 20a,b and substantially parallel to first and second side members 18a,b. As used herein, the terms "substantially parallel" and "substantially perpendicular" mean within 5° of being parallel or perpendicular, respectively. In total, carrier 10 may include at least about 8, at least about 12, at least about 20, or at least about 24 individual support members and/or not more than about 100, not more than about 80, not more than about 60, not more than about 50, or not more than about 40 individual support members, or the total number of individual support members in carrier 10 may be in the range of from 8 to about 100, from about 12 to about 80, from about 20 to about 60, or from about 24 to about 50.

In some embodiments, upper support structure 14 may include an upper group of individual support members 26a and lower support structure 16 may include a lower group of individual support members 26b. As particularly illustrated in FIGS. 3 and 18, the individual support members in upper and lower groups of support members 26a,b may be rigidly fixed to a pair of respective transverse cross members 28a,b and 30a,b located at opposite ends in order to maintain the position of the support members relative to one another. As particularly illustrated in FIGS. 3 and 4, the upper group of support members 26a may be substantially straight, while the lower group of support members 26b may include an angled portion 27a,b at each end of the support member that may be coupled to transverse cross members 30a,b. Such angled portions 27a,b may help facilitate additional spacing between the upper and lower support structures 14, 16 when carrier 10 is assembled. In some embodiments (not shown), individual support members in upper group of support members 26a may include an angled portion, while the support members in lower group 26b may be substantially straight. In some embodiments, the individual support members in each of the upper and lower groups 26a,b may be substantially straight, while, in other embodiments, the individual support members in each of the upper and lower groups 26a,b may include an angled portion.

Each of upper and lower groups of support members 26a,b shown in FIGS. 1-4 and 16-19 may include any number of individual support members. In some embodiments, the total number of individual support members in each of the upper and lower groups of support members 26a,b can be at least about 4, at least about 6, or at least about 10 and/or not more than about 50, not more than about 40, or not more than about 30, or the total number of individual support members in each of upper and lower groups of support members 26a,b can be in the range of from 4 to 50, from 6 to 40, or from 10 to 30. Each of upper and lower groups of support members 26a,b may include an equal number of support members, or one of upper and lower groups of support members 26a,b may include more support members than the other.

The individual support members within upper and lower groups 26a,b can be configured in any suitable pattern. In some embodiments, the individual support members in at least one of upper group 26a and lower group 26b may be substantially equally spaced from one another. Alternatively, or in addition, the individual support members within one or both of upper and lower groups 26a,b may be unequally spaced. The individual support members in upper group 26a may have the same spacing as, or different spacing than, the support members in lower group 26b. In some embodiments, the average center-to-center spacing between individual support members of upper group of support members 26a and/or lower group of support members 26b can be at least about 0.1, at least about 0.25, at least about 0.5, or at least about 0.75 inches and/or not more than about 10, not more than about 5, not more than about 2.5, or not more than about 2 inches, or it can be in the range of from about 0.1 to 10, from about 0.25 to 5, from about 0.5 to 2.5, or from about 0.75 to 2 inches.

The individual support members in each of upper and lower groups 26a,b may be formed of a strong, electrically conductive material. In some embodiments, the material may be a food-grade material. The electrically conductive material from which the individual support members (and, optionally, transverse cross members) are formed can have a conductivity of at least about $10^3$, at least about $10^4$, at least about $10^5$, at least about $10^6$, or at least about $10^7$ Siemens per meter (S/m) at 20° C., measured according to ASTM E1004 (09). Additionally, the electrically conductive material from which the individual support members are formed may have a tensile strength of at least about 50, at least about 100, at least about 200, at least about 400, or at least about 600 MegaPascals (MPa), measured according to ASTM E8/E8M-16a. The electrically conductive material may also have a yield strength of at least about 50, at least about 100, at least about 200, at least about 300, or at least about 400 MPa at 20° C., measured according to ASTM E8/E8M-16a. The Young's Modulus of the electrically conductive material can be at least about 25, at least about 50, at least about 100, or at least about 150 GigaPascals (GPa) and/or not more than about 1000, not more than about 750, not more than about 500, or not more than about 250 GPa, measured at 20° C., or it can be in the range of from about 25 to about 1000, about 50 to about 750, about 100 to about 500, or about 150 to about 250 GPa. Young's Modulus is measured according to ASTM E111-04 (2010).

The electrically conductive material from which the individual support members are formed may be metallic. In some embodiments, the electrically conductive material may be a metal alloy. The metal alloy may comprise, for example, iron and chromium, with the iron being present in a higher amount than the chromium. In some embodiments, the iron may be present in an amount of at least about 40, at least about 50, or at least about 60 weight percent and/or not more than about 95, not more than about 90, or not more than about 85 weight percent, and the chromium may be present in an amount of at least about 5, at least about 8, or at least about 10 weight percent and/or not more than about 40, not more than about 35, or not more than about 30 weight percent. Iron may be present in an amount in the range of from about 40 to about 95 weight percent, from about 50 to about 90 weight percent, or from about 60 to about 85 weight percent and chromium may be present in an amount in the range of from about 5 to about 40 weight percent, from about 8 to about 35 weight percent, or from about 10 to about 30 weight percent.

In some embodiments, the metal alloy may further comprise nickel. When present, the amount of nickel in the metal alloy may be at least about 1, at least about 2, or at least about 4 and/or not more than about 30, not more than about 20, or not more than about 15 weight percent, or it may be in the range of from about 1 to about 40 weight percent, from about 2 to about 35 weight percent, or from about 4 to about 30 weight percent. When the metal alloy comprises iron, nickel, and chromium, iron may be present in an amount in the range of from about 40 to about 95 weight percent, from about 50 to about 90 weight percent, or from about 60 to about 85 weight percent, the chromium may be present in an amount in the range of from about 5 to about 40 weight percent, from about 8 to about 35 weight percent, or from about 10 to about 30 weight percent, and the nickel may be present in an amount in the range of from about 1 to about 40, from about 2 to about 35, or from about 4 to about 30 weight percent. The metallic alloy may be stainless steel.

When upper and/or lower support structures 14, 16 include a plurality of individual support members, the support members may have many of suitable shapes. For example, in some embodiments, the individual support members in upper and/or lower groups of support members 26a,b may comprise slats having a generally rectangular transverse cross section. Each slat can have an average cross sectional area of at least about 0.001, at least about 0.005, at least about 0.01, or at least about 0.025 square inches (in$^2$) and/or not more than about 1, not more than about 0.5, not more than about 0.25, or not more than about 0.1 in$^2$, or it can be in the range of from about 0.001 to about 1 in$^2$, from about 0.005 to about 0.5 in$^2$, from about 0.01 to about 0.25 in$^2$, or from about 0.025 to about 0.1 in$^2$. Additionally, each of the slats in the upper and/or lower group of support members can have a length-to-diameter ratio of at least about 5:1, at least about 10:1, or at least about 20:1 and/or not more than about 500:1, not more than about 250:1, or not more than about 100:1, where the diameter of the slat is measured as the length of the longest straight line extending edge-to-edge through the center of a transverse cross section of the slat. The length-to-diameter ratio of each of the slats can be in the range of from about 5:1 to about 500:1, about 10:1 to about 250:1, or about 20:1 to about 100:1.

The ratio of the height of each slat to its width can be at least about 0.5:1, at least about 1:1, at least about 1.5:1 and/or not more than about 10:1, not more than about 6:1, or not more than about 4:1, or it can be in the range of from about 0.5:1 to about 10:1, from about 1:1 to about 6:1, or from about 1.5:1 to about 4:1. The average height of each slat can be at least about 0.05, at least about 0.1, at least about 0.2 inches and/or not more than about 2, not more than about 1, or not more than about 0.75 inches, or it can be in the range of from about 0.05 to about 2 inches, about 0.1 inches to about 1 inch, or about 0.2 to about 0.5 inches. The average width of each slat can be at least about 0.01, at least about 0.05, or at least about 0.1 inches and/or not more than about 1, not more than about 0.5, or not more than about 0.25 inches, or it can be in the range of from about 0.01 to about 1, from about 0.05 to about 0.5, or from about 0.1 to about 0.25 inches.

Figure 5:
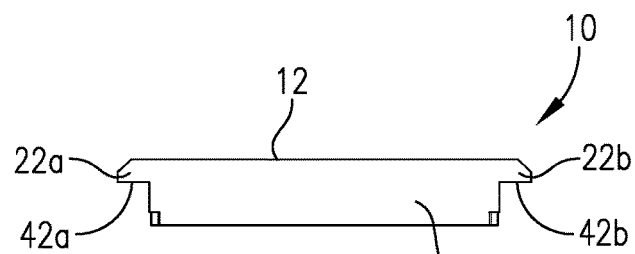
FIG. 5 is an end view of the carrier shown in FIGS. 1-3.
Figure 6:
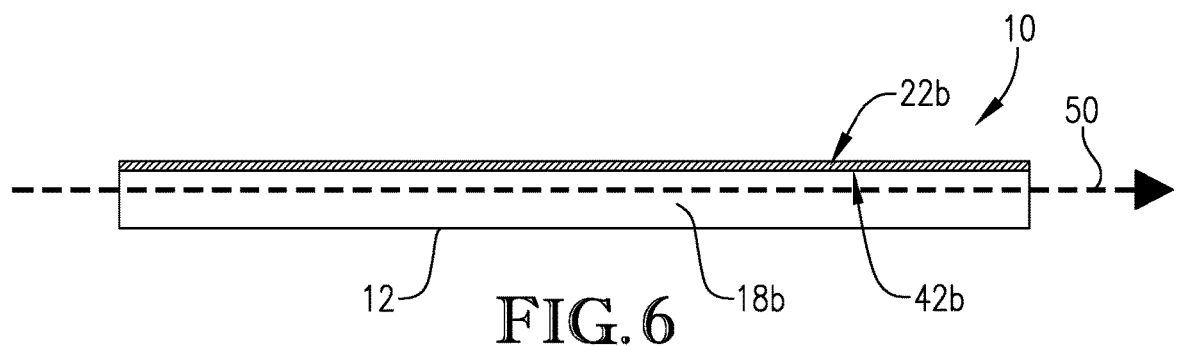
FIG. 6 is a side view of the carrier shown in FIGS. 1-3 and 5.
Figure 7:
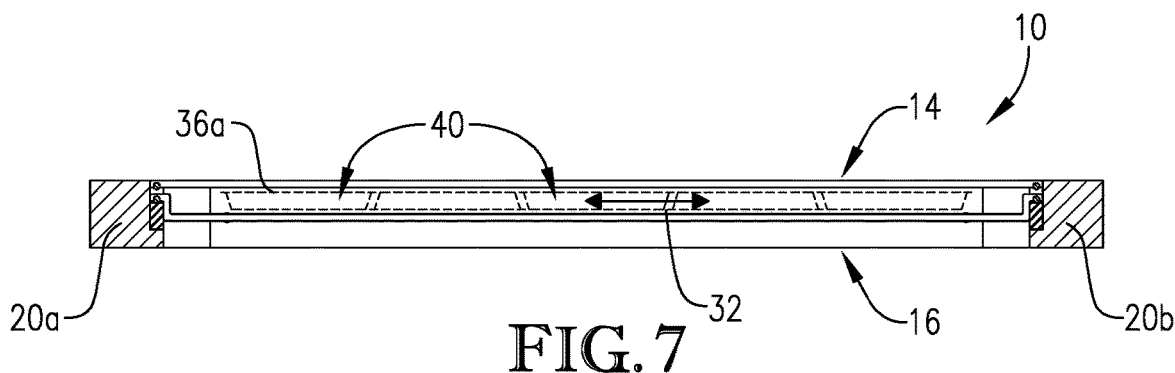
FIG. 7 is a longitudinal cross sectional view of the carrier shown in FIGS. 1-3, 5, and 6.
Figure 8:
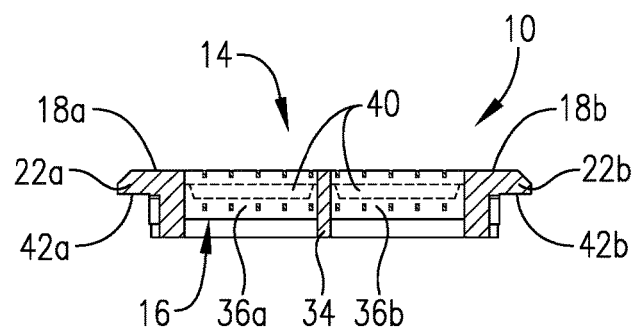
FIG. 8 is a transverse cross sectional view of the carrier shown in FIGS. 1-3 and 5-7.

Referring now to FIGS. 5 through 8, several cross sectional views of carrier 10 shown in FIGS. 1-3 are provided. Turning initially to FIG. 5, an end view of carrier 10 is provided, particularly illustrating the lower support surfaces 42a,b of first and second support projections 22a,b, respectively. FIG. 6 provides a side view of carrier 10 which particularly illustrates second support projection 22b having a lower support surface 42b for contacting a convey line support member (not shown in FIG. 6) in order to support carrier 10 on the convey line. Dashed line 50 shown in FIG. 6 indicates the direction of travel of carrier 10 along the convey line. FIG. 7 provides a cross sectional view of carrier 10, with the cross section being cut longitudinally through the carrier. As particularly shown in FIG. 7, upper and lower support members 14, 16 are vertically spaced from one another to provide a cargo volume 32 for holding articles 40 therebetween. FIG. 8 provides a transverse cross sectional view of carrier 10, and particularly illustrates the use of a longitudinal divider 34 to create multiple compartments 36a,b within cargo volume 32 for receiving multiple rows of articles 40.

As particularly shown in FIG. 7, cargo volume 32 can be at least partially defined between the upper and lower support structures 14, 16. The articles 40 received in cargo volume 32 may be held in position by at least a portion of the individual support members in upper and lower groups of support members 26a,b, which may contact the articles. Each of upper and lower support structures 14, 16 may be coupled to outer frame 12 in a manner that allows upper and/or lower support structure 14, 16 to be opened for loading articles into carrier 10, closed during heating of the articles, and opened again for unloading of the articles from carrier 10. For example, in some embodiments, the lower support structure 16 may be permanently fixed to frame 12, while the upper support structure may be coupled to frame 12 in a removable or hinged manner. This allows the upper support structure to be opened for the insertion of articles 40 into cargo volume 32 prior to heating, and removal of articles 40 from cargo volume 32 after heating. When upper support structure 14 includes a plurality of individual support members, transverse cross members 28a,b permit all of the individual support members in upper group 26a to be simultaneously removed from frame 12 or pivoted relative to the frame. In other embodiments, both the upper and lower support structures 14, 16 may be removable so that carrier 10 may be assembled and disassembled as desired.

Cargo volume 32 has a length measured between first and second end members 20a,b, a width measured between first and second side members 18a,b, and a height measured between upper and lower support structures 14, 16. In some embodiments, the length of cargo volume 32 can be at least about 0.5, at least about 1, or at least about 2 feet and/or not more than about 10, not more than about 8, or not more than about 6 feet, or it can be in the range of from about 0.5 to about 10 feet, about 1 to about 8 feet, or about 2 to about 6 feet. The width of cargo volume 32 can be at least about 0.5, at least about 1, or at least about 2 feet and/or not more than about 10, not more than about 8, or not more than about 6 feet, or it can be in the range of from about 0.5 to about 10 feet, about 1 to about 8 feet, or from about 2 to about 6 feet. The height of cargo volume 32 can be at least about 0.25, at least about 0.5, at least about 0.75 inches, or at least about 1 inch and/or not more than about 8, not more than about 6, not more than about 4, or not more than about 2 inches, or it can be in the range of from about 0.25 to about 8, from about 0.50 to about 6, from about 0.75 to about 4, or from about 1 to about 2 inches.

Carrier 10 may further include at least one article spacing member for adjusting the size and/or shape of cargo volume 32. Examples of article spacing members can include dividers for dividing cargo volume 32 into a plurality of compartments and vertical spacers for adjusting the vertical height between upper and lower support structures 14, 16. In some embodiments, one or more article spacing members may be permanently coupled to at least one of frame 12, upper support structure 14, and lower support structure 16 of carrier 10, while, in other embodiments, one or more article spacing members may be removably coupled to at least one of frame 12, upper support structure 14, and lower support structure 16 of carrier 10, such that the article spacing member may be selectively inserted into and removed from carrier 10 in order to change the size and/or shape of cargo volume 32 of carrier 10. As a result, carrier 10 may be configured to hold articles having different sizes and/or shapes.

Figure 9:
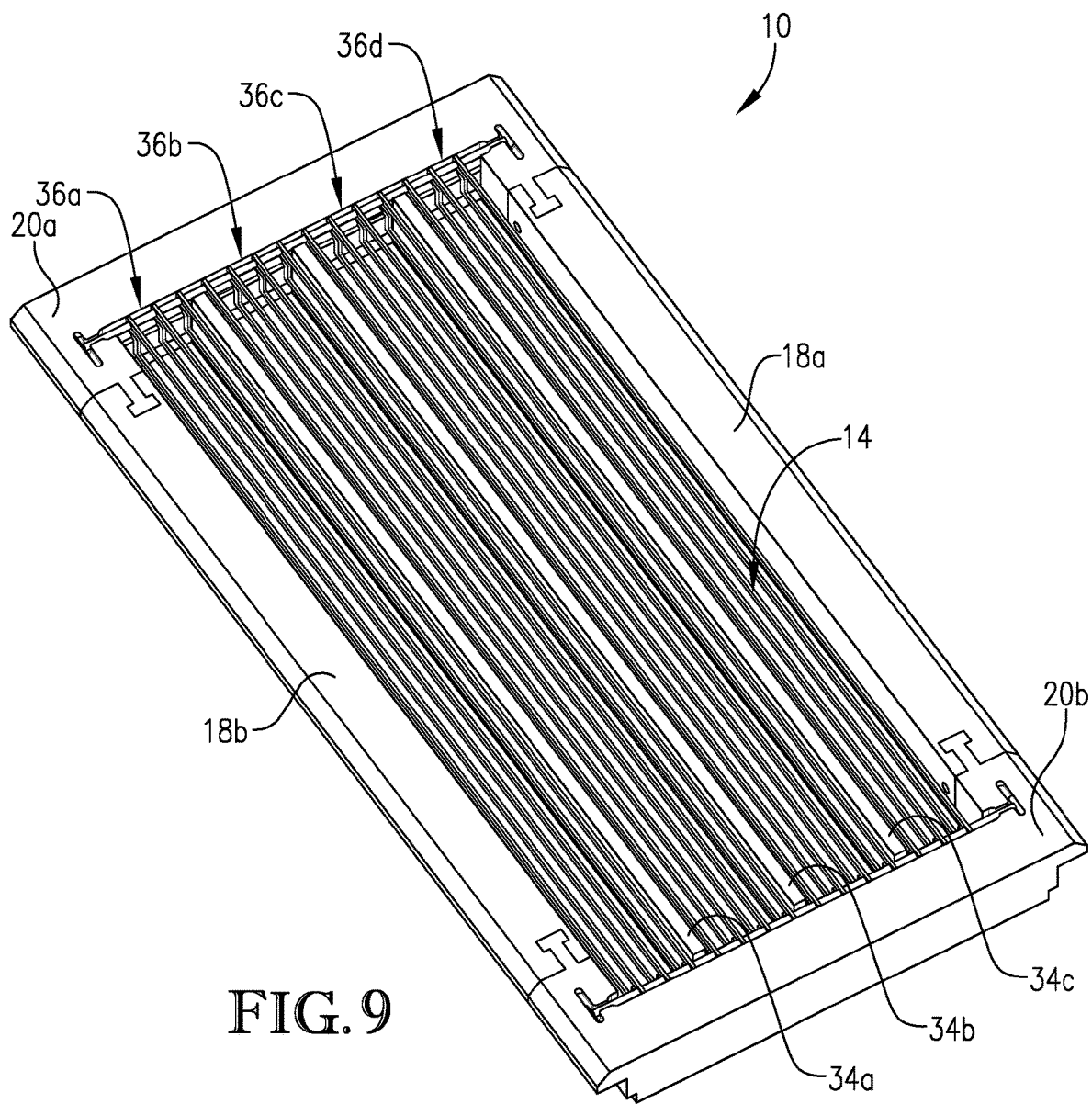
FIG. 9 is a top front isometric view of another carrier configured according to one or more embodiments of the present invention, particularly illustrating a carrier having more than two compartments in the cargo volume.

Referring again to FIGS. 1-8 and 16-19, carrier 10 may comprise at least one divider 34 for dividing cargo volume 32 into a plurality of compartments 36a,b. Divider 34 may be coupled to and extend between end members 20a,b in a direction substantially parallel to side members 18a,b and to the individual support members in upper and lower groups 26a,b. Although shown in FIGS. 1-8 and 16-19 as including a single divider 34 and two compartments 36a,b, it should be understood that carrier 10 may employ any suitable number of dividers for separating its cargo volume 32 into any desired number of compartments. In general, the cargo volume of a carrier including n longitudinal dividers will have n+1 compartments, wherein n is an integer. In some embodiments, carrier 10 can include at least 2, at least 3, or at least 4 dividers and/or not more than 10, not more than 8, not more than 6, or not more than 5 dividers, or it can include from 1 to 10, from 2 to 8, or from 3 to 6 dividers. As a result, the total number of compartments defined within cargo volume 32 of carrier 10 may be at least 2, at least 3, or at least 4 and/or not more than 11, not more than 9, not more than 7, or not more than 6 compartments, or it may be in the range of from 2 to 11, from 3 to 9, or from 4 to 7. One example of a carrier 10 that comprises three dividers 34a-c that form four compartments 36a-d is illustrated in FIG. 9, with like numerals indicating like components.

When present, each divider 34 may have a length of at least about 0.5, at least about 1, at least about 2 feet and/or not more than about 10, not more than about 8, or not more than about 6 feet, or the support members can have a length of from about 0.5 to about 10 feet, from about 1 to about 8 feet, or about 2 to about 6 feet. Each divider may have a width of at least about 0.25, at least about 0.5, at least about 0.75 inches and/or not more than about 3, not more than about 2, or not more than about 1 inch, or it can be in the range of from about 0.25 to about 3 inches, from about 0.5 to about 2 inches, or about 0.75 inches to about 1 inch. The height of divider 34 can be at least about 0.25, at least about 0.5, at least about 0.75 inches, or at least about 1 inch and/or not more than about 8, not more than about 6, not more than about 4, or not more than about 2 inches, or it can be in the range of from about 0.25 to about 8, from about 0.50 to about 6, from about 0.75 to about 4, or from about 1 to about 2 inches. Divider 34 may be formed of an electrically non-conductive material, such as, for example, a low loss tangent material as described herein. It may be formed of the same low loss tangent material as, or a different low loss tangent material than, frame 12.

Figure 10:
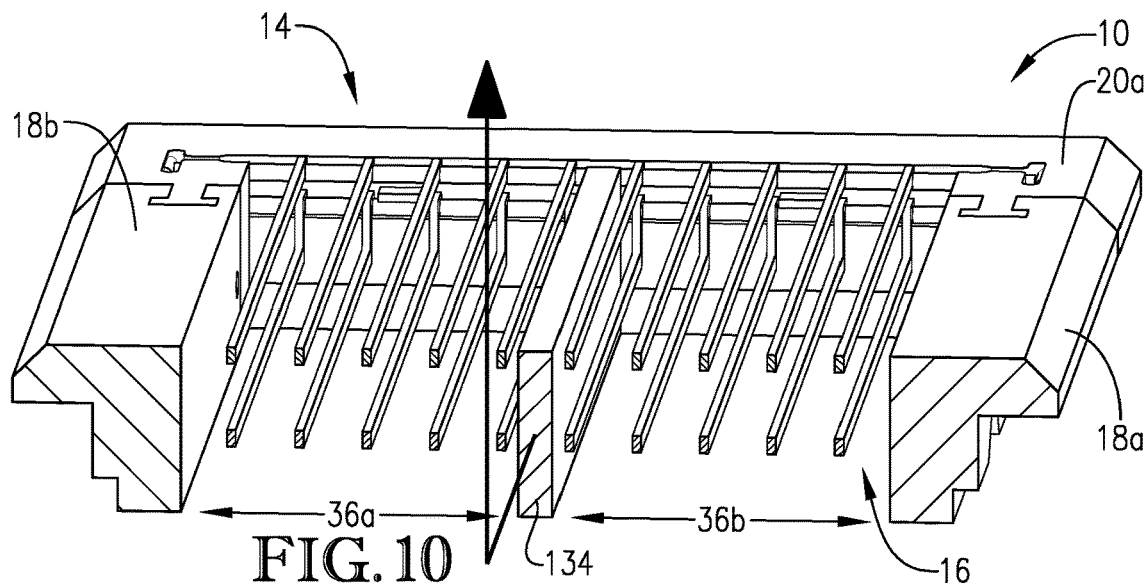
FIG. 10 is a partial isometric view of a carrier configured according to one or more embodiments of the present invention that includes a removable divider, particularly illustrating the divider being in a first position.
Figure 11:
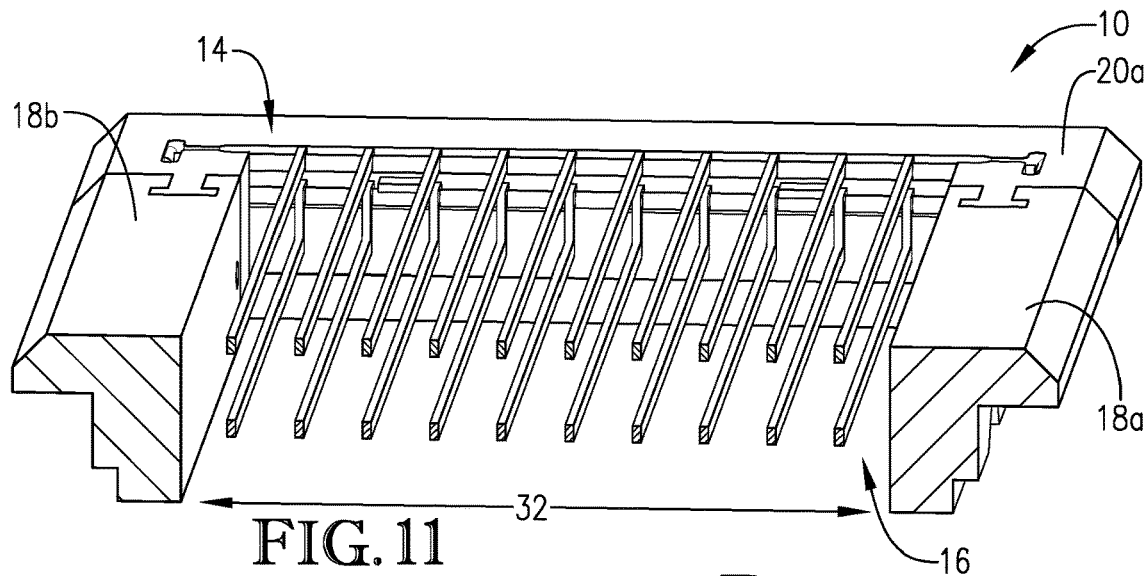
FIG. 11 is a partial isometric view of the carrier illustrated in FIG. 10, particularly illustrating the divider being removed from the carrier.
Figure 12:
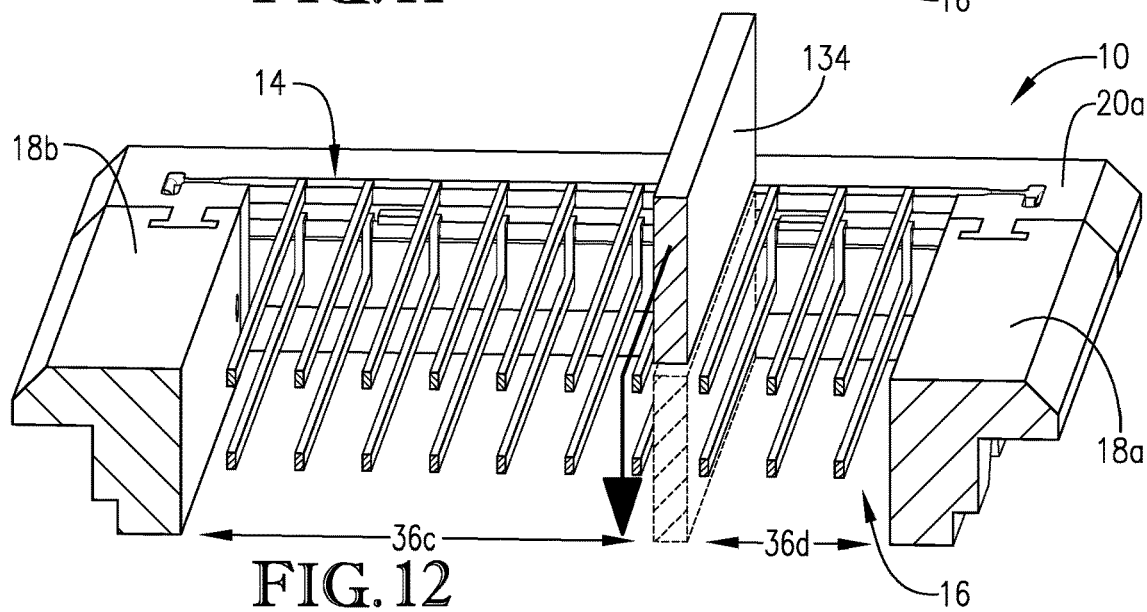
FIG. 12 is a partial isometric view of the carrier illustrated in FIGS. 10 and 11, particularly illustrating the divider being reinserted into the carrier in a different position.

In some embodiments, divider 34 may be permanently coupled to end members 20a,b. In other embodiments, divider 34 may be removably coupled to end members 20a,b so that divider 34 may be selectively inserted and removed from carrier 10 in order to change the size and/or shape of cargo volume 32. Turning now to FIGS. 10-12, several configurations of a carrier 10 that includes a removable divider 134 is provided, with like numerals indicating like components.

As shown in FIG. 10, after the articles are unloaded from compartments 36a and 36b of carrier 10, divider 134 may be removed from carrier 10, as shown by the arrow, so that cargo volume 32 is no longer compartmentalized, as shown in FIG. 11. Next, as shown in FIG. 12, divider 134 may be reinserted into carrier 10 in a different location side members 18a,b, thereby creating new and differently sized compartments 36c,d. As shown in FIG. 12, compartment 36c is slightly wider than compartment 36a shown in FIG. 10 and, as a result, compartment 36c of the configuration of carrier 10 shown in FIG. 12 is able to hold articles having a greater width than compartment 36a of the configuration of carrier 10 shown in FIG. 10. Similarly, compartment 36b shown in the configuration of carrier 10 depicted in FIG. 10 is wider than and can hold articles having a greater width than compartment 36d shown in FIG. 12. Although shown as including a single removable divider 234, it should be understood that carriers according to the present invention may include any number of removable dividers that can be selectively inserted, removed, and/or repositioned as desired within carrier 10 in order to change the shape and/or size of cargo volume 32. As a result, carriers as described herein can facilitate the processing of articles of a wide variety of types, sizes, and/or shapes.

Vertical spacers are another type of article spacing member that may be utilized by one or more carriers configured according to embodiments of the present invention. In some embodiments, the carrier may include at least one pair of vertical spacers for adjusting the vertical distance between the upper and lower support structures. When present, the pair of vertical spacers may be positioned at opposite ends of the carrier and may be coupled to the end members. Vertical spacers according to embodiments of the present invention may be any suitable size or have any suitable shape, as long as, when coupled to the end members of carrier, the vertical spacers are capable of adjusting the vertical spacing between the upper and lower support structures. Each of the vertical spacers may be formed of a low loss tangent material as described herein, and may, in some embodiments, be formed of the same low loss tangent material as, or a different low loss tangent material than, used to form the frame. Several embodiments of suitable vertical spacers are discussed in detail below.

Figure 13:
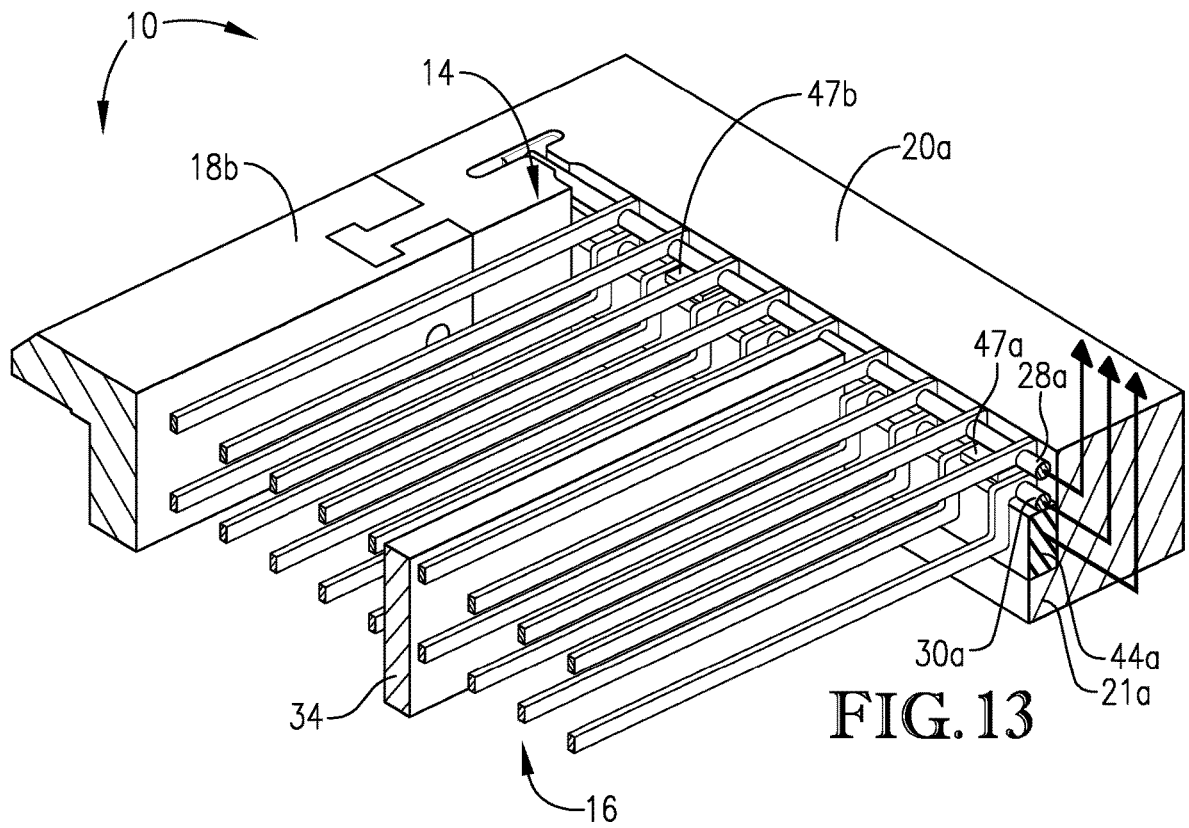
FIG. 13 is a partial isometric view of a carrier configured according to one or more embodiments of the present invention that includes a vertical spacer.
Figure 15:
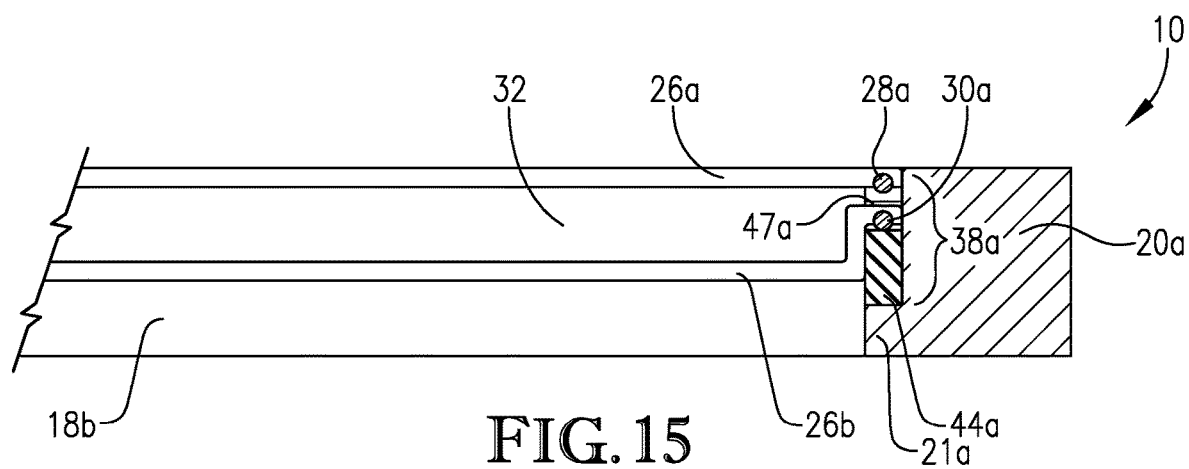
FIG. 15 is a partial cross sectional view of the carrier shown in FIGS. 13 and 14.
Figure 14:
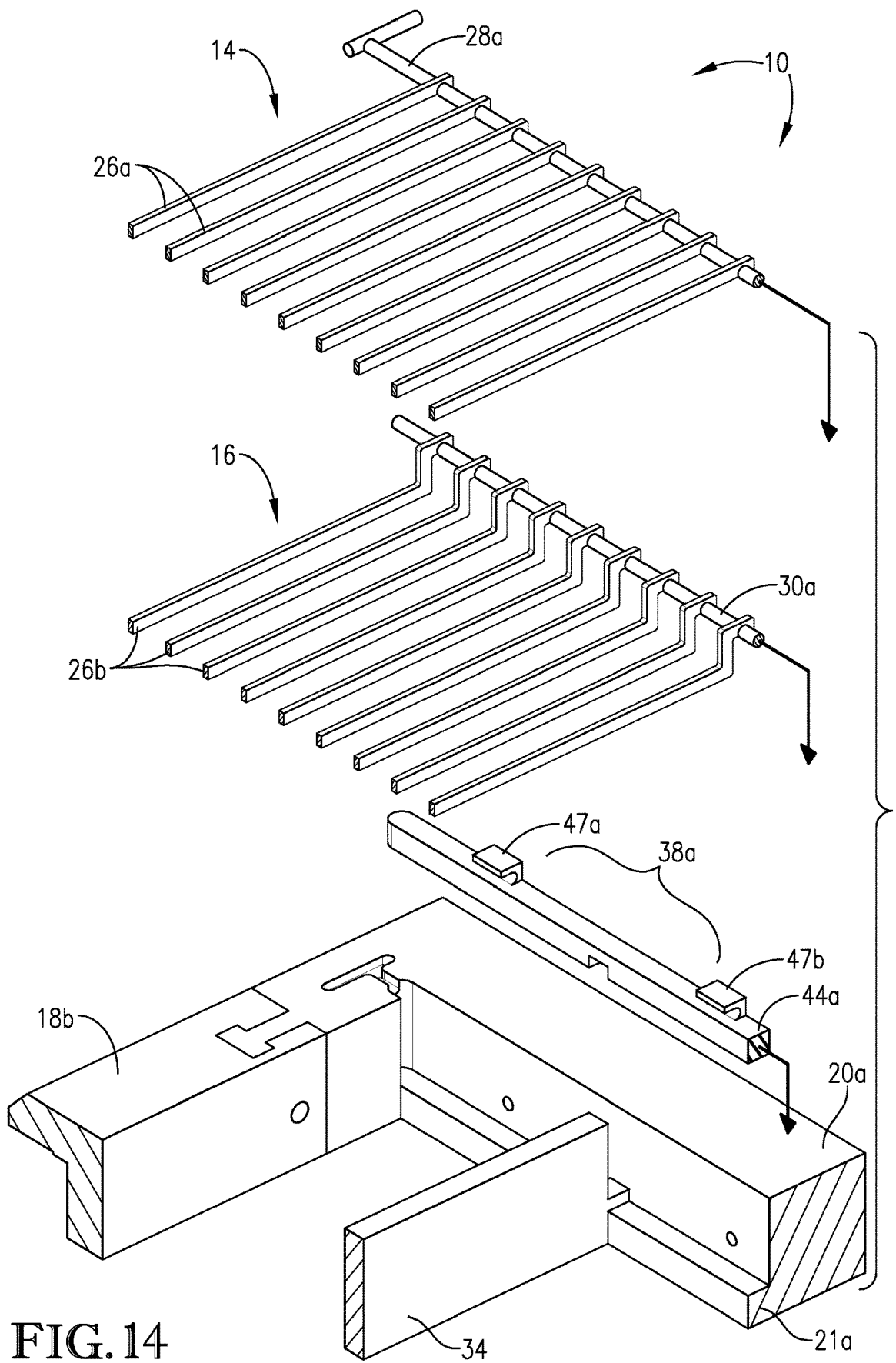
FIG. 14 is a partial exploded view of the carrier shown in FIG. 13.

Turning first to FIGS. 13-15, several partial views of the carrier 10 illustrated in FIGS. 1-3 are provided. In the embodiments represented by FIGS. 13-15, carrier 10 includes a pair of vertical spacers 38a,b coupled to end members 20a,b. Although only shown in partial view in FIGS. 13 and 15, it should be understood that the opposite end of carrier 10 (not shown) includes a second vertical spacer 38b configured similar to first vertical spacer 38a, as generally shown in FIG. 3. Referring again to FIGS. 13-15, vertical spacer 38a includes a base portion 44a configured to be coupled to end member 20a. End member 20a includes a lower support projection 21a for supporting base portion 44a of vertical spacer 38a. Base portion 44a may have a length and width similar to, but slightly less than, the length and width of end member 20a, and it may have a height of at least about 0.10, at least about 0.25, at least about 0.5, or at least about 0.75 inches and/or not more than about 2.5, not more than about 2, not more than about 1.5, or not more than about 1 inch, or its height can be in the range of from about 0.10 to about 2.5 inches, from about 0.25 to about 2 inches, from about 0.5 to about 1.5 inches, or from about 0.75 to about 1 inch.

Additionally, in some embodiments, vertical spacer 38a may include a plurality of securing devices, shown as tabs 47a,b in FIGS. 13 and 14 for securing lower support structure 16 into carrier 10. For example, as shown in FIG. 13, at least a portion of transverse cross member 30a of lower support structure 16 may be inserted into tabs 47a,b. Although shown in FIG. 14 as including two tabs 47a,b, it should be understood that any suitable number of tabs could be included, and, it should also be understood that other securing devices may also be used in place of tabs 47a,b to provide similar results. Further, although not shown in FIGS. 13-15, it should be understood that the opposing end of carrier 10 may have a similarly configured vertical spacer, as is generally shown in FIG. 3.

Turning now to FIGS. 16-19, carrier 10 is shown as including a pair of vertical spacers 48a,b configured according to other embodiments of the present invention. Similarly to vertical spacers 38a,b shown in FIGS. 13-15, vertical spacers 48a,b each include a base portion 54a,b configured to be coupled to end member 20a,b and to support at least a portion of lower support structure 16. As shown in FIG. 19, base portions 54a,b of vertical spacers 48a,b each comprises an "L"-shaped base portion configured to rest on lower support projection 21a,b of end member 20a,b and to contact at least a portion of angled portion 27a,b of lower support structure 16. Base portions 54a,b may have a length and width similar to, but slightly less than, the length and width of end members 20a,b and it may have a height, shown as h in FIG. 19, of at least about 0.10, at least about 0.25, at least about 0.5, or at least about 0.75 inches and/or not more than about 2.5, not more than about 2, not more than about 1.5, or not more than about 1 inch, or its height can be in the range of from about 0.10 to about 2.5 inches, from about 0.25 to about 2 inches, from about 0.5 to about 1.5 inches, or from about 0.75 to about 1 inch.

In some embodiments, vertical spacers 38a,b or 48a,b may be permanently coupled to end members 20a,b so that, once assembled, vertical spacers 38a,b or 48a,b may not be removed from carrier 10. In other embodiments, vertical spacers 38a,b and 48a,b may be removably coupled to end members 20a,b, so that vertical spacers 38a,b or 48a,b may be selectively inserted into and removed from carrier 10 once it has been assembled in order to selectively adjust the vertical spacing between upper and lower support structures 14, 16. When the pair of vertical spacers are removable, carrier 10 may be configured to receive two or more different pairs of spacers having different heights. As a result, the size of cargo volume 32 may be selectively altered by inserting one or the other pairs of removable vertical spacers into carrier 10, as discussed in further detail below.

Figure 20A:
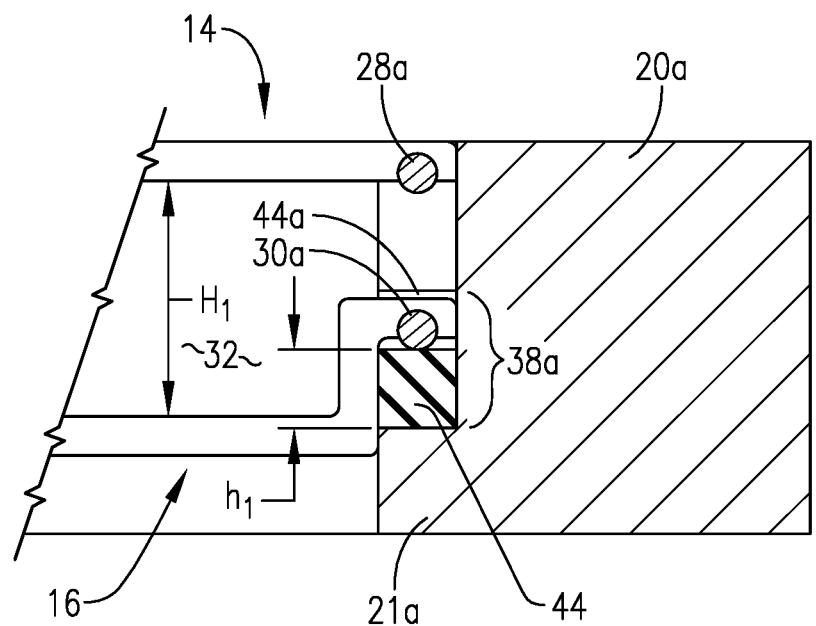
FIG. 20a is a partial cross sectional view of a carrier according to one or more embodiments of the present invention, particularly illustrating a vertical spacer having a first height.

Turning now to FIGS. 20a,b, one example of the use of removable vertical spacers is shown. More particularly, as shown in FIG. 20a, a first removable vertical spacer 38a, which is configured in a similar manner as shown in FIGS. 3 and 13-15, may be inserted into carrier 10 so that vertical spacer 38a contacts end member 20a. Although not shown, it should be understood that the opposite end of carrier 10 would be configured in a similar manner. In the embodiment, base portion 44a of first removable vertical spacer 38a may be configured to sit on lower support projection 21a of end member 20a, as shown in FIG. 20a. Base portion 44a of first removable vertical spacer 38a has a first height, shown as $h_1$, which spaces upper support structure 14 and lower support structure 16 from one another by a first vertical height, $H_1$, within carrier 10. First vertical height $H_1$ shown in FIG. 20a generally corresponds to the height of cargo volume 32.

Figure 20B:
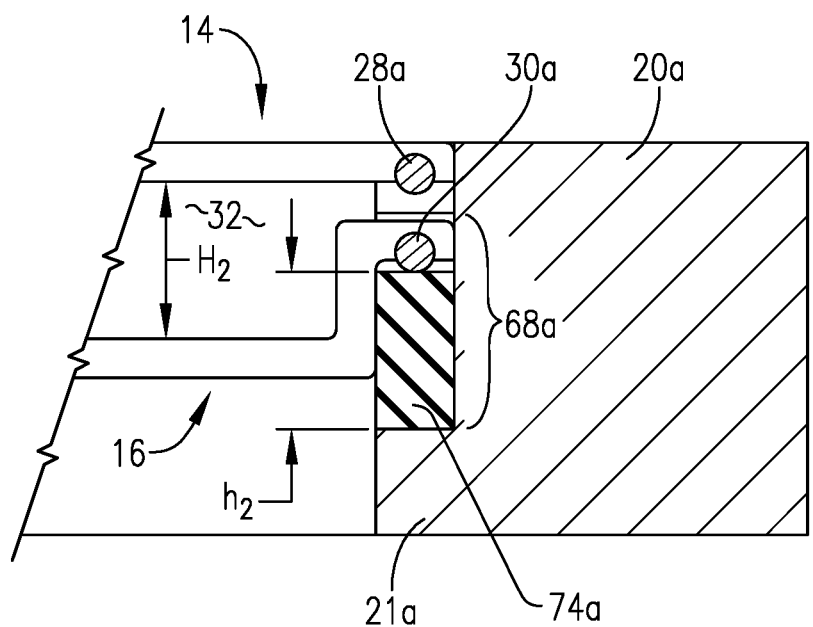
FIG. 20b is a partial cross sectional view of the carrier shown in FIG. 20a, but including a vertical spacer having a second height and particularly illustrating the use of vertical spacers to adjust the height of the cargo volume.

Turning now to FIG. 20b, the first removable vertical spacer 38a shown in FIG. 20a may be removed from carrier 10, and a second vertical spacer shown as element 68a in FIG. 20b may be inserted in its place. Again, although not shown, it should be understood that the opposite end of carrier 10 would be configured in a similar manner. In the embodiment shown in FIG. 20b, second removable vertical spacer 68a has a base portion 74a, which is also configured to sit on lower support projection 21a of end member 20a in a similar manner as base portion 44a shown in FIG. 20a. In the embodiment shown in FIG. 20b, base portion 74a of second removable vertical spacer 68a has a second height, $h_2$, which is taller than the first height, $h_1$, of base portion 44a of first removable vertical spacer 38a. As a result, upper and lower support structures 14, 16 are moved closer to one another and the second vertical height, $H_2$, between upper and lower support structures 14, 16 decreases. As a result, the height and total volume of cargo volume 32 decreases. In other embodiments, the second height, $h_2$, of the base portion 74a of second removable vertical spacers 38a may be shorter than the first height, $h_1$, of base portion 44a of first removable vertical spacer 38a, which would result in a larger vertical distance, $H_2$, between upper and lower support structures 14, 16, and an overall increased height and total volume of cargo volume 32.

Figure 21A:
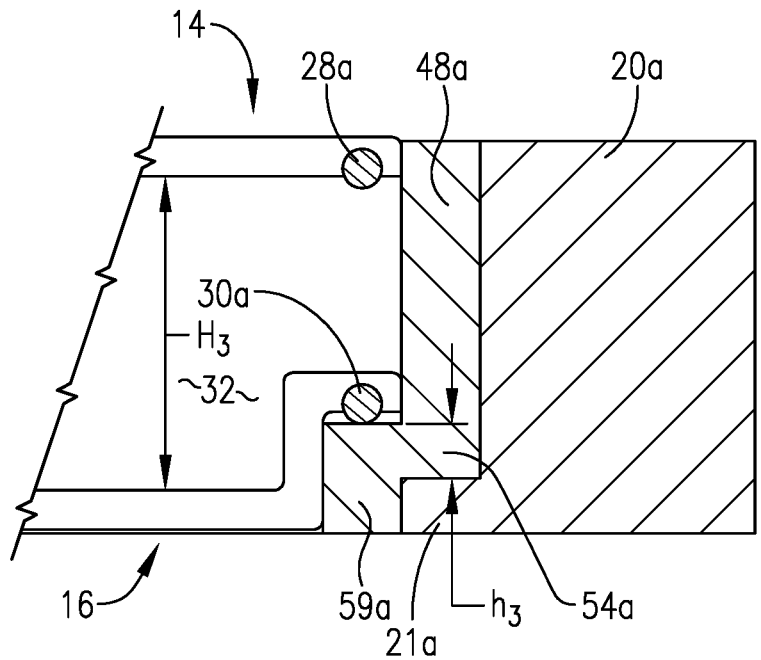
FIG. 21a is a partial cross sectional view of a carrier including another vertical spacer configured according to one or more embodiments of the present invention.
Figure 21B:
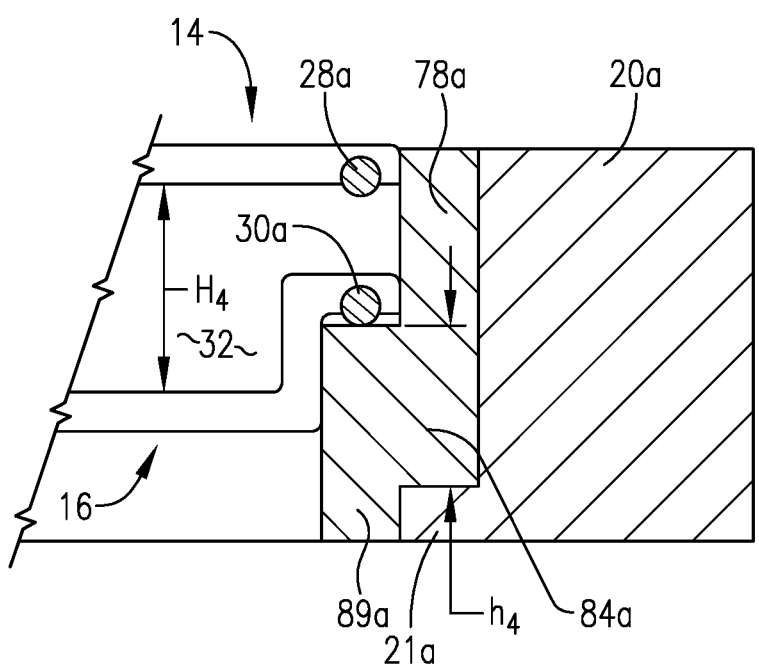
FIG. 21b is a partial cross sectional view of the carrier shown in FIG. 21a, but including second vertical spacer configured similarly to the vertical spacer shown in FIG. 21a, but having a different height and particularly illustrating the use of vertical spacers to adjust the height of the cargo volume.

A similar example is shown in FIGS. 21a and 21b, but with vertical spacers configured in similar manner as shown in FIGS. 16-19. Although FIGS. 21a and 21b show only one end of carrier 10, it should be understood that the opposite end of carrier 10 would be configured in a similar manner. As shown in FIG. 21a, a first vertical removable spacer 48a may be coupled to lower support projection 21a of end member 20a. Unlike the embodiment shown in FIGS. 20a,b, first vertical spacer 48a illustrated in FIG. 21a has a lower portion 59a that is positioned between lower support member 16 and end member 20a when vertical spacer 48a is inserted into carrier 10. As shown in FIG. 21a, first removable vertical spacer 48a has a base portion 54a that has a first height, shown as $h_3$, which results in upper support structure 14 and lower support structure 16 being spaced from one another by a first vertical height, $H_3$, within carrier 10. First vertical height $H_3$ shown in FIG. 21a generally corresponds to the height of cargo volume 32.

Turning now to FIG. 21b, the first removable vertical spacer 48a shown in FIG. 21a may be replaced by a second vertical spacer shown as element 78a as shown in FIG. 21b. Again, although not shown, it should be understood that the opposite end of carrier 10 would be configured in a similar manner. In the embodiment shown in FIG. 21b, second removable vertical spacer 78a has a base portion 84a, which is also configured to sit on lower support projection 21a of end member 20a in a similar manner as base portion 54a shown in FIG. 21a. In the embodiment shown in FIG. 21b, base portion 84a of second removable vertical spacer 68a has a second height, $h_4$, which is taller than the first height, $h_3$, of base portion 54a of first removable vertical spacer 48a. As a result, upper and lower support structures 14, 16 are moved closer to one another and the second vertical height, $H_4$, between upper and lower support structures 14, 16 decreases. As a result, the height and total volume of cargo volume 32 decreases. In other embodiments, the second height, $h_4$, of the base portion 84a of second removable vertical spacers 48a may be shorter than the first height, $h_3$, of base portion 54a of first removable vertical spacer 48a, which would result in a larger vertical distance, $H_4$, between upper and lower support structures 14, 16, and an overall increased height and total volume of cargo volume 32.

Figure 22:
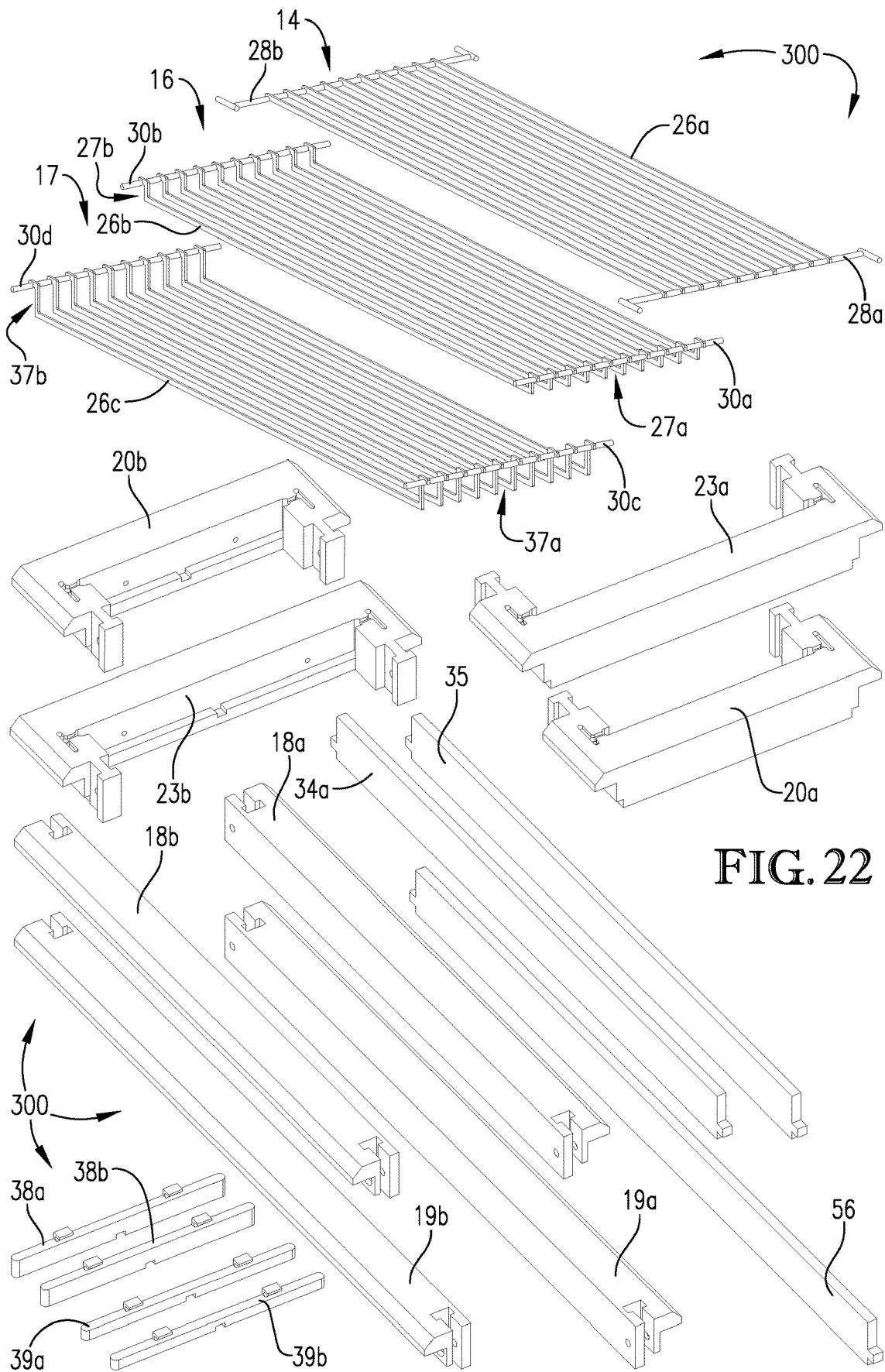
FIG. 22 is a isometric view of the components of a carrier system according to one or more embodiments of the present invention.

One or more carriers described herein may be formed from a carrier system including a plurality of components that, when assembled, form a carrier. In particular, the carrier system may include additional, differently sized elements so that carriers having one or more different configurations may be formed. One example of a carrier system 300 for transporting a plurality of articles through a microwave heating system is illustrated in FIG. 22 as generally comprising a pair of side members including a first side member 18a and a second side member 18b, a pair of end members including a first end member 20a and a second end member 20b, and an upper and lower support structure 14, 16 for securing the articles within the carrier. First and second end members 20a,b may be configured as discussed herein to be coupled to and extend between opposite ends of first and second side members 18a,b to form a generally rectangular outer frame for the carrier. When assembled to form a carrier, upper and lower support structures may be configured to extend between first and second end members 20a,b and may be vertically spaced from one another to form a cargo volume into which the articles may be loaded.

Additionally, in some embodiments, as shown in FIG. 22, carrier system 300 may further include a second pair of side members 19a,b, a second pair of end members 23a,b, and/or a second lower support structure 17. Each of pair of side members 18a,b and 19a,b are configured to be coupled to each pair of end members 20a,b and 23a,b so that carriers having different lengths and widths may be formed. Additionally, as shown in FIG. 22, second lower support structure 17 has slightly larger bent portions than first lower support structure 16, so that the depth of the cargo volume of the resulting carrier may be adjusted by changing which lower support structure 16 or 17 is employed in carrier 10. Although not shown in FIG. 22, carrier system 300 may include additional sets of side members, end members, and lower support structures.

Additionally, the carrier system 300 may further include one or more removable article spacing members. As discussed previously, article spacing members, such as vertical spacers and dividers, may be used within a carrier to adjust the cargo volume defined between the upper and lower support structures in order to accommodate articles of a given shape and/or size. When the article spacing members are removable, these article spacing members can be selectively inserted into and removed from the carrier, and the size and/or shape of the cargo volume can be adjusted so that the same carrier may be used to process several different types of articles having different shapes and/or sizes.

In some embodiments, carrier system 300 may comprise one or more sets of removable article spacing members. For example, in some embodiments, carrier system 300 may include at least one of (i) one or more pairs of vertical spacers and (ii) one or more dividers. When present, the vertical spacers and/or dividers may be removable vertical spacers and/or removable dividers configured to be selectively inserted into the cargo volume of the carrier in order to adjust the vertical spacing between the upper and lower support structures and/or to divide the cargo volume into a plurality of compartments. The sizes, shapes, and functions of both the vertical spacers and dividers, as well as the removability of such components, has been discussed in detail previously.

Carrier systems according to embodiments of the present invention may include any suitable number of pairs of vertical spacers and/or dividers. For example, in some embodiments, carrier systems may include at least 2, at least 3, or at least 4 of vertical spacers and/or at least 2, at least 3, at least 4, or at least 5 dividers. When the carrier system includes at least 2 pairs of vertical spacers, such as vertical spacers 38a,b and 39a,b shown in FIG. 22, each pair may have a different height. As a result, when assembled, the carrier may be arranged in at least two different configurations, one having a larger cargo volume when vertical spacers 39a,b are employed, and one having a smaller cargo volume when vertical spacers 38a,b are employed.

Similarly, when carrier system 300 includes more than one divider, the dividers may be identical, such as dividers 34 and 35 shown in FIG. 22, or one of the dividers may be of a different size, as shown by divider 56. When carrier system 300 includes two or more sets of side members and dividers, system 300 may include at least one divider suitable for use with each set of side members. When assembled, the carrier may include one, a portion, all, or none of the dividers selectively inserted into the cargo volume. Additionally, one of the pairs of vertical spacers 38*a,b* and 39*a,b* may be employed with one, a portion, all, or none of the dividers may be utilized, which provides a plurality of possible carrier configurations that may be used to hold and heat many different types of articles having various sizes and/or shapes.

In operation, a carrier system as described above may be assembled into a first carrier configuration, into which a plurality of a first type of articles may be loaded. As discussed herein, the carrier may include a frame formed by assembling first and second side members and first and second end members into a generally rectangular configuration, and an upper and lower support structure for securing the articles. Thereafter, the loaded carrier may be transported to a microwave heating zone, wherein the articles may be heated using microwave energy. Several embodiments of suitable microwave heating zones will be discussed in further detail below.

After being heated and optionally cooled, the first type of articles may be unloaded from the carrier. Next, the carrier may be reconfigured to change the size and/or shape of the cargo volume. In some cases, the reconfiguring includes removing one or more article spacing members from the carrier and/or repositioning one or more article spacing members within the carrier. When an article spacing member is removed from the carrier, another article spacing member may be inserted into the carrier in the same or a different position, or the same article spacing member may be repositioned within the carrier. In some cases, no article spacing member may be inserted or reinserted into the carrier after an article spacing member has been removed. In some embodiments, an article spacing member may be repositioned within the carrier, with or without first being removed. In some embodiments, the size and/or shape of the cargo volume may be changed by switching one pair of side members or one pair of end members, or by utilizing a different lower support member in carrier. Once changed into a second configuration, the carrier may be loaded with a plurality of a second type of articles having a different size and/or shape than the first type, and the loaded carrier may be transported to and heated in the microwave heating zone.

Carriers configured according to embodiments of the present invention may be configured to hold many different types of articles. Examples of suitable articles can include, but are not limited to, packaged foodstuffs, such as, for example, fruits, vegetables, meats, pastas, pre-made meals, soups, stews, jams, and even beverages, packaged medical fluids such as saline solution or pharmaceuticals or pharmaceutical fluids, and packaged medical or dental instruments.

The articles can be of any suitable size and shape. In one embodiment, each article can have a length (longest dimension) of at least about 1, at least about 2, at least about 4, or at least about 6 inches and/or not more than about 18, not more than about 12, not more than about 10, not more than about 8, or not more than about 6 inches; a width (second longest dimension) of at least about 1 inch, at least about 2 inches, at least about 4 inches and/or not more than about 12 inches, not more than about 10 inches, or not more than about 8 inches; and/or a depth (shortest dimension) of at least about 0.5 inches, at least about 1 inch, at least about 2 inches and/or not more than about 8 inches, not more than about 6 inches, or not more than about 4 inches.

The articles can comprise individually packages each having, in some embodiments, a generally rectangular or prism-like shape. In some cases, the articles can have a top and a bottom and the top and bottom of each article can have different widths. For example, in some cases, the top can be wider than the bottom and top edge of each article may be longer and wider than the bottom edge. In other cases, the top may be narrower than the bottom when, for example, the article includes a flexible pouch. Specific types of articles can include, but are not limited to, flexible and semi-flexible pouches with or without spouts, cups, bottles, and other rigid or semi-rigid containers having circular, elliptical, or other cross-sectional shapes with or without lidding, including flexible lidding. The articles may be constructed of any material, including plastics, cellulosics, and other microwave-transparent materials.

When loaded into a carrier as described herein, the articles are placed within the cargo volume defined between the upper and lower support structures of the carrier. As discussed above, the cargo volume may be a single volume, or it may be divided into two or more compartments using one or more dividers. When loaded into the cargo volume, the articles may be placed in single rows along the length of the carrier. In some embodiments, the articles may be arranged in at least 2, at least 3, at least 4, at least 5, or at least 6 single rows and/or not more than 15, not more than 12, not more than 10, or not more than 8 single rows, or from 2 to 15 single rows, from 3 to 12 single rows, from 4 to 10 single rows, or from 5 to 8 single rows. Overall, carriers according to embodiments of the present invention can hold at least 6, at least 8, at least 10, at least 12, at least 16, at least 18, at least 20, at least 24, at least 30 articles and/or not more than 100, not more than 80, not more than 60, not more than 50, or not more than 40 articles, or it can hold from 6 to 100 articles, from 8 to 80 articles, from 10 to 60 articles, from 12 to 50 articles, or from 18 to 40 articles. Articles can be loaded into the carrier in any suitable manner, including manually or using an automated device.

In some embodiments, the articles can be loaded into the cargo volume such that at least about 60, at least about 65, at least about 70, at least about 75, at least about 80, at least about 85, at least about 90, at least about 92, at least about 95, at least about 97, or at least about 99 percent of the total volume of the cargo volume is occupied by the articles. As a result, the total empty or void space within the cargo volume can be not more than about 40, not more than about 35, not more than about 30, not more than about 25, not more than about 20, not more than about 15, not more than about 10, not more than about 8, not more than about 5, not more than about 3, or not more than about 1 percent of the total volume of the cargo volume.

In some embodiments, it may be desirable to minimize spacing between the articles so that the average distance between consecutive edges of adjacent articles loaded in the carrier can be not more than about 1 inch, not more than about 0.75 inches, not more than about 0.5 inches, not more than about 0.25 inches, or not more than about 0.1 inch. In some embodiments, there may be no gaps between the articles such that adjacent articles are in contact with one another when loaded into the carrier. In other embodiments, at least a portion of adjacent articles may overlap horizontally.

How the articles are loaded into the carrier may depend, at least in part, on the shape of the articles. When the articles have a general trapezoidal-like shape, such that the articles are longer and wider on the top than on the bottom, the articles may be arranged in a single or multiple layer nested configuration, as respectively shown in FIGS. 23*a* and 23*b*. In a nested configuration, at least a portion (or all) of one article can be positioned directly above at least a portion (or all) of an adjacent article.

Figure 23A:
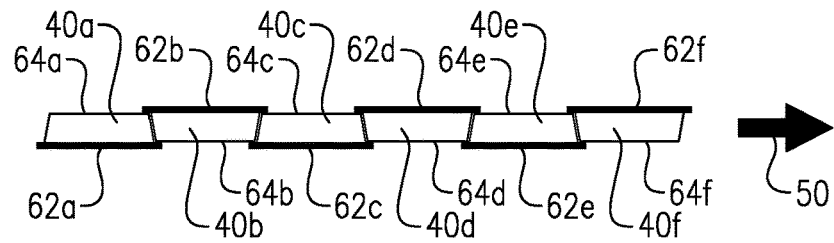
FIG. 23a is a side view of a plurality of articles arranged in a nested configuration.
Figure 23B:
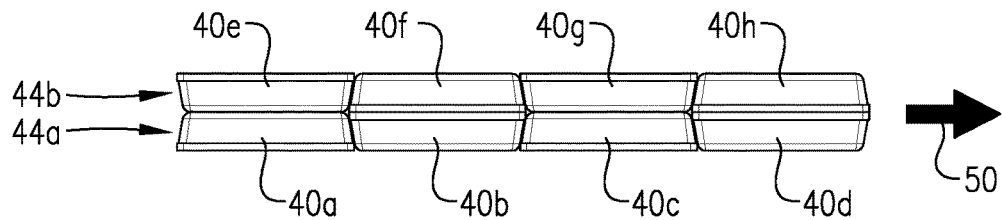
FIG. 23b is a side view of a plurality of articles arranged in a multiple layer nested configuration.

FIG. 23*a* illustrates a side view of one row of articles 40 arranged in a nested configuration. In the nested configuration, adjacent articles 40*a-f* have opposite orientations. In the nested configuration, the row of articles 40*a-f* loaded into the carrier (not shown) can be sequentially oriented in the direction of travel 50 of the carrier in a top down, top up, top down, top up configuration. As shown in FIG. 23*a*, the bottom 64*b* of the second article 40*b* is oriented between the top 62*a* of the first article 40*a* and the top 62*c* of the third article 40*c*. Additionally, in the nested configuration, the tops 62*a*, 62*c*, and 62*e* of one set of alternating articles 40*a*, 40*c*, and 40*e* and the bottoms 64*b*, 64*d*, and 64*f* of the other set of alternating articles 40*b*, 40*d*, and 40*f* contact the lower support structure, while the bottoms 64*a*, 64*c*, and 64*e* and tops 62*b*, 62*d*, and 62*f* of each set of alternating articles 40*a,c,e* and 40*b,d,f* contact the upper support structure when articles 40*a-f* are loaded into the carrier. It has been discovered that arranging the articles in a nested configuration can provide for more uniform heating. In some embodiments, the nested configuration may be most useful for processing rigid articles such as trays, containers, and the like. When the articles are configured in a multiple layer nested configuration, as shown in FIG. 23*b*, the articles 40*a-h* may be arranged in at least two rows, including a lower row 44*a* in contact with a portion of the lower support structure of the carrier (not shown) and an upper row 44*b* located on top of the lower row 44*a*. Although shown in FIG. 23*b* as including two rows, a multiple layer nested configuration can include at least three, at least four, or even five or more rows, depending on the height of the cargo volume of the carrier and the height of the individual articles. Overall, the total height of the stacked articles should be less than or equal to the height of the cargo volume to ensure that the upper support structure can secure the articles in place during heating. Although shown in FIG. 23*b* with respect to trapezoidal-shaped articles, other types of articles, including bottles, cups, and flexible pouches, may also be arranged in a multiple layer configuration including a lower row and at least one upper row on top of the lower row.

In some embodiments, the articles in the upper row of a multiple layer configuration, including the multiple layer nested configuration shown in FIG. 23*b*, can be positioned directly above a corresponding article in the lower row. For example, as shown in the embodiment depicted in FIG. 23*b*, each of articles 40*e-h* in the upper row 44*b* are positioned directly above another of the articles 40*a-d* in the lower row 44*a*. In some embodiments, such as the one shown in FIG. 23*b*, the upper articles 40*e-h* and lower articles 40*a-d* are not offset from one another, such that the bottom or top of the article 40*e-h* in the upper row 44*b* only contacts the bottom or top of the corresponding article 40*a-d* in the lower row 44*a*. In other embodiments, one or more of the articles 40*a-h* may be offset from one another, such that the bottom or top of articles 40*a-d* in the lower row 44*a* may contact the bottom or top of at least two different articles 40*e-h* in the upper row 44*a*.

In some embodiments, the articles 40*a-d* in the lower row 44*a* and the articles 40*e-h* in the upper row 44*b* are arranged in oppositely-configured nested configurations. That is, the articles 40*a-d* in the lower row 44*a* are arranged in a top down, top up nested pattern and the corresponding articles 40*e-h* in the upper row 44*b* are arranged in a top up, top down nested pattern. As a result, corresponding articles in the upper and lower rows 44*a* and 44*b* (e.g., articles 40*a* and 40*e*, articles 40*b* and 40*f*, articles 40*c* and 40*g*, and articles 40*d* and 40*h* in FIG. 23*b*) are arranged so that the tops of alternating upper and lower articles are in contact (e.g., the tops of articles 40*b* and 40*f* and articles 40*d* and 40*h* in FIG. 23*b*) and the bottoms of alternative upper and lower articles are in contact (e.g., the bottoms of articles 40*a* and 40*e* and articles 40*c* and 40*g* in FIG. 23*b*). Optionally, the upper and lower rows 44*a* and 44*b* may be spaced apart from one another via one or more dividers (not shown).

Figure 24:
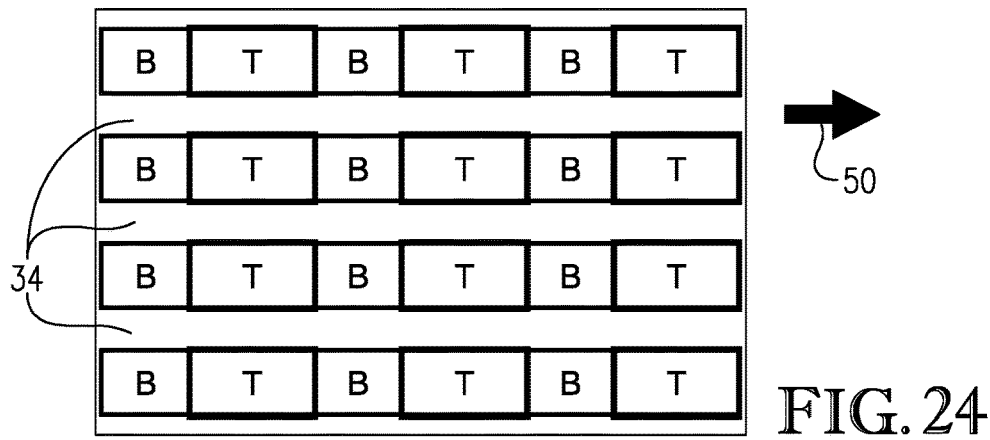
FIG. 24 is a top view of the plurality of articles shown in FIG. 23a or 23b, particularly illustrating a divided row nested configuration.
Figure 25:
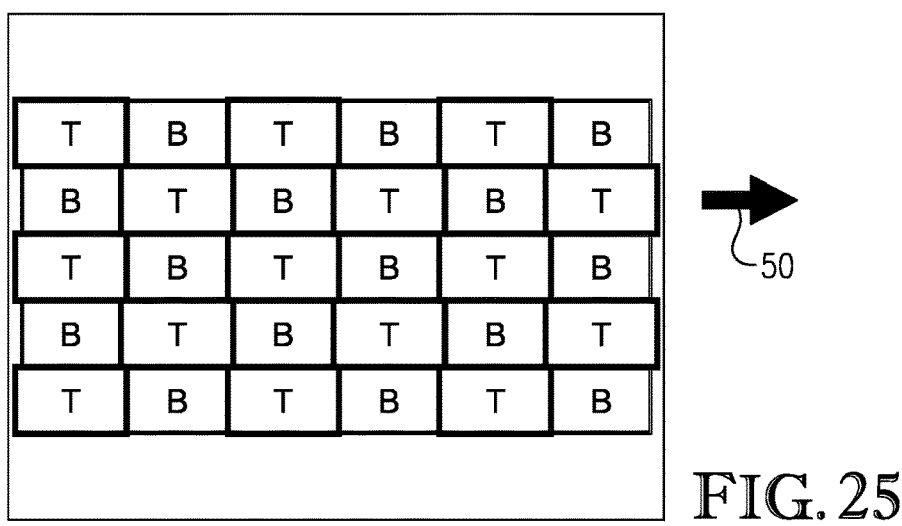
FIG. 25 is a top view of another plurality of articles arranged in a nested configuration, particularly illustrating a full or continuous nested configuration.

Turning now to FIGS. 24 and 25, two top views of a plurality of articles arranged in different nested (single or multiple layer) configurations a carrier are provided. In each of FIGS. 24 and 25, the tops of articles are marked with a "T," the bottoms articles are marked with a "B," and the direction of travel of the carrier is shown by arrow 50. The embodiment shown in FIG. 24 represents a nested configuration wherein each row of nested articles are spaced from one another, and FIG. 25 illustrates a fully nested pattern, wherein the individual rows of nested articles are not spaced from one another and the articles are arranged in a nested configuration in both the longitudinal and transverse directions. In the nested pattern shown in FIG. 24, a plurality of dividers 34 are used to separate the individual rows of nested articles within the carrier. In the fully nested article pattern shown in FIG. 25, the articles are not only nested end-to-end along the length of the carrier in a direction parallel to the direction of travel, but are also nested side-to-side in a transverse direction perpendicular to the direction of travel of the carrier. In the fully nested configuration shown in FIG. 25, no dividers are used to separate the individual rows of articles.

Figure 26:
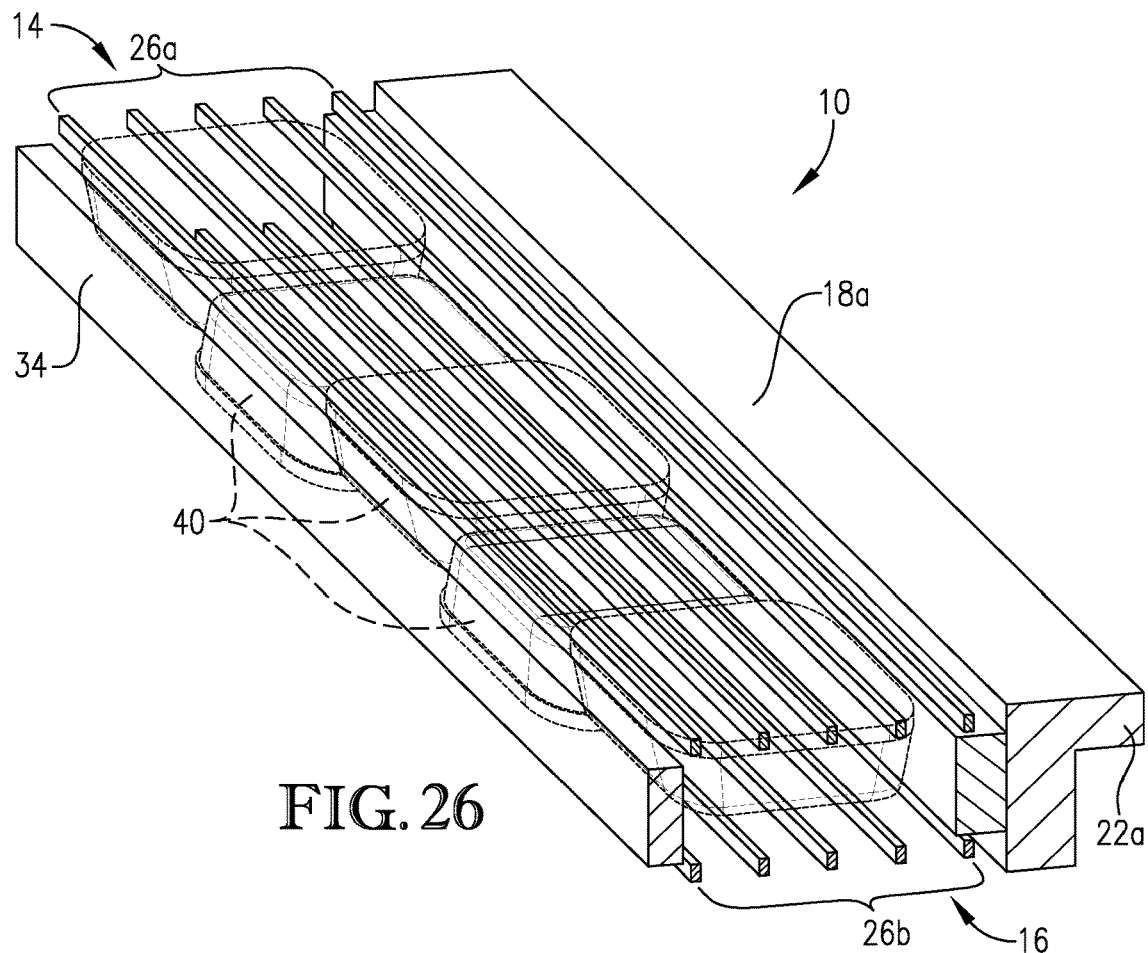
FIG. 26 is an isometric view of another carrier according to one or more embodiments of the present invention.
Figure 27:
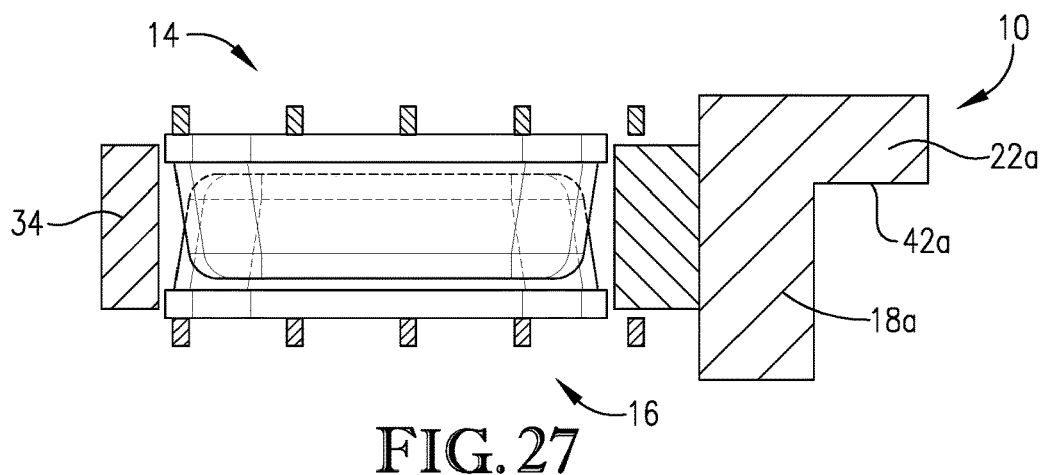
FIG. 27 is a transverse cross sectional view of the carrier shown in FIG. 26.
Figure 28:
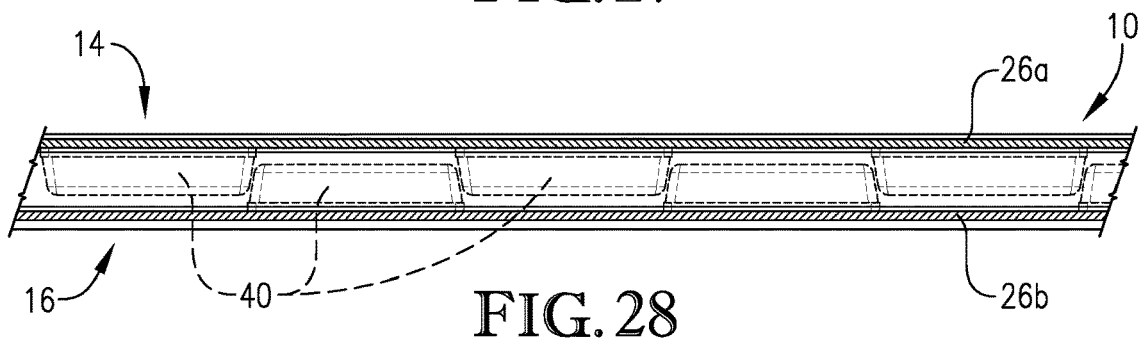
FIG. 28 is a longitudinal cross sectional view of the carrier shown in FIGS. 26 and 27.

Turning now to FIGS. 26-30, several isometric views of one row of articles 40 within carrier 10 are provided. As shown in FIG. 26, articles 40, which are arranged in a nested configuration, are lined up a single row in a compartment 36*a* defined between upper and lower support structures 14, 16 and between divider 34 and side member 18*a*. FIG. 26 also illustrates the support projection 22*a* extending outwardly from side member 18*a*. In the embodiment shown in FIG. 26, upper and lower support structures 14, 16 include upper and lower groups of support members 26*a* and 26*b*. In the embodiment shown in FIG. 26, the individual support members in upper and lower groups 26*a,b* include slats having a generally rectangular cross sectional shape arranged so that the height of each slat is greater than its width. Such a configuration may provide superior strength and enhancement of microwave field uniformity. In some embodiments, the slats may be formed of electrically conductive material as described herein.

Figure 29:
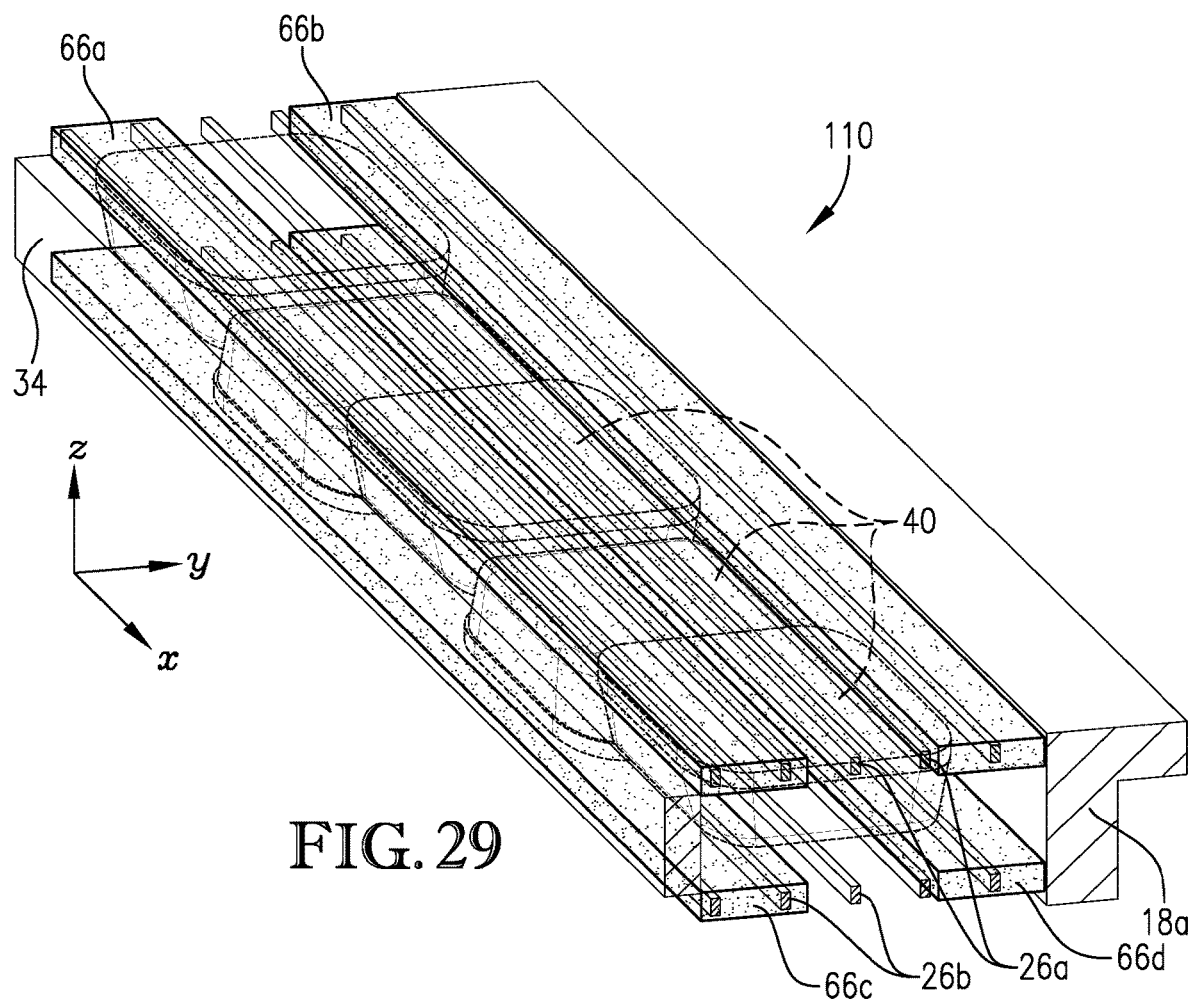
FIG. 29 is a partial isometric view of another carrier configured according to one or more embodiments of the present invention, particularly illustrating use of dielectric shapers to enhance the uniformity of the applied electric field.
Figure 30:
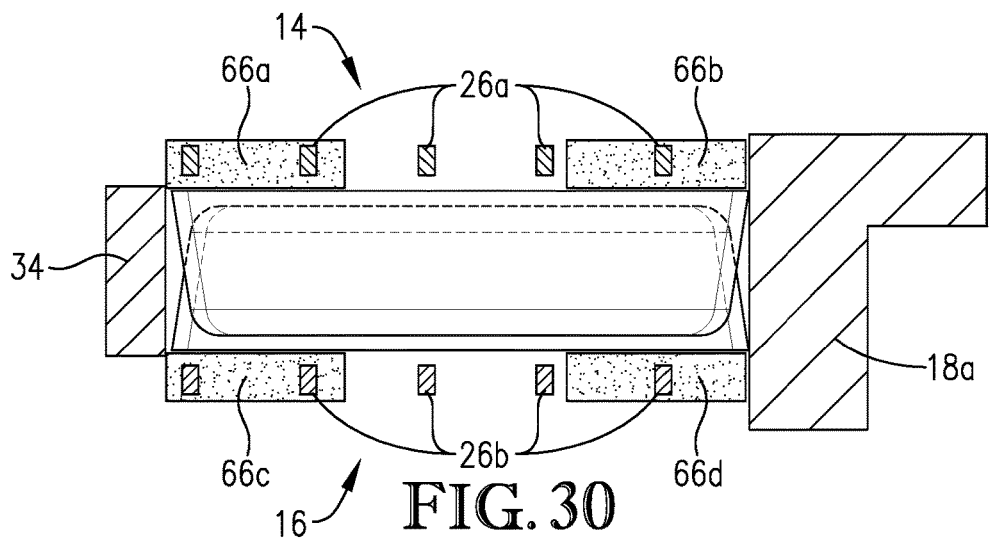
FIG. 30 is a transverse cross sectional view of the carrier shown in FIG. 29.

In some embodiments, carriers of the present invention may further include one or more dielectric field shapers to enhance the uniformity of the microwave field applied to the articles. Dielectric field shapers may be solid, elongated members that extend along the row of articles in a direction generally parallel to the support members. Dielectric field shapers may be formed of a low loss tangent material that can optionally be food-grade. The dielectric field shapers may be formed of the same material used to construct the frame of the carrier, or from a different low loss tangent material. Exemplary dielectric field shapers are shown in FIGS. 29 and 30. As shown in FIGS. 29 and 30, when used, carrier 10 may employ four, spaced apart dielectric field shapers 66a-d, each positioned near a corner of the articles as shown in FIGS. 29 and 30. By locating the field shapers 66a-d in areas of lower heating near the corners, the heating across the upper and lower surfaces of the articles can be enhanced to achieve an average value in the y-direction. In the embodiments shown in FIGS. 29 and 30, some of the support members may be embedded in field shapers 66a-d. In some embodiments, the slats shown in FIGS. 29 and 30 may be electrically conductive as discussed previously. When the carrier includes two or more compartments for housing a single row of articles, each compartment may include a set of four dielectric field shapers as described herein.

According to other embodiments of the present invention, the articles loaded into the carrier may comprise pouches. Any suitable type of pouch can be used and, typically, pouches may be singular pouches that are not attached to any other pouches. Pouches can be flexible, semi-flexible, or rigid, and may be formed of any suitable material, including, for example, including plastics, cellulosics, and other microwave-transparent materials. In some embodiments, the pouches may be gusseted pouches, while in other embodiments, the pouches may be pillow pouches. Pouches processed according to embodiments of the present invention may be filled with foodstuffs, beverages, medical fluids, or pharmaceutical fluids.

Figures 31C, 31D:
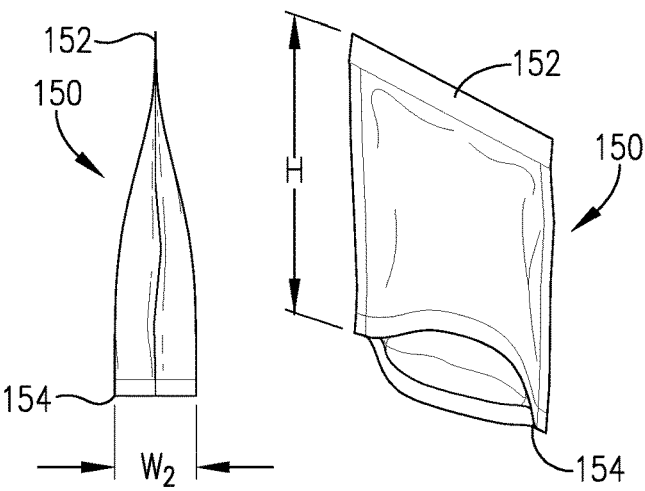
FIG. 31c is a side view of another pouch suitable for use in carriers according to embodiments of the present invention, particularly illustrating another example of a pouch having a base portion that is at least twice as wide as its top portion.
FIG. 31d is an bottom isometric view of the pouch shown in FIG. 31c.

In some embodiments, the pouches loaded into carriers as described herein may be stand-up pouches (SUPS), examples of which are generally shown as pouch 150 in FIGS. 31a-d. Pouch 150 shown in FIGS. 31a and 31b is a side gusset pouch, and pouch 150 shown in FIGS. 31c and 31d is a bottom gusset pouch. Both types may be used in carriers configured as described herein, as well as other types of pouches including, but not limited to, pillow pouches. These pouches may or may not include a spout. As shown in FIG. 31a-d, pouch 150 has a top portion 152 and a base portion 154 that is wider than top portion 152. Base portion 154 of pouch 150 can be at least twice, at least three times, or at least four times wider than top portion 152. In some embodiments, the base portion 154 and top portion 152 have approximately the same width. The width of the top portion 152 of pouch 150, shown as $W_1$ in FIG. 31a, can be at least about 0.01, at least about 0.05, or at least about 0.10 inches and/or not more than about 0.25, not more than about 0.20, or not more than about 0.15 inches, or it can be in the range of from about 0.01 to about 0.25 inches, about 0.05 to about 0.20 inches, or from about 0.10 to about 0.15 inches. In some embodiments, the width of top portion 152 may be at least about 0.5, at least about 0.75, at least about 1, at least about 1.5 and/or not more than about 3, not more than about 2.5, not more than about 2, not more than about 1.5, or not more than about 1 inch, or it can be in the range of from about 0.5 to about 3 inches, about 0.75 to about 2.5 inches, about 1 to about 2 inches, or about 1 to about 1.5 inches.

The width of base portion, shown as $W_2$ in FIGS. 31a and 31c, can be at least about 0.5, at least about 0.75, at least about 1, at least about 1.5 and/or not more than about 3, not more than about 2.5, not more than about 2, not more than about 1.5, or not more than about 1 inch, or it can be in the range of from about 0.5 to about 3 inches, about 0.75 to about 2.5 inches, about 1 to about 2 inches, or about 1 to about 1.5 inches. The height of pouch 150, shown as H in FIGS. 31b and 31d, can be at least about 2, at least about 3, at least about 4, or at least about 4.5 inches and/or not more than about 12, not more than about 10, or not more than about 8 inches, or it can be in the range of from about 2 to about 12 inches, about 3 to about 10 inches, about 4 to about 8 inches.

Because of their shape and flexibility, most types of pouches are difficult to secure during heating. However, it may be undesirable to permit the pouches to move freely within the microwave zone at the risk of developing hot or cold spots within the material being treated. Hot spots may damage the taste, texture, color, and other properties of the material, while cold spots indicate the material was not fully treated. It has been discovered that employing a carrier that includes an upper and lower support structure having at least one recessed surface may be useful for securing pouches within the carrier. As a result, more uniform heating of the pouch contents may be achieved and microwave heating of flexible pouches may be achieved on a larger scale.

Figure 33:
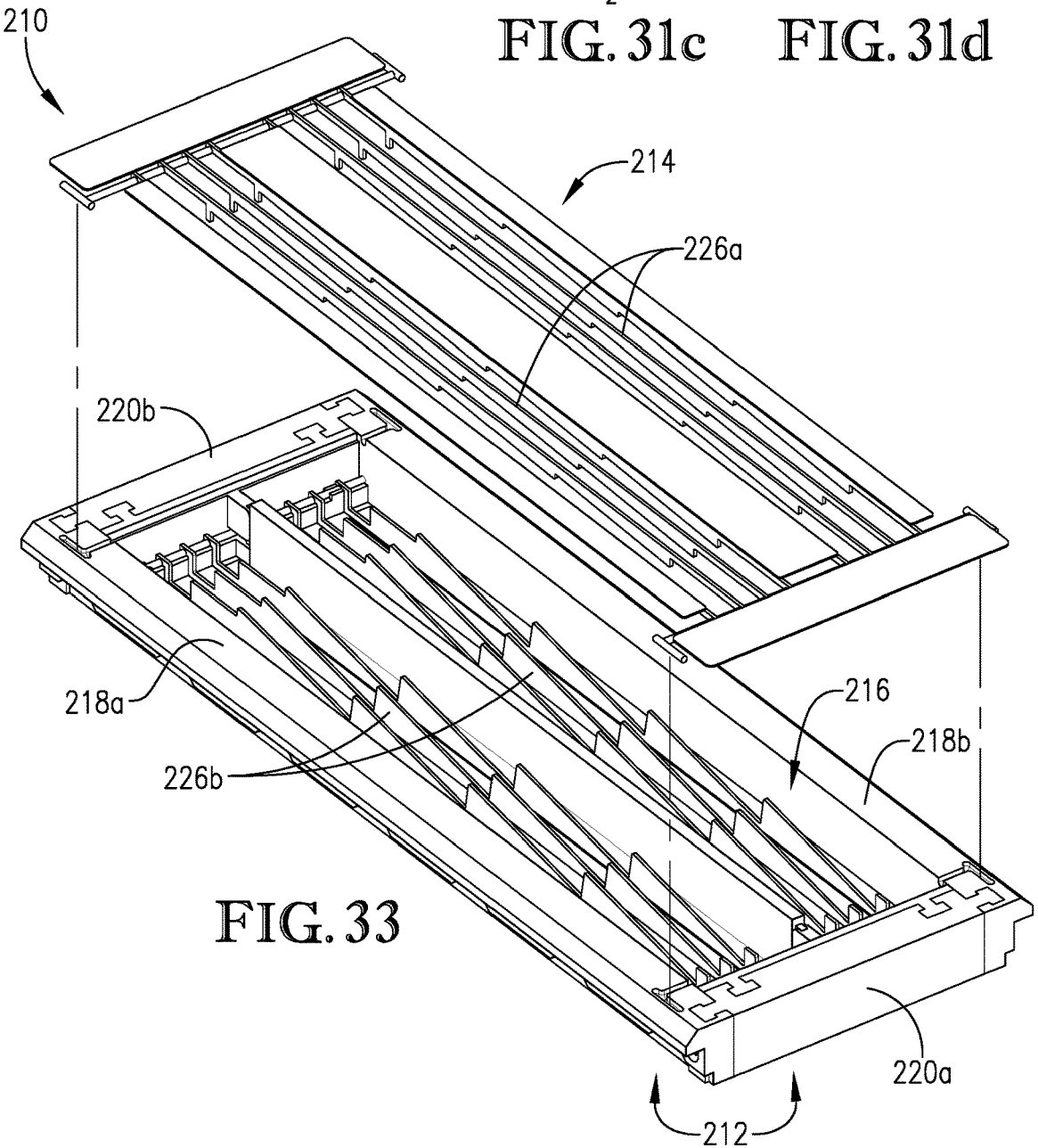
FIG. 33 is an exploded view of the carrier shown in FIG. 32.

Turning now to FIGS. 32 and 33, several views of one embodiment of a carrier 210 suitable for transporting a plurality of pouches on a convey line of a microwave heating system are provided. Carrier 210 may be configured in a similar manner as other carriers described herein including, for example, those described with respect to FIGS. 1-14. For example, as shown in FIGS. 32 and 33, carrier 210 may include an outer frame 212 that comprises first and second spaced apart side members 218a,b configured to engage a convey line (not shown), and first and second spaced apart end members 220a,b coupled to and extending between opposite ends of the first and second side members 218a,b.

As shown in FIGS. 32 and 33, carrier 210 may also include an upper support structure 214 and a lower support structure 216 for securing pouches 150 within the carrier 210. The upper and lower support structures 214, 216 may be configured to extend between the first and second end members 220a,b. In some embodiments, as generally shown in FIGS. 32 and 33, upper and lower support structures 214 and 216 may be formed of respective upper and lower groups 226a, 226b of individual support members, while, in other embodiments, the upper and lower support structures 214 and 216 may be formed from upper and lower grid members or upper and lower sheets of microwave-transparent or semi-transparent material, as discussed previously.

Further, in some embodiments, all or a portion of one or both of upper and lower support structures 214, 216 may be formed of an electrically conductive material as described herein, while, in other embodiments, all or a portion of one or both of upper and lower support structures 214, 216 may be formed of a low loss tangent material. Although not shown in FIGS. 32 and 33, carrier 210 can further include one or more removable article spacing members including vertical spacing members and/or dividers as described previously, that can be selectively inserted to adjust the size and/or shape of the cargo volume within the carrier 210. Additionally, carrier 210 may include one or more dielectric shapers as described herein with respect to FIGS. 26-30.

Figure 34A:
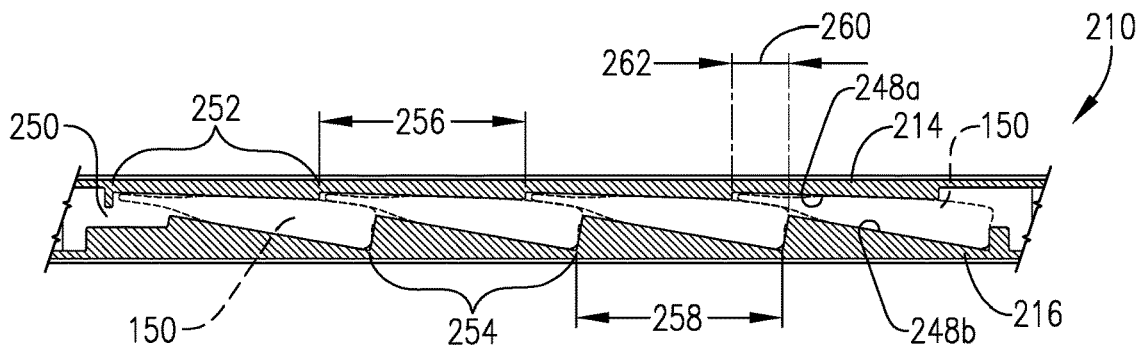
FIG. 34a is a partial longitudinal cross sectional view of a carrier configured according to one or more embodiments of the present invention, particularly illustrating one possible orientation of the pouches within the carrier.
Figure 34B:
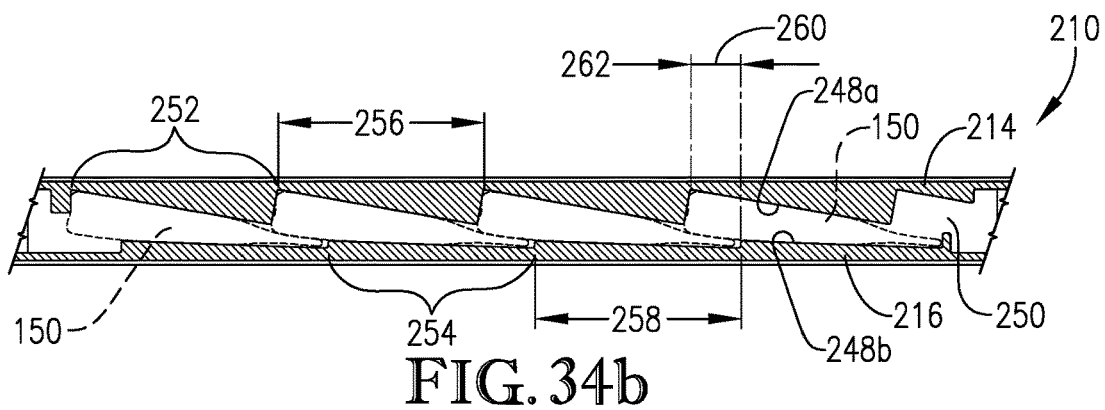
FIG. 34b is a partial longitudinal cross sectional view a carrier configured according to one or more embodiments of the present invention, particularly illustrating another possible orientation of the pouches within the carrier.
Figure 34C:
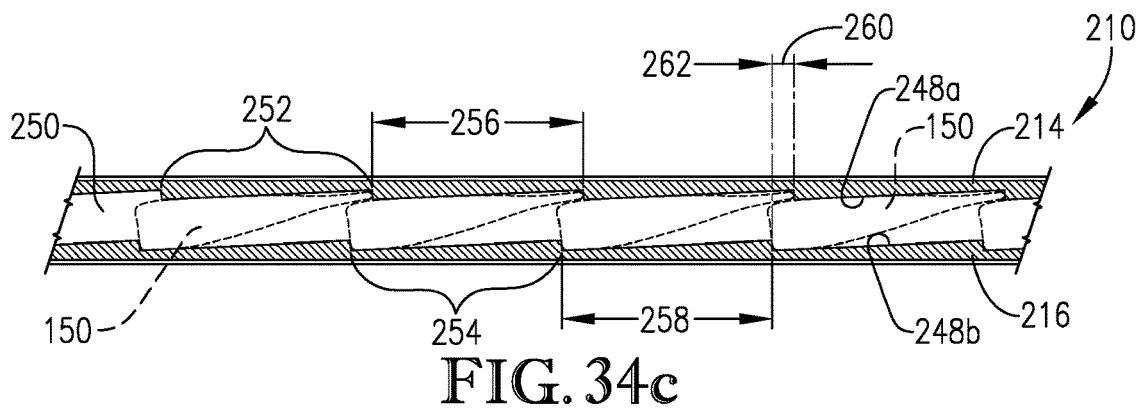
FIG. 34c is a partial longitudinal cross sectional view of a carrier configured according to one or more embodiments of the present invention, particularly illustrating yet another possible orientation of the pouches within the carrier.

Turning now to FIGS. 34a-d, cross sectional views of several carriers suitable for transporting a plurality of pouches according to various embodiments of the present invention are shown. As shown in FIGS. 34a-d the carrier 210 may include a pouch receiving space 250 defined between a downward facing surface of upper support structure 214, shown as surface 248a, and an upward facing surface of lower support structure 216, shown as surface 248b. At least one of downward facing surface 248a and upward facing surface 248b can comprise a series of recesses. In some embodiments, both downward facing surface 248a and upward facing surface 248b may include respective upper and lower recesses 252, 254. Each of upper and lower recesses 252 and 254 may be configured to receive the base portion of one of the pouches 150 in order to secure the pouches 150 into the pouch receiving space 250. In some embodiments, as shown in FIGS. 34a and 34c, one or more of the lower recesses 254 may be configured to receive the base portion one or more of the pouches 150 in a "bottom down" configuration, while, in other embodiments shown, for example, in FIGS. 34b and 34d, one or more of the upper recesses 252 may be configured to receive the base portion of one or more of the pouches 150 in a "bottom up" configuration. When pouches 150 include pillow pouches having, for example, a base portion and a top portion of approximately equal dimensions, one of the base and top portion may be received within the upper recesses 252, while the other of the base and top portion may be received within the lower recesses 254.

In general, each of upper and lower recesses can have a maximum depth of at least about 0.10, at least about 0.25, or at least about 0.40 inches and/or not more than about 2, not more than about 1.75, not more than about 1.5, not more than about 1, not more than about 0.75, or not more than about 0.60 inches, or it can be in the range of from about 0.10 to about 2 inches, about 0.25 to about 1.5 inches, or about 0.40 to about 1 inch.

Figure 34D:
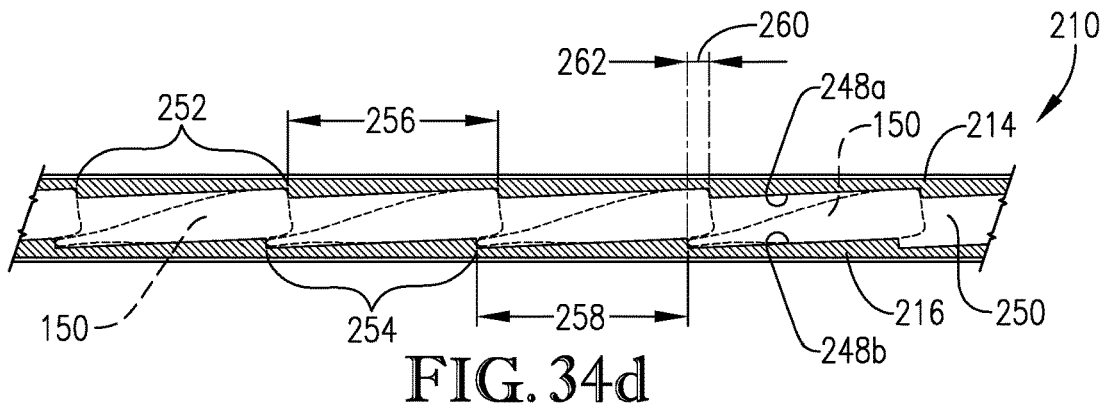
FIG. 34d is a partial longitudinal cross sectional view of a carrier configured according to one or more embodiments of the present invention, particularly illustrating still another possible orientation of the pouches within the carrier.

Each of upper and lower recesses 252, 254 can have the same maximum depth, or one or more of upper or lower recesses 254 can have a different maximum depth than one or more others. For example, in some embodiments, the maximum depth of the lower recesses 254 can be similar to, or substantially the same as, the maximum depth of the upper recesses 252, as generally shown in FIGS. 34c and 34d. For example, in such embodiments, the maximum depth of the lower recesses 254 can be within about 0.15, within about 0.10, within about 0.05, or within about 0.01 inches of the maximum depth of the upper recesses 252. In other embodiments, one of the upper and lower recesses 252, 254 can have a maximum depth greater than the maximum depth of the other of the upper and lower recesses 252, 254, as generally shown in FIGS. 34a and 34b. In some embodiments, the maximum depth of the lower recesses 254 can be at least about 0.20, at least about 0.25, at least about 0.30, or at least about 0.35 inches and/or not more than about 0.75, not more than about 0.60, not more than about 0.50, or not more than about 0.45 inches different than (i.e., higher or lower than) the maximum depth of the upper recesses 252.

Each of upper recesses 252 and lower recesses 254, when present, are spaced apart from one another along the length of carrier 210. As shown in FIGS. 34a-d, adjacent upper recesses 252 may be spaced apart from one another along the length of carrier 210 by an upper recess spacing 256, while adjacent lower recesses 254 may be spaced from one another by a lower recess spacing, shown as 258. In some embodiments, one of upper and lower recess spacing 256 and 258 is larger than the other, while, in other embodiments, upper and lower recess spacing 256 and 258 are substantially the same. In some embodiments, the upper recess spacing 256 and/or the lower recess spacing 258 can be can be at least about 1, at least about 2, at least about 3, or at least about 4 inches and/or not more than about 10, not more than about 8, or not more than about 6 inches, or it can be in the range of from about 1 to about 10 inches, about 2 to about 8 inches, about 2 to about 8 inches, about 3 to about 6 inches in the longitudinal (longest) direction along carrier 210. In some embodiments, the spacing between adjacent ones of upper and lower recesses 252, 254 may be less than the height of the pouches, so that adjacent pouches 150 overlap when loaded into the carrier 210, as generally shown in FIGS. 34a-d.

In some embodiments, upper and lower recesses 252 and 254 may be offset from one another in a direction parallel to the length of carrier 210. As shown in FIG. 34a-d, this forms offset regions 260 between corresponding upper and lower recesses 222, 224. Each of offset regions 260 may have an offset distance 262 that is less than one-half, less than one-third, less than one-fourth, less than one-fifth, or less than one-tenth of the upper or lower recess spacing 256 or 258. In some embodiments, offset distance 262 can be at least about 0.50, at least about 1, or at least about 1.5 inches and/or not more than about 4 inches, not more than about 3 inches, or not more than about 2 inches, or it can be in the range of from about 0.5 to about 4, about 0.5 to about 3 inches, about 1 to about 3 inches, or about 1.5 to about 2 inches.

Figure 35A:
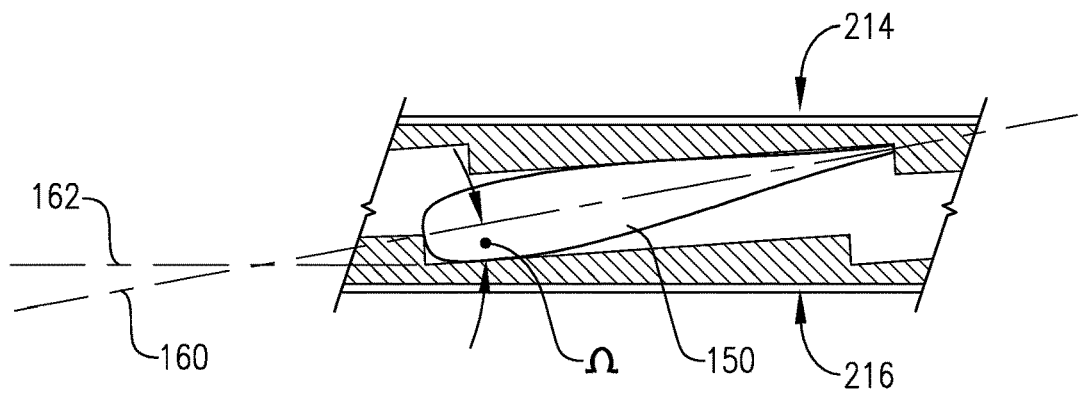
FIG. 35a is a partial longitudinal cross sectional view of a carrier, particularly illustrating the orientation of one type of pouches within the carrier according to certain embodiments of the present invention.
Figure 35B:
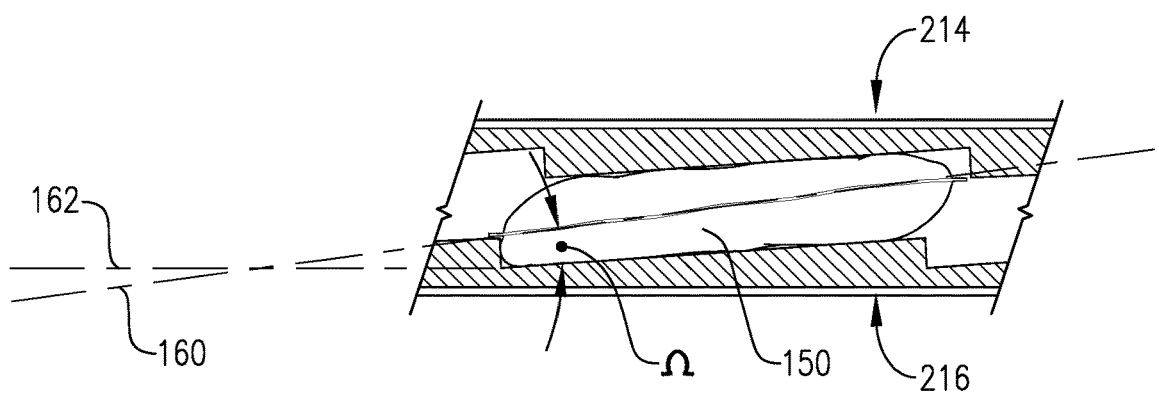
FIG. 35b is a partial longitudinal cross sectional view of a carrier, particularly illustrating the orientation of another type of pouches within the carrier according to certain embodiments of the present invention.

As shown in FIGS. 34a-d and 35a and b, pouch receiving space 250 can be configured to hold pouches 150 in a non-horizontal orientation and a non-vertical orientation. FIG. 35a shows one embodiment where pouch 150 is a stand up pouch, while FIG. 35b shows one embodiment where pouch 150 is a pillow pouch. Accordingly, pouch receiving space 250 may be configured to hold at least one, or all, of pouches 150 at a pouch orientation angle ($\Omega$) defined between a line drawn through the centerline of pouch 150, shown as line 160 in FIGS. 35a and 35b, and the horizontal, or a line parallel to upper or lower support structures 214 or 216 when carrier 210 is loaded onto the convey line, as shown by line 162 in FIGS. 35a and b. In some embodiments, the pouch receiving space can be configured to hold pouches at a pouch orientation angle ($\Omega$) of at least about 5, at least about 10, at least about 15, at least about 20, or at least about 25° and/or not more than about 45, not more than about 45, or not more than about 35°, or it can be in the range of from about 5 to about 45°, about 10 to about 40°, or about 15 to about 35°. At least a portion of the downward facing surface 248a of upper support structure 214 and/or the upward facing surface 248b of lower support structure 216 may be oriented at the same, or a substantially similar, angle as the pouch orientation angle. As used herein, the phrase "substantially similar angle," refers to an angle within 5° of another angle.

As shown in FIGS. 34a-d, offset region 260 can be configured to receive the base portion of one pouch and the top portion of an adjacent pouch when pouches 150 are arranged in an overlapped configuration. It has been discovered that by overlapping the thinner top portion of one pouch with the thicker base portion of an adjacent pouch in offset region 260, hot spots may be prevented and the overall stability of pouches 150 within carrier 210 as carrier 210 moves along the convey line can be significantly improved.

Figure 36A:
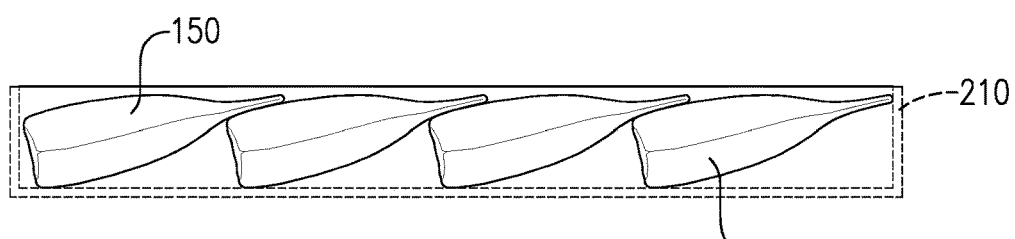
FIG. 36a is a side view of a plurality of pouches arranged in a carrier according to certain embodiments, particularly illustrating a shingled configuration.
Figure 36B:
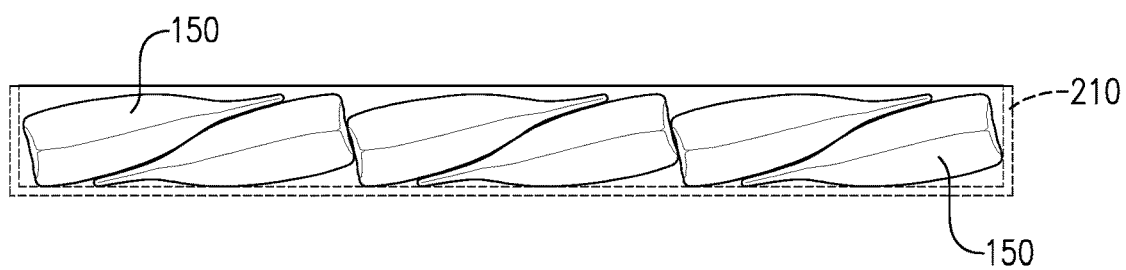
FIG. 36b is a side view of a plurality of pouches arranged in a carrier according to certain embodiments, particularly illustrating a reverse shingled configuration.

Turning now to FIGS. 36a and 36b, other possible arrangements of articles according to embodiments of the present invention are shown. In particular, FIGS. 36a and 36b illustrate possible configurations for pouches 150 within a carrier 210. In the configurations illustrated in FIGS. 36a and 36b, each of the pouches 150 is oriented at substantially the same pouch orientation angle and adjacent pouches 150 overlap one another to form a "shingled" configuration. In this type of configuration, the narrower top portion of one pouch 150 may be positioned over at least a portion of the wider based portion of an adjacent pouch 150. Alternatively, the wider base portion of one pouch may be positioned over at least a portion of the narrower top portion of an adjacent pouch if the direction of the packages were reversed. In a shingled configuration, at least about 10, at least about 15, at least about 20, at least about 25 percent and/or not more than about 50, not more than about 45, not more than about 40, not more than about 35 percent of the pouch overlaps with the adjacent pouch. As shown in FIG. 36a, pouches oriented in a shingled configuration may be oriented in the same direction.

In other embodiments, as shown in FIG. 36b, for example, adjacent pouches 150 may be oriented in opposite directions. When oriented in opposite directions, as shown for example, in FIG. 36b, the top portion of one pouch may be located directly above the bottom portion of an adjacent pouch in a "reverse shingled" configuration. When oriented in a reverse shingled configuration, at least about 30, at least about 40, at least about 50, at least about 60, at least about 70, or at least about 75 percent and/or not more than about 99, not more than about 95, not more than about 90, not more than about 85 percent of one pouch overlaps with the adjacent pouch.

Carriers as described herein are well suited for use with microwave-assisted heating systems that employ liquid-filled microwave heating chambers. One example of such a system is described in U.S. Pat. No. 9,357,590 ("the '590 patent"), the disclosure of which is incorporated herein by reference to the extent not inconsistent with the present disclosure. Another example of a microwave heating system in which carriers of the present invention can be used is described in U.S. Pat. No. 7,119,313. Some embodiments of suitable microwave heating systems will be described in further detail below.

Turning now to FIGS. 37a and 37b, a schematic representation of the major steps in a microwave heating system in which carriers of the present invention may be employed is depicted in FIG. 37a, while FIG. 37b depicts one embodiment of a microwave system 100 operable to heat a plurality of articles according to the process outlined in FIG. 37a. As shown in FIGS. 37a and 37b, one or more articles can initially be introduced into a thermalization zone 112, wherein the articles can be thermalized to a substantially uniform temperature. Once thermalized, the articles can then be optionally passed through a pressure adjustment zone 114a before being introduced into a microwave heating zone 116. In microwave heating zone 116, the articles can be rapidly heated using microwave energy discharged into at least a portion of the heating zone by one or more microwave launchers, generally illustrated as launchers 118 in FIG. 37b. The heated articles can then optionally be passed through an optional holding zone 120, wherein the articles can be maintained at a constant temperature for a specified amount of time. Subsequently, the articles can then be passed to a quench zone 122, wherein the temperature of the articles can be quickly reduced to a suitable handling temperature. Thereafter, the cooled articles can optionally be passed through a second pressure adjustment zone 114b before being removed from system 100 and further utilized.

According to one embodiment of the present invention, each of the above-described thermalization, microwave heating, holding, and/or quench zones 112, 116, 120, and 122 can be defined within a single vessel, as generally depicted in FIG. 37b, while, in another embodiment, at least one of the above-described stages can be defined within one or more separate vessels. According to one embodiment, at least one of the above-described steps can be carried out in a vessel that is at least partially filled with a liquid medium in which the articles being processed can be at least partially submerged. As used herein, the term "filled" denotes a configuration where at least 50 percent of the specified volume is filled with the liquid medium. In certain embodiments, "filled" volumes can be at least about 75 percent, at least about 90 percent, at least about 95 percent, or 100 percent full of the liquid medium.

The liquid medium may have a dielectric constant greater than the dielectric constant of air and, in one embodiment, can have a dielectric constant similar to the dielectric constant of the articles being processed. Water (or liquid media comprising water) may be particularly suitable for systems used to heat edible and/or medical devices or articles. In one embodiment, additives, such as, for example, oils, alcohols, glycols, and salts may optionally be added to the liquid medium to alter or enhance its physical properties (e.g., boiling point) during processing, if needed.

Microwave system 100 can include at least one conveyance system (not shown in FIGS. 37a and 37b) for transporting the articles through one or more of the processing zones described above. Examples of suitable conveyance systems can include, but are not limited to, plastic or rubber belt conveyors, chain conveyors, roller conveyors, flexible or multi-flexing conveyors, wire mesh conveyors, bucket conveyors, pneumatic conveyors, screw conveyors, trough or vibrating conveyors, and combinations thereof. The conveyance system can include any number of individual convey lines and can be arranged in any suitable manner within the process vessels. The conveyance system utilized by microwave system 100 can be configured in a generally fixed position within the vessel or at least a portion of the system can be adjustable in a lateral or vertical direction.

As shown in FIGS. 37a and 37b, the articles introduced into microwave system 100 are initially introduced into thermalization zone 112, wherein the articles are thermalized to achieve a substantially uniform temperature. In one embodiment, at least about 85 percent, at least about 90 percent, at least about 95 percent, at least about 97 percent, or at least about 99 percent of all the articles withdrawn from thermalization zone 112 have a temperature within about 5° C., within about 2° C., or within 1° C. of one another. As used herein, the terms "thermalize" and "thermalization" generally refer to a step of temperature equilibration or equalization. Depending on the initial and desired temperature of the articles being thermalized, the temperature control system of thermalization zone 112, illustrated in FIG. 37a as heat exchanger 113, can be a heating and/or cooling system. In one embodiment, the thermalization step can be carried out under ambient temperature and/or pressure, while, in another embodiment, thermalization can be carried out in a pressurized and/or liquid-filled thermalization vessel at a pressure of not more than about 10 psig, not more than about 5 psig, or not more than about 2 psig. Articles undergoing thermalization can have an average residence time in thermalization zone 112 of at least about 30 seconds, at least about 1 minute, at least about 2 minutes, at least about 4 minutes and/or not more than about 20 minutes, not more than about 15 minutes, or not more than about 10 minutes. In one embodiment, the articles withdrawn from thermalization zone 112 can have a temperature of at least about 20° C., at least about 25° C., at least about 30° C., at least about 35° C. and/or not more than about 70° C., not more than about 65° C., not more than about 60° C., or not more than about 55° C.

In one embodiment wherein thermalization zone 112 and microwave heating zone 116 are operated at substantially different pressures, the articles removed from thermalization zone 112 can first be passed through a pressure adjustment zone 114a before entering microwave heating zone 116, as generally depicted in FIGS. 37a and 37b. Pressure adjustment zone 114a can be any zone or system configured to transition the articles being heated between an area of lower pressure and an area of higher pressure. In one embodiment, pressure adjustment zone 114a can be configured to transition the articles between two zones having a pressure difference of at least about 1 psi, at least about 5 psi, at least about 10 psi and/or not more than about 50 psi, not more than about 45 psi, not more than about 40 psi, or not more than about 35 psi. In one embodiment, microwave system 100 can include at least two pressure adjustment zones 114a,b to transition the articles from an atmospheric pressure thermalization zone to a heating zone operated at an elevated pressure before returning the articles back to atmospheric pressure, as described in detail below.

Referring again to FIGS. 37a and 37b, the articles exiting thermalization zone 112, and optionally passed through pressure adjustment zone 114a, as described above, can then be introduced into microwave heating zone 116. In microwave heating zone 116, the articles can be rapidly heated with a heating source that uses microwave energy. As used herein, the term "microwave energy" refers to electromagnetic energy having a frequency between 300 MHz and 30 GHz. In one embodiment, various configurations of microwave heating zone 116 can utilize microwave energy having a frequency of about 915 MHz or a frequency of about 2.45 GHz, both of which have been generally designated as industrial microwave frequencies. In addition to microwave energy, microwave heating zone 116 may optionally utilize one or more other heat sources such as, for example, conductive or convective heating or other conventional heating methods or devices. However, at least about 85 percent, at least about 90 percent, at least about 95 percent, or substantially all of the energy used to heat the articles within microwave heating zone 116 can be microwave energy from a microwave source.

According to one embodiment, microwave heating zone 116 can be configured to increase the temperature of the articles above a minimum threshold temperature. In one embodiment wherein microwave system 100 is configured to sterilize a plurality of articles, the minimum threshold temperature (and operating temperature of microwave heating zone 116) can be at least about 65° C., at least about 70° C., at least about 75° C., at least about 80° C., at least about 85° C., at least about 90° C., at least about 95° C., at least about 100° C., at least about 105° C., at least about 110° C., at least about 115° C., at least about 120° C., at least about 121° C., at least about 122° C. and/or not more than about 130° C., not more than about 128° C., or not more than about 126° C. Microwave heating zone 116 can be operated at approximately ambient pressure, or it can include one or more pressurized microwave chambers operated at a pressure of at least about 5 psig, at least about 10 psig, at least about 15 psig and/or not more than about 80 psig, not more than about 60 psig, or not more than about 40 psig. In one embodiment, the pressurized microwave chamber can be a liquid-filled chamber having an operating pressure such that the articles being heated can reach a temperature above the normal boiling point of the liquid medium employed therein.

The articles passing through microwave heating zone 116 can be heated to the desired temperature in a relatively short period of time, which, in some cases, may minimize damage or degradation of the articles. In one embodiment, the articles passed through microwave heating zone 116 can have an average residence time of at least about 5 seconds, at least about 20 seconds, at least about 60 seconds and/or not more than about 10 minutes, not more than about 8 minutes, not more than about 5 minutes, not more than about 3 minutes, not more than about 2 minutes, or not more than about 1 minute. In the same or other embodiments, microwave heating zone 116 can be configured to increase the average temperature of the articles being heated by at least about 20° C., at least about 30° C., at least about 40° C., at least about 50° C., at least about 75° C. and/or not more than about 150° C., not more than about 125° C., or not more than about 100° C., at a heating rate of at least about 15° C. per minute (° C./min), at least about 25° C./min, at least about 35° C./min and/or not more than about 75° C./min, not more than about 50° C./min, or not more than about 40° C./min.

Figure 38:
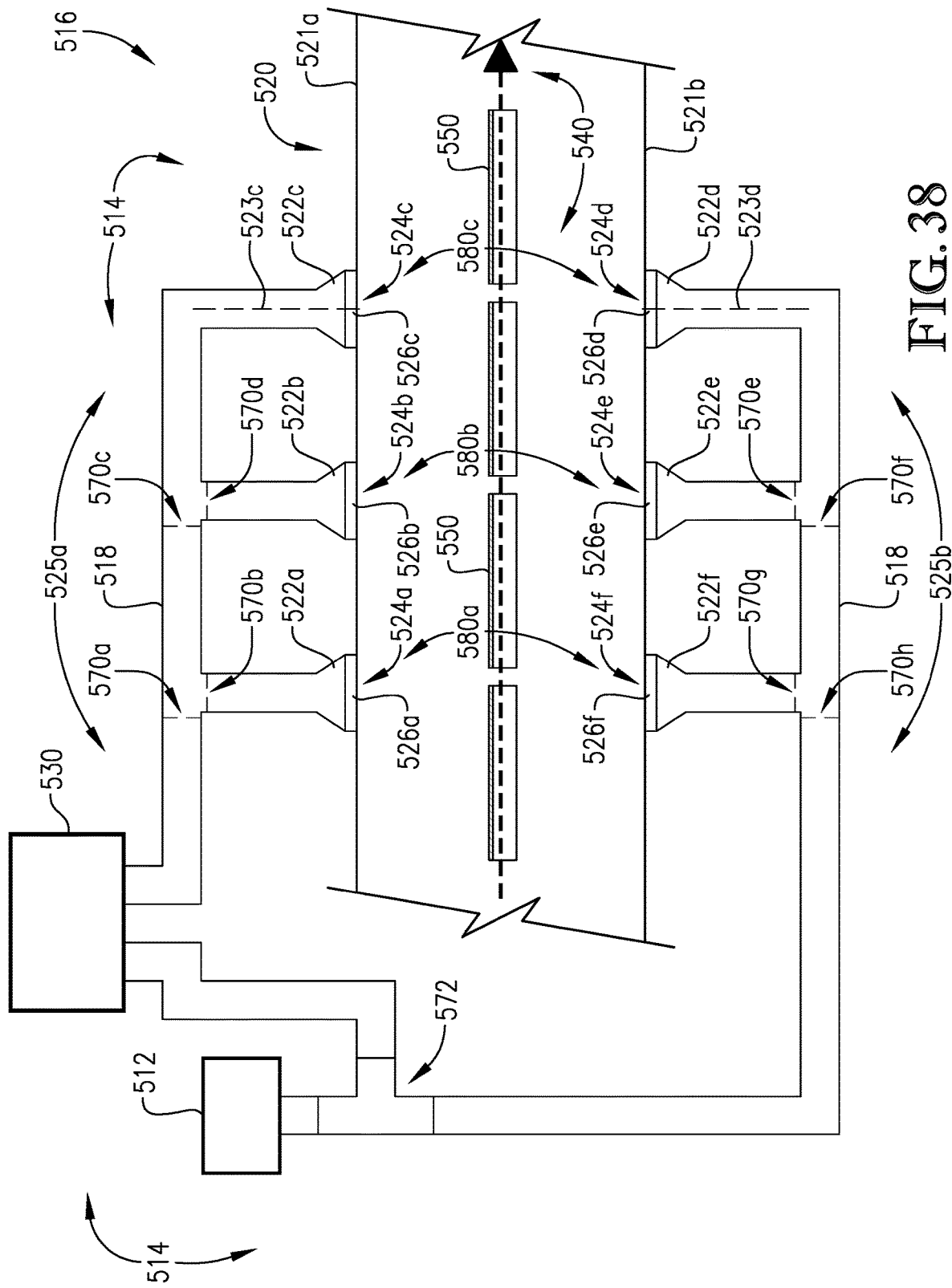
FIG. 38 is a schematic partial side cut-away view of a microwave heating zone configured according to one embodiment of the present invention, particularly illustrating the heating vessel and the microwave distribution system.

Turning now to FIG. 38, one embodiment of a microwave heating zone 516 is illustrated as generally comprising a microwave heating chamber 520, at least one microwave generator 512 for generating microwave energy and a microwave distribution system 514 for directing at least a portion of the microwave energy from generator 512 to microwave chamber 520. Microwave distribution system 514 comprises a plurality of waveguide segments 518 and one or more microwave launchers, shown as launchers 522a-f in FIG. 38, for discharging microwave energy into the interior of microwave chamber 520. As shown in FIG. 38, microwave heating zone 516 can further comprise a conveyance system 540 for transporting carriers 550 loaded with articles to be heated through microwave chamber 520. Each of the components of microwave heating zone 516, according to various embodiments of the present invention, are now discussed in detail immediately below.

Microwave generator 512 can be any suitable device for generating microwave energy of a desired wavelength ($\lambda$). Examples of suitable types of microwave generators can include, but are not limited to, magnetrons, klystrons, traveling wave tubes, and gyrotrons. Although illustrated in FIG. 38 as including a single generator 512, it should be understood that microwave heating zone 516 can include any number of generators arranged in any suitable configuration. For example, in one embodiment, microwave heating zone 516 can include at least 1, at least 2, at least 3 and/or not more than 5, not more than 4, or not more than 3 microwave generators, depending on the size and arrangement of microwave distribution system 514.

Microwave chamber 520 can be any chamber or vessel configured to receive a plurality of articles. Microwave chamber 520 can be of any size and may have one of a variety of different cross sectional shapes. For example, in one embodiment, chamber 520 can have a generally circular or elliptical cross section, while, in other embodiments, can have a generally square, rectangular, or polygonal cross sectional shape. In one embodiment, microwave chamber 520 can be a pressurized chamber and, in the same or other embodiments, can be configured to be at least partially filled with a liquid medium (a liquid-filled chamber). Microwave chamber 520 can also be configured to receive at least a portion of the microwave energy discharged from one or more microwave launchers 522 and, in one embodiment, can be configured to permit the creation of a stable (or standing) wave pattern therein. In one embodiment, at least one dimension of microwave chamber 520 can be at least about 0.30$\lambda$, at least about 0.40$\lambda$, or at least about 0.50$\lambda$, wherein $\lambda$ is the wavelength of the microwave energy discharged therein.

Microwave distribution system 514 comprises a plurality of waveguides or waveguide segments 518 for directing at least a portion of the microwave energy from generator 512 to microwave chamber 520. Waveguides 518 can be designed and constructed to propagate microwave energy in a specific predominant mode, which may be the same as or different than the mode of the microwave energy generated by generator 512. As used herein, the term "mode" refers to a generally fixed cross sectional field pattern of microwave energy. In one embodiment of the present invention, waveguides 518 can be configured to propagate microwave energy in a $TE_{xy}$ mode, wherein x and y are integers in the range of from 0 to 5. In another embodiment of the present invention, waveguides 518 can be configured to propagate microwave energy in a $TM_{ab}$ mode, wherein a and b are integers in the range of from 0 to 5. It should be understood that, as used herein, the above-defined ranges of a, b, x, and y values as used to describe a mode of microwave propagation are applicable throughout this description. In one embodiment, the predominant mode of microwave energy propagated through waveguides 518 and/or discharged via launchers 522a-f can be selected from the group consisting of $TE_{10}$, $TM_{01}$, and $TE_{11}$.

As shown in FIG. 38, microwave distribution system 514 further comprises one or more microwave launchers 522a-f, each defining at least one launch opening 524a-f for discharging microwave energy into microwave chamber 520. Although illustrated in FIG. 38 as comprising six microwave launchers 522a-f, it should be understood that microwave distribution system 514 can include any suitable number of launchers arranged in any desirable configuration. For example, microwave distribution system 514 can include at least 1, at least 2, at least 3, at least 4 and/or not more than 50, not more than 30, or not more than 20 microwave launchers. Launchers 522a-f can be the same or different types of launchers and, in one embodiment, at least one of launchers 522a-f can be replaced with a reflective surface (not shown) for reflecting at least a portion of the microwave energy discharged from the other launchers 522 into microwave heating chamber 520.

When microwave distribution system 514 includes two or more launchers, at least some of the launchers may be disposed on generally the same side of microwave chamber 520. As used herein, the term "same-side launchers" refers to two or more launchers positioned on generally the same side of a microwave chamber. Two or more of the same-side launchers may also be axially spaced from one another. As used herein, the term "axially spaced" denotes spacing in the direction of conveyance of the articles through the microwave system (i.e., spacing in the direction of extension of the convey axis). Additionally, one or more launchers 522 may also be laterally spaced from one or more other launchers 522 of the system. As used herein, the term "laterally spaced" shall denote spacing in the direction perpendicular to the direction of conveyance of the articles through the microwave system (i.e., spacing perpendicular to the direction of extension of the convey axis). For example, in FIG. 38, launchers 522a-c and 522d-f are disposed on respective first and second sides 521a,b of microwave chamber 520 and launcher 522a is axially spaced from launcher 522b and 522c, just as launcher 522e is axially spaced from launchers 522f and 522d.

Additionally, as shown in the embodiment depicted in FIG. 38, microwave distribution system 514 can comprise at least two (e.g., two or more) pairs of oppositely disposed or opposed launchers. As used herein, the term "opposed launchers" refers to two or more launchers positioned on generally opposite sides of a microwave chamber. In one embodiment, the opposed launchers may be oppositely facing. As used herein with respect to opposed microwave launchers, the term "oppositely facing" shall denote launchers whose central launch axes are substantially aligned with one another. For simplicity, central launch axis 523c of launcher 522c and central launch axis 523d of launcher 522d are the only central launch axes illustrated in FIG. 38. However, it should be understood that each of launchers 522a-f include a similar launch axes.

Opposed launchers may be generally aligned with one another, or may be staggered from one or more other launchers disposed on the opposite side of microwave chamber 520. In one embodiment, a pair of opposed launchers may be a staggered pair of launchers, such that the discharge openings 524 of the launchers 522 are not in substantial alignment with one another. Launchers 522a and 522e constitute one exemplary pair of opposed launchers arranged in a staggered configuration. Staggered opposed launchers may be axially or laterally staggered from one another. As used herein with respect to opposed microwave launchers, the term "axially staggered" shall denote launchers whose central launch axes are axially spaced from one another. As used herein with respect to opposed microwave launchers, the term "laterally staggered" shall denote launchers whose central launch axes are laterally spaced from one another. In another embodiment, a pair of opposed launchers may be directly opposite launchers, such that the discharge openings of the launcher pair are substantially aligned. For example, launchers 522c and 522d shown in FIG. 38 are configured as a pair of opposite launchers.

Figure 39:
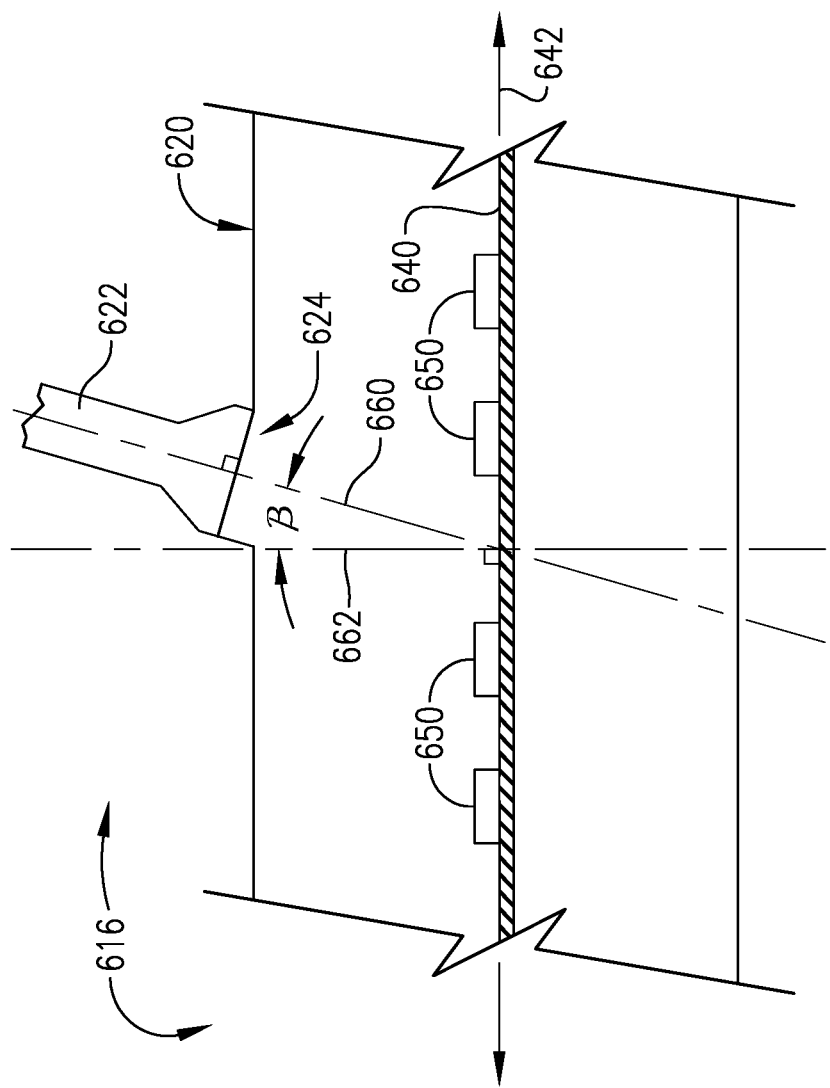
FIG. 39 is a partial side cut-away view of a microwave heating zone configured according to one embodiment of the present invention, particularly illustrating a titled microwave launcher and showing what is meant by the term "launch tilt angle" (β)

Turning now to FIG. 39, a partial view of one embodiment of a microwave heating zone 616 is shown. Microwave heating zone 616 includes at least one microwave launcher 622 that defines a launch opening 624 for discharging energy into a microwave chamber 620. As shown in FIG. 39, microwave launcher 622 is configured to discharge microwave energy along a central launch axis 660 toward a conveyance system 640 configured to transport a plurality of articles 650 within microwave chamber 620 along a convey axis 642. In one embodiment, central launch axis 660 can be tilted such that a launch tilt angle, $\beta$, is defined between central launch axis 660 and a plane normal to convey axis 642, illustrated as plane 662 in FIG. 39. According to one embodiment, launch tilt angle $\beta$ can be at least about 2°, at least about 4°, at least about 5° and/or not more than about 15°, not more than about 10°, or not more than about 8°. When the system includes two or more launchers, a portion of all can be tilted.

As discussed previously, the microwave launchers 522a-f depicted in FIG. 38 may be of any suitable configuration. In some embodiments, the microwave launchers 522a-f may be configured to emit polarized microwave energy. Several views of a microwave launcher 822 configured according to one embodiment of the present invention to emit polarized energy are provided in FIGS. 40a-f. It has been discovered that when the polarization plane of emitted microwave energy is substantially perpendicular to the direction of extension of the support members (or, in some embodiments, slats) of the carrier, the electrically conductive slats in the carrier act to enhance field uniformity in the cargo volume of the carrier, without causing arcing or undue energy loss. In microwave systems of the present invention, the plane of polarization of the microwave energy emitted from the microwave launchers can be perpendicular to the direction of travel of the convey line.

Referring initially to FIG. 40a, microwave launcher 822 is illustrated as comprising a set of opposing sidewalls 832a,b and a set of opposing end walls 834a,b, which collectively define a substantially rectangular launch opening 838. When launch opening 838 comprises a rectangular-shaped opening, it can have a width ($W_1$) and a depth ($D_1$) defined, at least in part, by the terminal edges of sidewalls 832a,b and 834a,b, respectively. In one embodiment, sidewalls 832a,b can be broader than end walls 834a,b such that the length of the lower terminal edge of side walls 832a,b, shown as $W_1$ in FIG. 40a, can be greater than the length of the lower terminal edge of end walls 834a,b, depicted in FIG. 40a with the identifier $D_1$. As shown in FIG. 40a, the elongated portion of side walls 832a,b and end walls 834a,b can also collectively define a pathway 837 through which microwave energy can propagate as it passes from the microwave inlet 836 to the at least one launch opening 838 defined by launcher 822.

One way to achieve polarization of the microwave energy emitted from the microwave launchers is for the inlet of the launcher 822 to be connected to the outlet of a rectangular waveguide propagating microwave energy in a $TE_{10}$ mode. In such a configuration, the polarization plane of the microwave energy emitted from the launcher will be parallel to the smaller rectangular dimension of the waveguide outlet and launcher inlet, shown in FIGS. 40a and 40c-e as depth $D_0$.

When used to discharge microwave energy into a microwave chamber, launch opening 838 can be can be elongated in the direction of extension of the microwave chamber (not shown) or in the direction of convey of the articles therein. For example, in one embodiment, side walls 832a,b and end walls 834a,b of launcher 822 can be configured such that the maximum dimension of launch opening 838 (shown in FIG. 40a as $W_1$) can be aligned substantially parallel to the direction of extension of the microwave chamber and/or to the direction of convey of articles passing therethrough. In this embodiment, the terminal edges of side walls 832a,b can be oriented parallel to the direction of extension (or the direction of convey), while the terminal edges of end walls 834a,b may be aligned substantially perpendicular to the direction of extension or convey within the microwave chamber (not shown in FIG. 40).

Figure 40E:
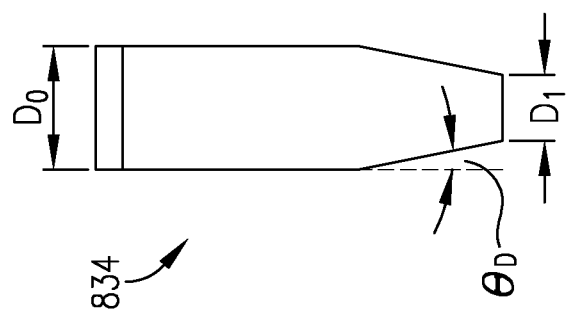
FIG. 40e is an end view of yet another embodiment of the microwave launchers generally depicted in FIGS. 40a and 40b, particularly illustrating a launcher having a tapered outlet.
Figure 40D:
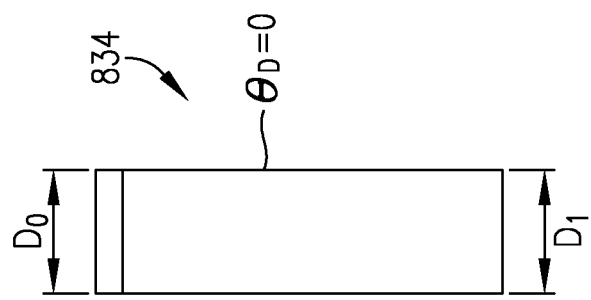
FIG. 40d is an end view of another embodiment of the microwave launcher generally depicted in FIGS. 40a and 40b, particularly illustrating a launcher having an inlet and outlet of approximately the same size.
Figure 40C:
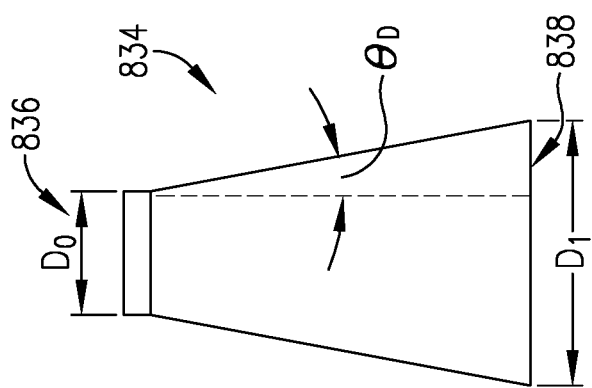
FIG. 40c is an end view of the microwave launcher depicted in FIGS. 39a and 39b, particularly illustrating a launcher having a flared outlet.

FIGS. 40b and 40c respectively provide views of a sidewall 832 and end wall 834 of microwave launcher 822 illustrated in FIG. 40a. It should be understood that, while only one of the side or end walls 832, 834 are shown in FIGS. 40b and 40c, the other of the pair could have a similar configuration. In one embodiment, at least one of side wall 832 and end wall 834 can be flared such that the inlet dimension (width $W_0$ or depth $D_0$) is smaller than the outlet dimension (width $W_1$ or depth $D_1$), as respectively illustrated in FIGS. 40b and 40c. When flared, each of side and end walls 832, 834 define respective width and depth flare angles, $\theta_w$ and $\theta_d$, as shown in FIGS. 40b and 40c. In one embodiment, width and/or depth flare angles $\theta_w$ and/or $\theta_d$ can be at least about 2°, at least about 5°, at least about 10°, or at least about 15° and/or not more than about 45°, not more than about 30°, or not more than about 15°. In one embodiment, the width and depth flare angles $\theta_w$ and $\theta_d$ can be the same, while, in another embodiment, the values for $\theta_w$ and $\theta_d$ may be different.

According to one embodiment, depth flare angle $\theta_d$ can be smaller than width flare angle $\theta_w$. In certain embodiments, depth flare angle $\theta_d$ can be not more than about 0°, such that the inlet depth $D_0$ and the outlet dimension $D_1$ of microwave launcher 822 are substantially the same, as illustrated in the embodiment depicted in FIG. 40d. In another embodiment, the depth flare angle $\theta_d$ may be less than 0°, such that $D_1$ is smaller than $D_0$, as shown in FIG. 40e. When microwave launcher 822 comprises a depth flare angle less than 0° and/or the depth $D_1$ of launch opening 838 is smaller than the depth $D_0$ of microwave inlet 836, microwave launcher 822 can be a tapered launcher having a generally inverse profile. In one embodiment wherein microwave launcher 822 comprises n launch openings, between 1 and n of the openings can have a depth and/or width less than or equal to the depth and/or width of the inlet of the launcher. Further embodiments of multi-opening launchers will be discussed in detail below.

According to one embodiment of the present invention, the depth $D_1$ of launch opening 838 can be no more than about 0.625λ, not more than about 0.5λ, not more than about 0.4λ, not more than about 0.35λ, or not more than about 0.25λ, wherein λ is the wavelength of the predominant mode of microwave energy discharged from launch opening 838. Although not wishing to be bound by theory, it is believed that minimizing the depth $D_1$ of launch opening 838, the microwave field created proximate launch opening 838 is more stable and uniform than would be created by launchers having greater depths. In one embodiment wherein microwave launcher 822 comprises n launch openings, the depth of each launch opening, $d_n$, can be not more than about 0.625λ, not more than about 0.5λ, not more than about 0.4λ, not more than about 0.35λ, or not more than about 0.25λ. When microwave launcher 822 has multiple openings, each opening can have a depth that is the same or different than one or more of the other launch openings of the same launcher.

One embodiment of a microwave launcher 1022 including an inductive iris disposed therein is shown in FIGS. 41a and 41b. Launcher 1022 may include at least one inductive iris 1070 located between its microwave inlet 1036 and one or more launch openings 1038, as generally illustrated in FIGS. 41a and 41b. As shown in FIGS. 41a and 41b, iris 1070 may be defined by a pair of inductive iris panels 1072a,b disposed on opposite sides of launcher 1022. Although illustrated as being coupled to narrower opposing end walls 1034a,b of launcher 1022, it should be understood that first and second iris panels 1072a,b could also be coupled to broader opposing side walls 1032a,b of launcher 1022. As shown in FIGS. 41a and 41b, first and second iris panels 1072a,b extend inwardly into the microwave pathway 1037 defined between microwave inlet 1036 and launch opening 1038 in a direction that is generally transverse to the direction of microwave propagation through pathway 1037. In one embodiment, iris panels obstruct at least about 25 percent, at least about 40 percent, or at least about 50 percent and/or not more than about 75 percent, not more than about 60 percent, or not more than about 55 percent of the total area of microwave pathway 1037 at the location at which they are disposed.

As shown in FIG. 41a, first and second iris panels 1072a,b can be substantially co-planar and can be oriented substantially normal to the central launch axis of microwave launcher 1022. In certain embodiments, the iris panels 1072a,b may be spaced from both the microwave inlet 1036 and the launch opening 1038 of microwave launcher 1022. For example, the iris panels 1072a,b can be spaced from microwave inlet 1036 of launcher 1022 by at least about 10 percent, at least about 25 percent, or at least about 35 percent of the minimum distance between microwave inlet 1036 and launch opening 1038 of launcher 1022. Further, iris panels 1072a,b can be spaced from launch opening 1038 of launcher 1022 by at least about 10 percent, 25 percent, or 35 percent of the maximum distance (L) measured between microwave inlet 1036 and launch opening 1038 of launcher 1022.

Turning back to FIG. 38, at least one of launch openings 524a-f of launchers 522a-f of microwave heating zone 516 can be at least partially covered by a substantially microwave-transparent window 526a-f disposed between each launch opening 524a-f and microwave chamber 520. Microwave-transparent windows 526a-f can be operable to prevent fluid flow between microwave chamber 520 and microwave launchers 522a-f while still permitting a substantial portion of the microwave energy from launchers 522a-f to pass therethrough. Windows 526a-f can be made of any suitable material, including, but not limited to one or more thermoplastic or glass material such as glass-filled Teflon, polytetrafluoroethylene (PTFE), poly(methyl methacrylate (PMMA), polyetherimide (PEI), aluminum oxide, glass, and combinations thereof. In one embodiment, windows 526a-f can have an average thickness of at least about 4 mm, at least about 6 mm, at least about 8 mm and/or not more than about 20 mm, not more than about 16 mm, or not more than about 12 mm and can withstand a pressure difference of at least about 40 psi, at least about 50 psi, at least about 75 psi and/or not more than about 200 psi, not more than about 150 psi, or not more than about 120 psi without breaking, cracking, or otherwise failing.

Microwave heating zone 116 shown in FIGS. 37a and 37b may further include any number of suitable control mechanisms or other devices to monitor and control the temperature of the articles and/or liquid within the microwave heating zone 116. In some embodiments, microwave heating zone 116 (and, optionally, thermalization zone 112 and/or hold zone 120) may include agitation devices, such as fluid jets, for increasing the heat transfer to the articles. Other suitable devices, such as temperature and flow controllers, may also be used to maximize heating of the articles in a minimal time.

As shown in FIGS. 37a and 37b, after being withdrawn from microwave heating zone 116, the heated articles can then optionally be routed to a temperature holding zone 120, wherein the temperature of the articles can be maintained at or above a certain minimum threshold temperature for a specified residence time. As a result of this holding step, the articles removed from holding zone 120 can have a more consistent heating profile and fewer cold spots. In one embodiment, the minimum threshold temperature within holding zone 120 can be the same as the minimum temperature required within microwave heating zone 116 and can be at least about 120° C., at least about 121° C., at least about 122° C. and/or not more than about 130° C., not more than about 128° C., or not more than about 126° C. The average residence time of articles passing through holding zone 120 can be at least about 1 minute, at least about 2 minutes, or at least about 4 minutes and/or not more than about 20 minutes, not more than about 16 minutes, or not more than about 10 minutes. Holding zone 120 can be operated at the same pressure as microwave heating zone 116 and can, in one embodiment, be at least partially defined within a pressurized and/or liquid-filled chamber or vessel. In some embodiment, system 100 does not include a holding zone and the articles are routed from the microwave energy zone to the cooling zone.

After exiting holding zone 120, when present, or microwave heating zone 116 when no holding zone is present, the heated articles of microwave system 100 can subsequently be introduced into a quench zone 122, wherein the heated articles can be quickly cooled via contact with one or more cooled fluids. In one embodiment, quench zone 122 can be configured to cool the articles by at least about 30° C., at least about 40° C., at least about 50° C. and/or not more than about 100° C., not more than about 75° C., or not more than about 50° C. in a time period of at least about 1 minute, at least about 2 minutes, at least about 3 minutes and/or not more than about 10 minutes, not more than about 8 minutes, or not more than about 6 minutes. Any suitable type of fluid can be used as a cooling fluid in quench zone 122, including, for example, a liquid medium such as those described previously with respect to microwave heating zone 116 and/or a gaseous medium, such as air.

According to one embodiment generally depicted in FIGS. 37a and 37b, microwave heating system 100 may also include a second pressure adjustment zone 114b disposed downstream of microwave heating zone 116 and/or holding zone 120, when present. Second pressure adjustment zone 114b may be configured and operated in a manner similar to that previously described with respect to first pressure adjustment zone 114a. When present, second pressure adjustment zone 114b can be located downstream of quench zone 122, such that a substantial portion or nearly all of quench zone 122 is operated at an elevated (super atmospheric) pressure similar to the pressure under which microwave heating zone 116 and/or holding zone 120 are operated. In another embodiment, second pressure adjustment zone 114b can be disposed within quench zone 122, such that a portion of quench zone 122 can be operated at a super-atmospheric pressure similar to the pressure of microwave heating zone 116 and/or holding zone 120, while another portion of quench zone 122 can be operated at approximately atmospheric pressure. When removed from quench zone 122, the cooled articles can have a temperature of at least about 20° C., at least about 25° C., at least about 30° C. and/or not more than about 70° C., not more than about 60° C., or not more than about 50° C. Once removed from quench zone 122, the cooled, treated articles can then be removed from microwave heating zone 110 for subsequent storage or use.

Microwave heating systems of the present invention can be commercial-scale heating systems capable of processing a large volume of articles in a relatively short time. In contrast to conventional retorts and other small-scale systems that utilize microwave energy to heat a plurality of articles, microwave heating systems as described herein can be configured to achieve an overall production rate of at least about 10 packages per minute, at least about 15 packages per minute per convey line, at least about 20 packages per minute per convey line, at least about 25 packages per minute per convey line, or at least about 30 packages per minute per convey line, which far exceeds rates achievable by other microwave systems.

As used herein, the term "packages per minute" refers to the total number of whey gel-filled 8-oz MRE (meals ready to eat) packages able to be processed by a given microwave heating system, according to the following procedure: An 8-oz MRE package filled with whey gel pudding commercially available from Ameriqual Group LLC (Evansville, Ind., USA) is connected to a plurality of temperature probes positioned in the pudding at five equidistant locations spaced along each of the x-, y-, and z-axes, originating from the geometrical center of the package, as shown in FIG. 42. The package is then placed in a microwave heating system being evaluated and is heated until each of the probes registers a temperature above a specified minimum temperature (e.g., 120° C. for sterilization systems). The time required to achieve such a temperature profile, as well as physical and dimensional information about the heating system, can then be used to calculate an overall production rate in packages per minute.

Definitions

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "including," "includes," and "include" have the same open-ended meaning as "comprising," "comprises," and "comprise."

As used herein, the terms "having," "has," and "have" have the same open-ended meaning as "comprising," "comprises," and "comprise."

As used herein, the terms "containing," "contains," and "contain" have the same open-ended meaning as "comprising," "comprises," and "comprise."

As used herein, the terms "a," "an," "the," and "said" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The preferred forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention.

The inventors hereby state their intent to rely on the Equivalents to determine and assess the reasonably fair scope of the present invention as pertains to any apparatus not materially departing from but outside the literal scope of the invention as set forth in the following claims.

The invention claimed is:

1. A carrier for transporting a plurality of articles on a convey line of a microwave heating system, wherein each of said articles comprises a pouch having a base portion and a top portion, where said base portion is at least twice as thick as said top portion, said carrier comprising:
   a frame comprising first and second spaced apart end members; and
   an upper support structure and a lower support structure extending between said first and said second end members and configured to secure said articles in said carrier,
   wherein:
      a pouch receiving space is defined between an upward facing surface of said lower support structure and a downward facing surface of said upper support structure,
      said downward facing surface presents a series of upper recesses spaced from one another by an upper recess spacing,
      said upward facing surface presents a series of lower recesses spaced from one another by a lower recess spacing and said upper recesses, and
      each of said lower recesses is configured to receive the base portion of one of said pouches so as to secure the pouch in said pouch receiving space.

2. The carrier of claim 1, wherein said upper recess spacing and said lower recess spacing are substantially the same.

3. The carrier of claim 1, wherein said upper and lower recesses are offset from one another to form an offset region between said upper and lower recesses, and wherein said offset region is configured to receive a base portion of one of said pouches and a top portion of an adjacent pouch in an overlapped configuration.

4. The carrier of claim 1, wherein said lower recess spacing and said upper recess spacing are less than a height of said pouches so that adjacent pouches loaded in said pouch receiving space overlap one another.

5. The carrier of claim 1, wherein said upper recesses and said lower recesses are offset from one another by an offset distance and wherein said offset distance is less than one-third of said upper and said lower recess spacing.

6. The carrier of claim 5, wherein said offset distance is in the range of from 0.5 to 3 inches and wherein at least one of said lower recess spacing or said upper recess spacing are in the range of from about 2 to about 10 inches.

7. The carrier of claim 1, wherein said pouch receiving space is configured to hold said pouches in a non-horizontal orientation.

8. The carrier of claim 7, wherein said pouch receiving space is configured to hold said pouches at a pouch orientation angle in a range of 5 to 40° from the horizontal.

9. The carrier of claim 7, wherein said pouch receiving space is configured so that a top portion of a first pouch overlaps with the base portion of an adjacent pouch.

10. The carrier of claim 1, wherein said upper and lower support structures respectively comprise upper and lower groups of slats.

11. A carrier for transporting a plurality of articles on a convey line of a microwave heating system, wherein each of said articles comprises a pouch having a base portion and a top portion, where said base portion is at least twice as thick as said top portion, said carrier comprising:
    a frame comprising first and second spaced apart end members; and
    an upper support structure and a lower support structure extending between said first and said second end members and configured to secure said articles in said carrier,
    wherein:
       a pouch receiving space is defined between an upward facing surface of said lower support structure and a downward facing surface of said upper support structure,
       each of said recesses is configured to receive the base portion of one of said pouches so as to secure the pouch in said pouch receiving space,
       said pouch receiving space is configured to hold said pouches in a non-horizontal orientation, and
       said pouch receiving space is configured so that a top portion of a first pouch overlaps with the base portion of an adjacent pouch.

12. The carrier of claim 11, wherein said pouch receiving space is configured to hold said pouches at a pouch orientation angle in a range of 5 to 40° from the horizontal.

13. The carrier of claim 11, wherein said downward facing surface presents a series of upper recesses and wherein said upward facing surface presents a series of lower recesses and wherein said lower recesses are spaced from one another by a lower recess spacing and said upper recesses are spaced from one another by an upper recess spacing.

14. The carrier of claim 13, wherein said upper recess spacing and said lower recess spacing are substantially the same.

15. The carrier of claim 13, wherein said upper and lower recesses are offset from one another to form an offset region between said upper and lower recesses, and wherein said offset region is configured to receive a base portion of one of said pouches and a top portion of an adjacent pouch in an overlapped configuration.

16. The carrier of claim 13, wherein said lower recess spacing and said upper recess spacing are less than the height of said pouches so that adjacent pouches loaded in said pouch receiving space overlap one another.

17. The carrier of claim 13, wherein said upper recesses and lower recesses are offset from one another by an offset distance and wherein said offset distance is less than one-third of said upper and said lower recess spacing.

18. The carrier of claim 17, wherein said offset distance is in the range of from 0.5 to 3 inches and wherein said lower recess spacing and/or said upper recess spacing are in the range of from about 2 to about 10 inches.

19. A carrier for transporting a plurality of articles on a convey line of a microwave heating system, wherein each of said articles comprises a pouch having a base portion, said carrier comprising:
  a frame comprising an upper support structure and a lower support structure, wherein:
  a pouch receiving space is defined between an upward facing surface of said lower support structure and a downward facing surface of said upper support structure,
  said downward facing surface presents a series of upper recesses,
  said upward facing surface presents a series of lower recesses, and
  each of said lower recesses is configured to receive the base portion of one of said pouches so as to secure the pouch in said pouch receiving space.

20. The carrier of claim 19, wherein:
  said pouch receiving space is configured to hold said pouches in a non-horizontal orientation, and
  said pouch receiving space is configured so that a top portion of a first pouch overlaps with the base portion of an adjacent pouch.

* * * * *